US008915917B2

(12) United States Patent
Doherty et al.

(10) Patent No.: US 8,915,917 B2
(45) Date of Patent: Dec. 23, 2014

(54) INTRAMEDULLARY NAILS FOR LONG BONE FRACTURE SETTING

(75) Inventors: William Doherty, Cork (IE); Patrick O'Connor, County Cork (IE); James Harty, Cork (IE); Hannah Dailey, Cork (IE); Charles Daly, County Cork (IE); Olive O'Driscoll, County Cork (IE)

(73) Assignee: Cork Institute of Technology, Cork (IE)

( * ) Notice: Subject to any disclaimer, the term of this patent is extended or adjusted under 35 U.S.C. 154(b) by 0 days.

(21) Appl. No.: 13/389,130

(22) PCT Filed: Aug. 12, 2010

(86) PCT No.: PCT/IE2010/000047
§ 371 (c)(1),
(2), (4) Date: Feb. 6, 2012

(87) PCT Pub. No.: WO2011/018778
PCT Pub. Date: Feb. 17, 2011

(65) Prior Publication Data
US 2012/0136356 A1    May 31, 2012

(30) Foreign Application Priority Data

Aug. 13, 2009  (IE) .................................... 2009/0623
May 27, 2010   (IE) .................................... 2010/0345

(51) Int. Cl.
*A61B 17/56*   (2006.01)
*A61B 17/58*   (2006.01)
*A61F 2/30*    (2006.01)
*A61B 17/72*   (2006.01)

(52) U.S. Cl.
CPC ......... *A61B 17/7241* (2013.01); *A61B 17/7225* (2013.01)
USPC .............................................. 606/62; 606/64

(58) Field of Classification Search
USPC ................................ 606/246, 62–64, 95, 105
See application file for complete search history.

(56) References Cited

U.S. PATENT DOCUMENTS 5,516,335 A * 5/1996 Kummer et al. ................. 606/63
2005/0273103 A1* 12/2005 Wahl et al. ...................... 606/62
(Continued)

FOREIGN PATENT DOCUMENTS

CN    1 813 639    8/2006
CN    2820114      9/2006
(Continued)

OTHER PUBLICATIONS

International Search Report dated Jan. 18, 2011.

*Primary Examiner* — Mary Hoffman
*Assistant Examiner* — Christina Negrellirodrigue
(74) *Attorney, Agent, or Firm* — Jacobson Holman Hershkovitz, PLLC.

(57) ABSTRACT

An intramedullary nail has a proximal part for engagement with a proximal bone fragment and a distal part for engagement with a distal bone fragment. A motion assembly interconnects the parts and allows limited axial relative motion of the proximal and distal parts. This limited axial motion provides micromotion and in some embodiments also dynamization. The nail may comprise a stem for fastening to one bone fragment and an insert within the stem for fastening to the other bone fragment, the insert being adapted to guide insertion of a bone screw through the stem and to prevent relative rotation of the distal and proximal bone fragments. The motion assembly may include spring bias and/or damping means between the parts, possibly including one or more Belleville washers.

6 Claims, 53 Drawing Sheets

(56) References Cited

U.S. PATENT DOCUMENTS

| | | |
|---|---|---|
| 2006/0129247 A1 | 6/2006 | Brown et al. |
| 2006/0173457 A1* | 8/2006 | Tornier ............... 606/62 |
| 2008/0183171 A1 | 7/2008 | Elghazaly et al. |
| 2009/0048600 A1* | 2/2009 | Matityahu et al. ............... 606/62 |

FOREIGN PATENT DOCUMENTS

| | | |
|---|---|---|
| CN | 1875892 | 12/2006 |
| CN | 101 224 133 | 7/2008 |
| EP | 1 685 803 | 8/2006 |
| WO | WO 2009/002890 | 12/2008 |

* cited by examiner

Fig 15  SECTION A-A

SECTION A-A

SECTION A-A

SECTION B-B

Fig 53   SECTION B-B

INTRAMEDULLARY NAILS FOR LONG BONE FRACTURE SETTING

This is a national stage of PCT/IE10/000047 filed Aug. 12, 2010 and published in English, which claims the priority of Irish number 2009/0623 filed Aug. 13, 2009 and Irish number 2010/0345 filed May 27, 2010, hereby incorporated by reference.

INTRODUCTION

1. Field of the Invention

The invention relates to setting of long bones after fractures.

2. Prior Art Discussion

Fractures of the long bones can be set using an Ilizarov frame (which is external fixation) or using an intramedullary nail (inserted into the hollow canal of the long bones). As shown in FIG. 1, the Ilizarov frame allows the bones to move in a controlled fashion along the longitudinal axis. This motion stimulates healing. The bone fragments are held in place by wires penetrating the skin and attaching to an external frame. The tension in the wire determines the amount of motion between the bone fragments. When loads are placed on the fragments they compress, and when the load is removed they return to their original set position. In general, the Ilizarov frame also admits some rotational motion and the axial and rotational stiffness are highly dependent upon the configuration of the rods and wires.

Intramedullary nails ("IM" nails) are hollow tubes placed internally inside the fractured bone. Screws passing through the bone hold fragments in place at a set distance apart. There may be delayed union or non-union of the bone fragments. When this occurs, a second operation is undertaken whereby a screw is removed to allow one of the bone fragments to move relative to the others and close the gap, promoting compression and hence bone healing. This is called "dynamisation". Dynamisation requires a surgical procedure, with the disadvantages of risk to the patient undergoing anaesthesia and cost of the procedure. Also, as the gap will be closed this may in extreme cases lead to limb shortening, which can be a side-effect of the dynamisation procedure. Limb shortening occurs due to the dynamic bone fragment not being able to return to its set position.

Examples of published documents in this field are Chinese Patent Publication Nos. CN1875892 and CN2820114.

The invention is directed towards achieving improved long bone setting.

SUMMARY

According to the invention, there is provided an intramedullary nail comprising a first part having a first opening to receive a first fixture for engagement with a first bone fragment. There is a second part having a second opening to receive a second fixture for engagement with a second bone fragment. A motion assembly allows limited axial relative movement of the first and second parts.

In one embodiment, the second part is a nail stem and the first part is an insert within the stem.

In one embodiment, the insert is adapted to guide insertion of a bone screw through the stem.

In one embodiment, the insert is constrained to move axially only within the stem without relative rotation of the insert and the stem. In one embodiment, the insert is keyed in the stem.

In one embodiment, the motion assembly is adapted to provide spring bias and/or damping between the parts.

In one embodiment, the motion assembly comprises a removable spring. The spring may comprise a plurality of spring elements. The motion assembly may be adapted to accommodate any of a range of spring elements to pre-set a bias range. The spring or spring elements may comprise one or more Belleville washers.

In one embodiment, the motion assembly is adapted to allow movement without bias or damping.

In one embodiment:
the second part comprises a nail stem with an aperture,
the first part comprises an insert within the stem, the insert being constrained to move axially only within the stem;
the motion assembly comprises the insert, the stem, and one or more bone screws for engagement with a first bone fragment, and
wherein there is a difference in cross-sectional size between the bone screw and the aperture, said difference allowing movement.

In one embodiment, the motion assembly comprises a dynamisation adjustment mechanism for allowing adjustment of the interfragmentary gap within which said movement occurs.

In one embodiment, the dynamisation adjustment mechanism is adapted to adjust axial location or range of permitted axial locations within a nail stem of an insert for attachment to a bone fragment, the nail stem being for attachment to the other bone fragment.

In one embodiment, the dynamisation adjustment mechanism comprises a retainer in the stem, axial position of the retainer being adjustable to set a limit on motion of the insert relative to the stem.

In one embodiment, the retainer engages threads in the stem, rotation of the retainer setting its axial position.

In one embodiment, the dynamisation adjustment mechanism is adapted to varying minimum and/or maximum separation of the proximal and distal bone fragments.

In one embodiment, the adjustment mechanism is also adapted to adjust spring bias.

In one embodiment, the motion assembly allows movement under spring bias, and upon full spring compression the dynamisation adjustment mechanism is adapted to allow de-compression of the spring while bringing the proximal and distal parts closer together.

In one embodiment, the dynamisation adjustment mechanism is adapted to lock a position between a bearing and the stem, the bearing being acted upon by the insert via the spring.

In one embodiment, the bearing is a sleeve within which the insert is located.

In one embodiment, the dynamisation adjustment mechanism is adapted to operate upon patient application of weight.

In another embodiment, the dynamisation adjustment mechanism is adapted to allow progressive relative axial mutual movement of the parts for progressive reduction of an interfragmentary gap.

In one embodiment, the dynamisation adjustment mechanism comprises a ratchet mechanism and adjustment is from one ratchet position to another.

In one embodiment, the dynamisation adjustment mechanism comprises a series of grooves in a nail stem and a ratchet for engagement in the grooves.

In a further embodiment, the ratchet comprises a radial spring configured to engage a ratchet groove.

In one embodiment, the dynamisation adjustment mechanism is adapted to allow relative motion by engagement of a pin in a slot, in which the pin is not breakable under normal conditions.

In one embodiment, the dynamisation adjustment mechanism includes a link having a failure level of applied force.

In one embodiment, the link is arranged to be under shear force and to fail at a threshold shear force.

In one embodiment, there is a first range of relative motion before failure and a second range after failure.

In one embodiment, a link extends through a short slot and a second link extends through a longer slot.

In one embodiment, the nail comprises a surgeon adjustment interface which translates rotational movement caused by a surgeon into axial movement within the stem to close the gap between the proximal and distal bone fragments.

In one embodiment, the interface comprises an exposed screw which pushes an internal sliding and non-rotating component within the stem.

DETAILED DESCRIPTION OF THE INVENTION

Figures

The invention will be more clearly understood from the following description of various embodiments thereof, given by way of example only, with reference to the accompanying drawings, in which.

DETAILED DESCRIPTION

Figure 1:
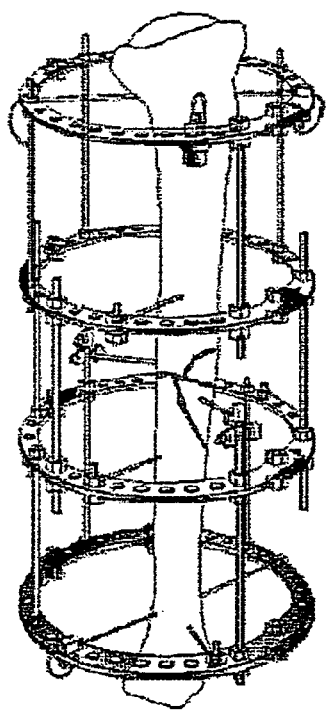
FIG. 1 is a perspective view of a prior art external frame arrangement as set out above.
Figure 2:
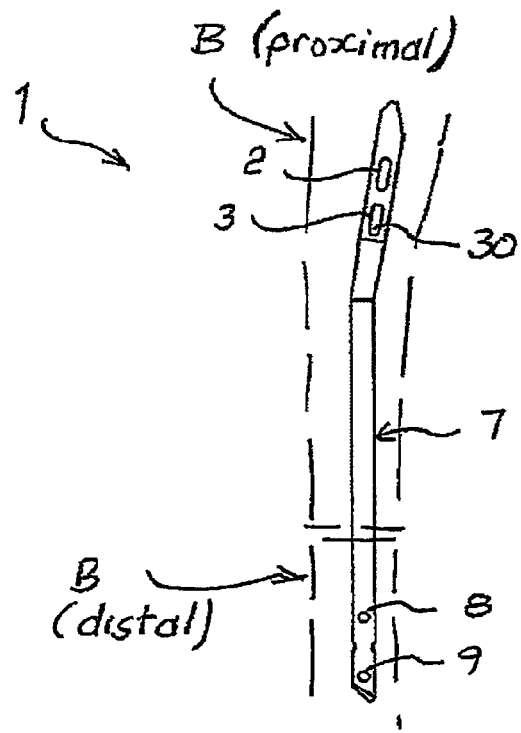
FIG. 2 shows a nail of the invention in use and FIG. 3 shows an exploded view of the nail.

Recent advances in medicine have demonstrated that accelerated healing of long bone fractures can be induced by mechanical stimulation of the interfragmentary gap in a process described clinically as "micromotion". Described herein is an intermedullary nail that includes a first part, a second part and a motion assembly to allow limited axial relative micromotion of the parts. According to one type of approach, the first part (such as an insert) includes a first opening to receive a first fixture (such as a bone screw) that is secured to a first bone fragment. The second part (such as a nail body) has a second opening to receive a second fixture (such as another bone screw) that is secured to a second bone fragment. The second part has an inner diameter that is larger than the first part's outer diameter so that the first part fits inside the second part. The second part has a third opening that also receives the first fixture. The third opening has an axial length to establish a maximum range of distances between the first part and said second part.

In some embodiments, the "motion assembly" is a set of parts which form a chain of interconnection between the first and second parts, including for example springs such as Belleville washers. In other embodiments the "motion assembly" constitutes the first and second parts, configured to allow controlled relative movement between the parts.

In clinical practice, a small percentage of fractures fail to unite due to a variety of factors including the type of fracture, degree of soft tissue injury, torsional stability of the fixator, distance between bone fragments after fixation, and patient risk factors such as smoking. Delayed union or non-union of the bone fragments is commonly characterised by a large interfragmentary gap (typically more than about 3 mm). In such a situation micromotion occurs insofar as the proximal and distal bone fragments move relative to each other, but because they are so far apart healing does not occur.

This problem can be dealt with by modifying the fixator so as to reduce the gap between the bone fragments to the range associated with positive healing outcomes. Fixator modification is typically irreversible and allows dynamic closure of the fracture gap, so this is referred to clinically as "dynamisation". In this embodiment, the motion assembly comprises components which can produce stimulatory micromotion and dynamisation in case of fracture non-union.

In this specification the terms "proximal" and "first" are used interchangeably, as are the terms "distal" and "second".

Referring to FIGS. 2 to 11 an exemplary intramedullary nail (henceforth "nail") 1 has a stem 7 and is inserted in a long bone B across a fracture, joining a first bone fragment part (such as a "proximal" part as hereafter described) and a second bone fragment part (such as a "distal" part as hereafter described). According to the exemplary approach depicted in FIGS. 2 to 11, the proximal end of the nail has slots 2 and 3 in the stem 7. Screws are inserted through the slots 2 and 3 and engage a motion assembly (depicted as an insert 30 in FIGS. 2 to 11) within the stem 7 as described in more detail below. The lower shank of the stem 7 has through-holes 8 and 9 for fixed engagement of the stem 7 with the distal bone fragment.

The distal end of the stem 7 is fixed to the distal bone fragment by screws through the holes 8 and 9. The insert 30, within the stem 7, is secured to the proximal bone fragment by engagement with screws 4 and 5 through apertures 31 and 32.

The insert 30 with respect to the stem 7 is movable to a limited extent under spring bias and damping to provide micromotion. "Micromotion" is regarded in this specification as a small interfragmentary motion (i.e. less than about 1.5 mm) that is allowed to occur repeatedly. Controlled mechanical stimulation of the interfragmentary gap via application of micromotion in the direction of the long bone axis has been shown in animal experiments and human-subjects clinical trials to accelerate the proliferation of callus at the fracture site and reduce time to clinical union of the bone fragments.

Returning to FIGS. 2 through 11, the embodiment of the nail 1 depicted therein includes:

The stem 7 having, at the proximal end, internal ridges 15, internal threads 16, and slots 2 and 3.

A sleeve 20 having an elongate slot 21 and being configured for insertion into the stem 7, and to house the insert 30 and Belleville washers 33, providing a bearing surface for the washers 33.

The insert 30 having the through-holes 31 and 32.

Belleville washers 33 around a narrower length 34 of the insert 30, and being engaged between the insert 30 and the sleeve 20 at its lower end.

A ratchet 40 carrying a radial spring 60 engaging the ridges 15 of the stem 7.

A pusher piece 50, engaging the threads 16 of the stem 7 and pushing against the ratchet 40.

Figure 3:
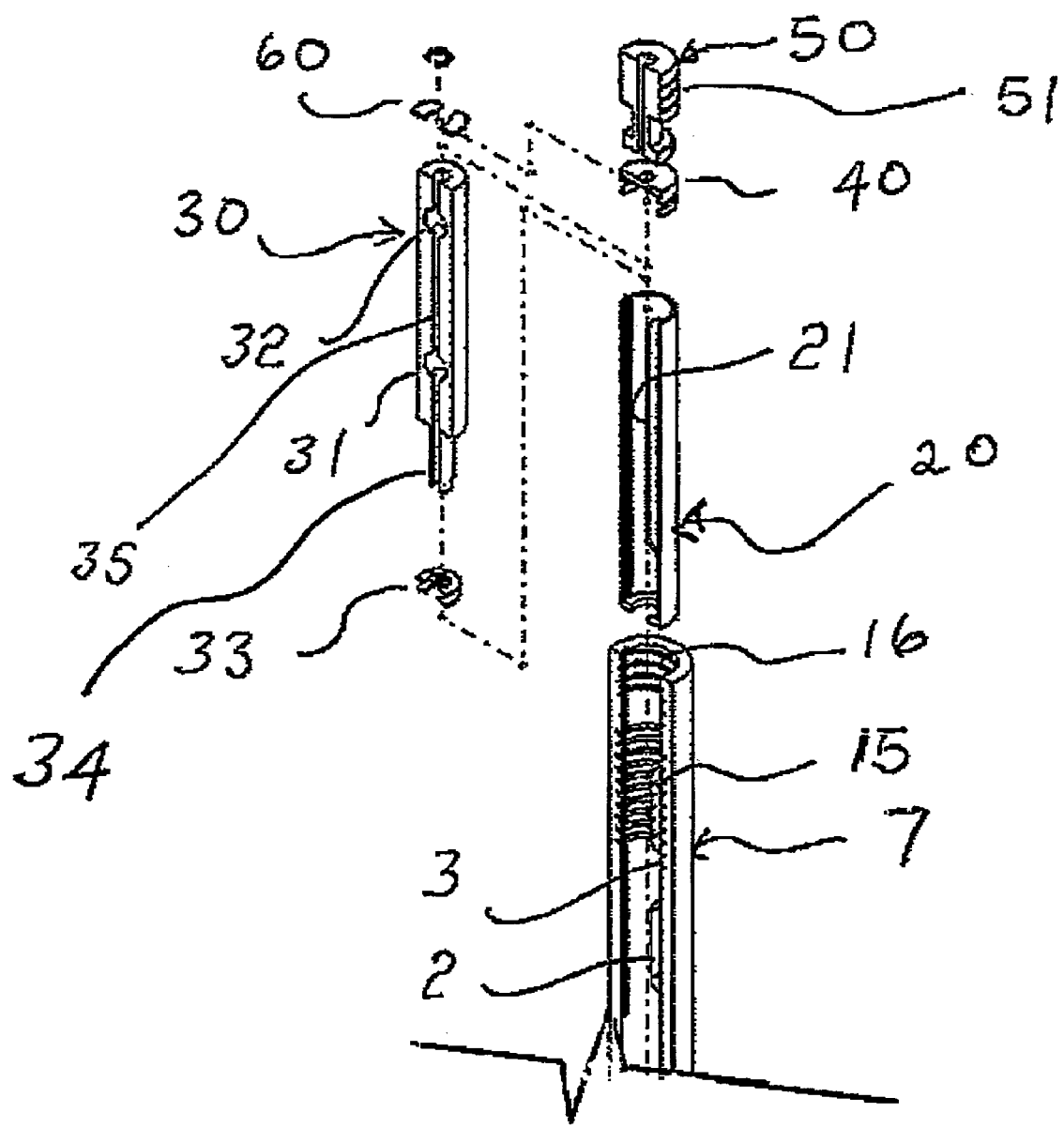
Figure 4:
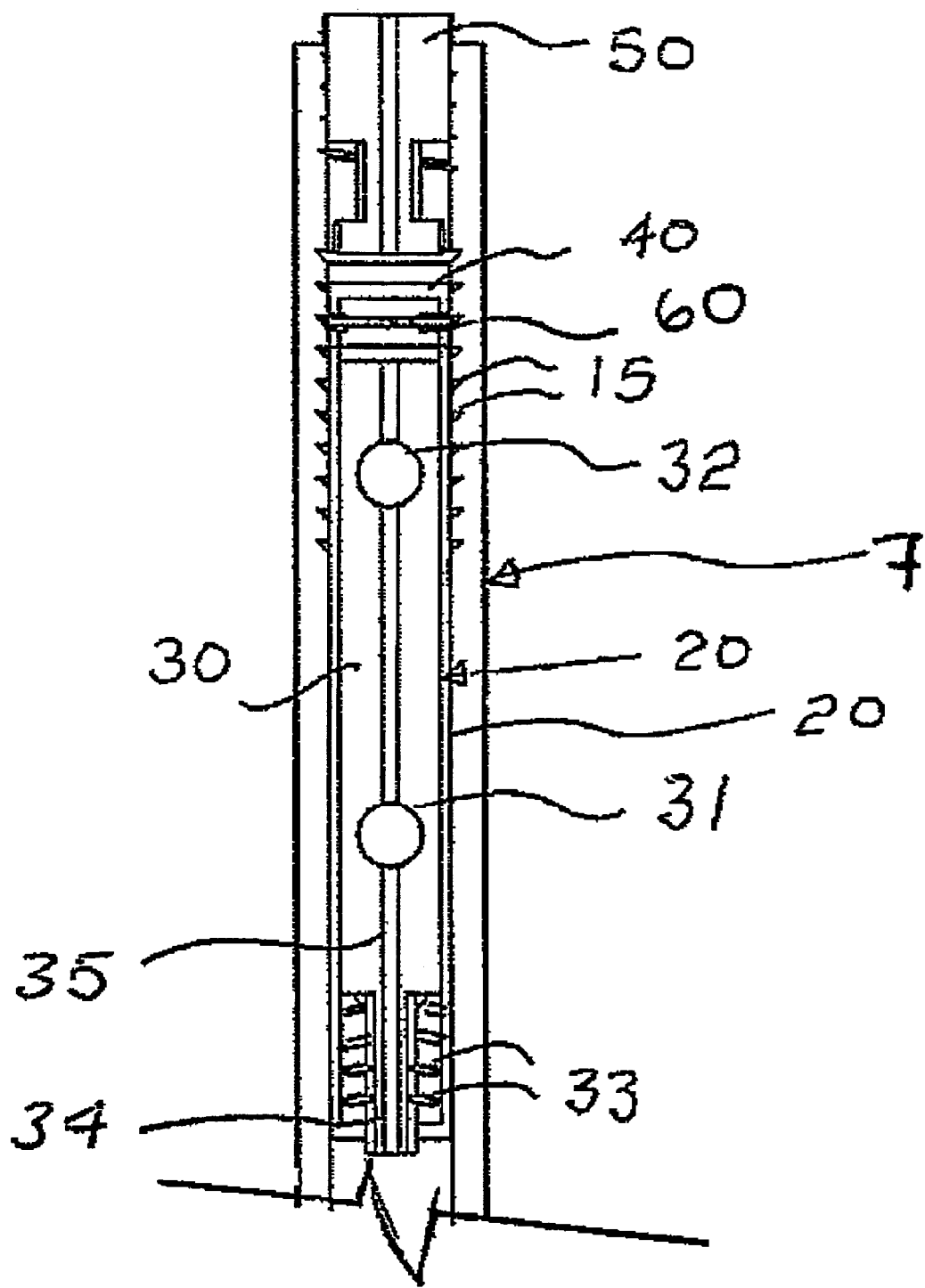
FIG. 4 is a cross-sectional view showing an upper part of the nail.
Figure 5:
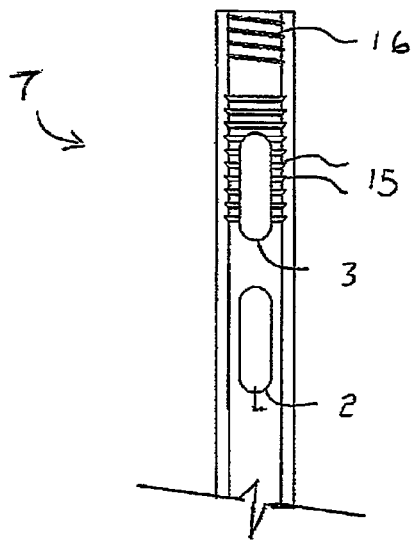
FIG. 5 is a cross-sectional view showing a stem of the nail in more detail
Figure 6:
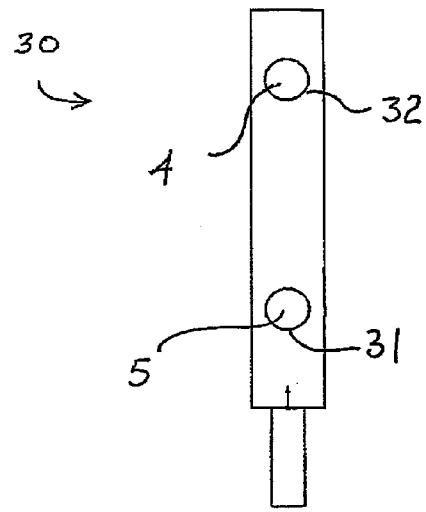
FIG. 6 shows an insert for engagement with a proximal bone fragment.
Figure 7:
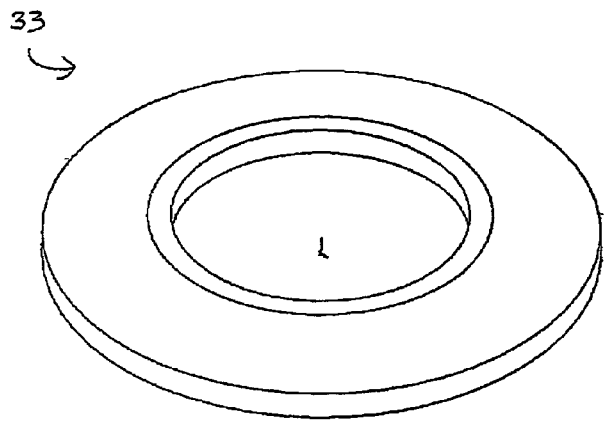
FIGS. 7 and 8 are perspective and side views of a Belleville spring washer for micromotion bias.
Figure 8:
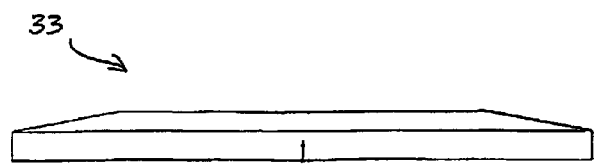
Figure 9:
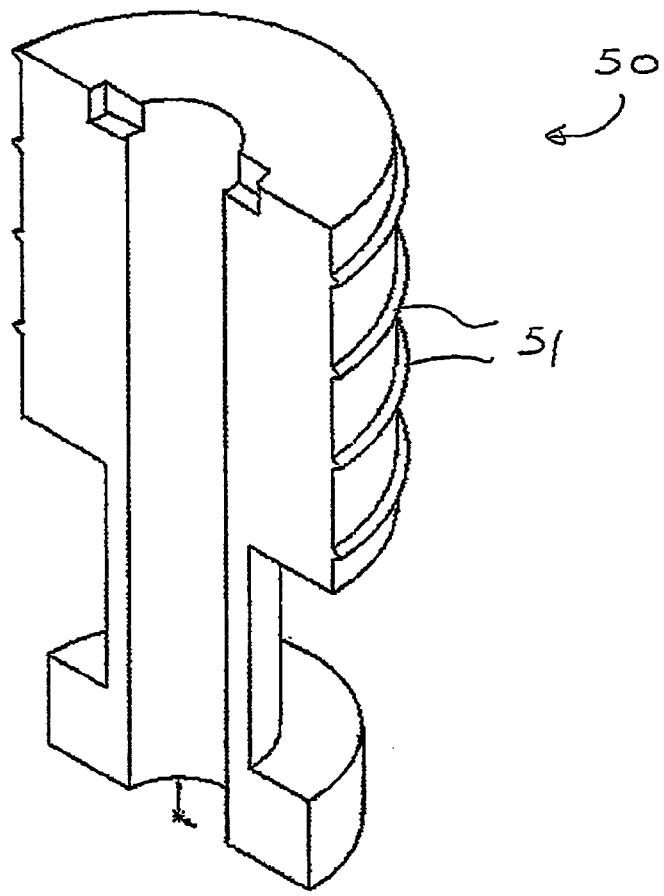
FIG. 9 is a perspective view of a pusher piece to set an initial position within the nail.
Figure 10:
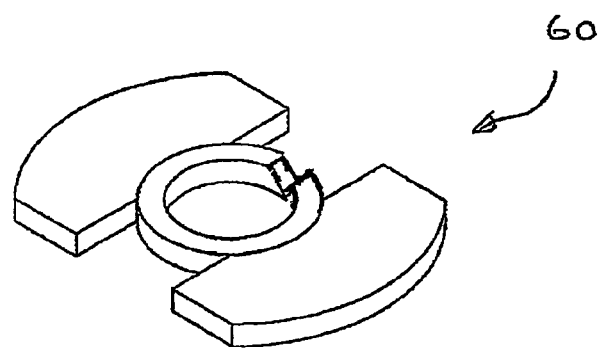
FIG. 10 is a perspective view of a radial spring providing discrete positions within the nail when it engages with one of the grooves in the stem.

The insert 30 embodiment depicted in FIG. 3 consists of the following:

A hollow space region 35 (hereinafter referred to as "Central lumen 35") to accommodate a guide-wire during the clinical procedure. The nail preserves the central lumen for guide wire usage during nail insertion. Some embodiments may be a two-part assembly wherein a second part is added later that blocks the guide wire, but this occurs after the guide wire has been removed.

A keying mechanism to ensure rotational alignment with the external insert assembly.

Screw holes 31 and 32 to accommodate fixation screws 4 and 5. The screw hole locations are aligned with the slots 2 and 3 in the stem 7.

The distal section of the insert 30 has a reduced diameter 34 and shoulder to facilitate the inclusion of a spring mechanism/shock absorption system 33 implemented with (in the embodiment of FIG. 3) Belleville washers 33. This reduced diameter section mates with a hole at the base of the sleeve 20 such that vertical movement of the insert 30 is accommodated. This arrangement will facilitate micromotion of the insert 30 as it sits on the Belleville washers 33, exerting force via the washers onto the base of the sleeve 20.

The insert 30 and the washers 33 are placed in position before the ratchet assembly 60 and 40 is screwed in place at the top of the outer sleeve 20. The insert 30 central lumen 35 allows passage of a guide wire. The two holes 31 and 32 allow fastening of the insert 30 by bone fastener screws 4 and 5 to the proximal bone fragment. The screws 4 and 5 pass through the keyed groove 21 in the sleeve 20. The narrower diameter length 34 of the insert 30 allows the insert 30 to sit on the Belleville washers 33 and provides a centring mechanism for the washers 33.

The washers 33 provide vibration damping and restoring force for the insert 30 as weight/downward force is applied to the insert 30 by the proximal bone fragment. The Belleville washers 33 are particularly advantageous in the nail 1 due to their high spring constants, suitability to confined space, large load capability, and short displacement. Various combinations of these washers can be used to give a wide range of displacement and restoring forces. Although Belleville washers are specifically depicted in the particular embodiment of FIG. 3, in alternate embodiments other elements may be employed to effect the spring mechanism/shock absorption component. Examples include coned-disc washers, wave washers, slotted washers, finger washers, split washers, curved washers, volute springs, or coil springs (standard, variable pitch, barrel, hourglass, or conical). For simplicity, the remainder of the description will largely refer to Belleville washers rather than a spring mechanism/shock absorption component.

Figure 11:
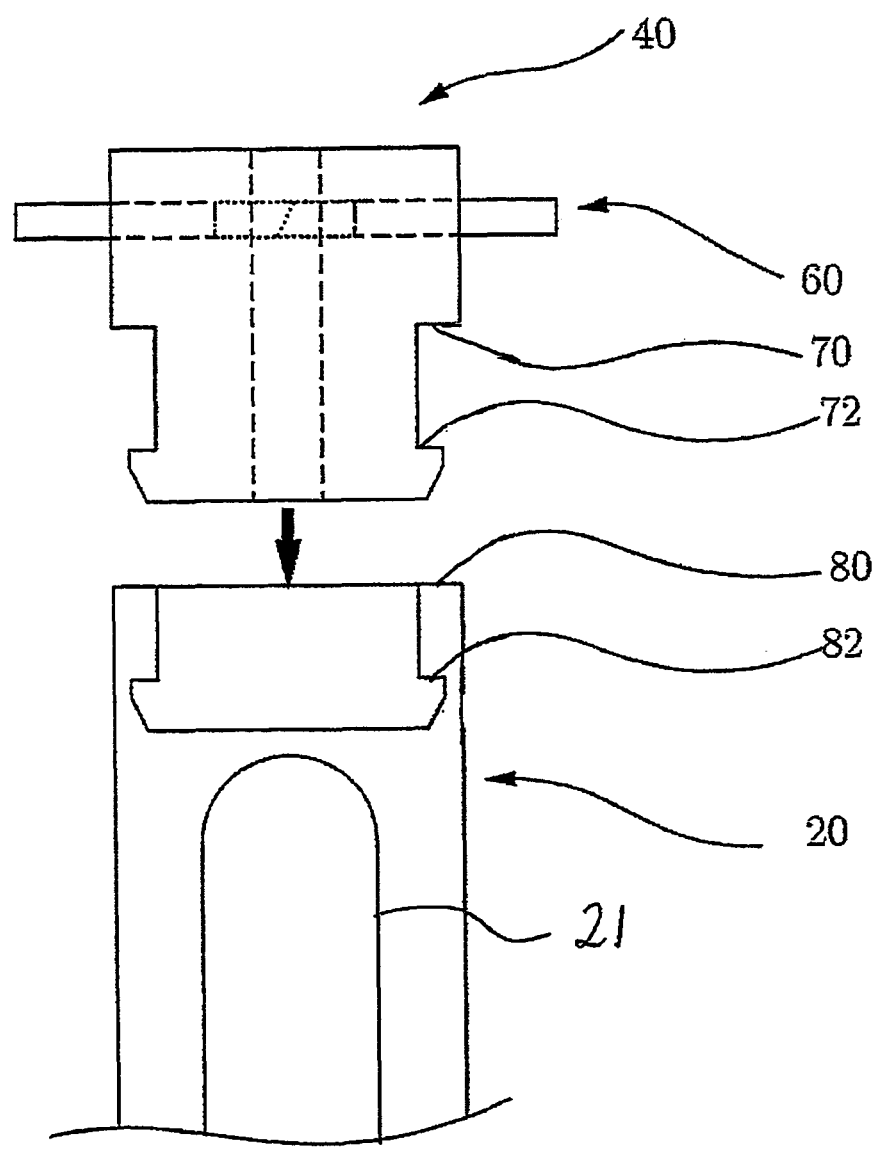
FIG. 11 is a diagammatic cross-sectional view showing a ratchet which carries the radial spring, the proximal end of a sleeve within the stem, and how they engage with each other to provide micromotion auto adjustment.

As shown particularly in FIG. 11, the ratchet 40 has a tapered profile which mates with a negative tapered profile of the proximal end of the sleeve 20. A ratchet surface 70 mates with a sleeve surface 80, and a ratchet surface 72 mates with a sleeve surface 82, preventing de-coupling of the ratchet 40 from the sleeve 20 in use.

Figure 12:
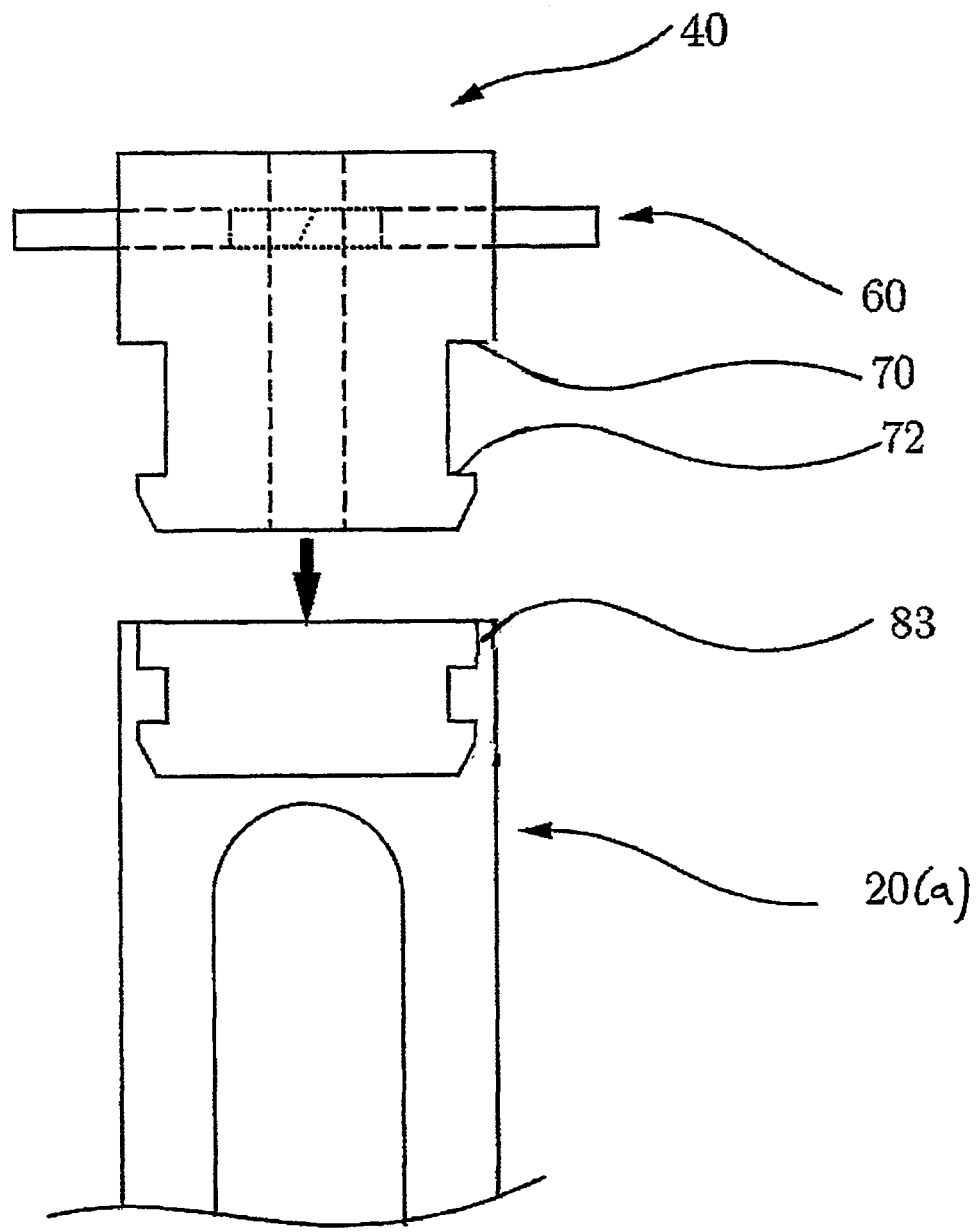
FIG. 12 is a view similar to that of FIG. 11, showing an alternative arrangement.

In another embodiment, as shown in FIG. 12, a sleeve 20(a) has a shoulder 83. This arrangement of profiles allows insertion of Belleville washers 33 at this location in addition to or instead of the location at the distal end of the insert 30. In a further alternative embodiment, the function of the sleeve 20 or 20(a) could be performed by a solid piece, having slots to accommodate the bone-fixing screws.

The insert 30 has a limited freedom of movement under bias of the washers 33 with respect to the stem 7. The force exerted by the washers 33 are set by the following:

(a) Initial choice by the surgeon of the appropriate assembly is based on patient weight. The surgeon is provided with a choice of micromotion assemblies to use for any particular operation. The full assembly including Belleville washers 33, insert 30, sleeve 20, ratchet mechanism 40/60 is factory set and labelled according to patient weight. The overall spring property of the set of Belleville washers 33 is determined by geometrical properties such as washer height, inner/outer diameter, and material thickness. Multiple washers can be arranged in parallel or series configurations to provide the specific spring properties required for a given patient weight class. Interaction effects such as friction between Belleville washers are well-known and can be accounted for in the labelling of the assembly according to patient weight class. The surgeon does not need to perform any assembly work.

(b) Adjustment of the axial position of the pusher piece 50 within the stem 7. The adjustment is achieved by rotation of the pusher piece 50 on the threads 16. This movement pushes the ratchet 40/60 into engagement with a next groove 15, and the ratchet 40 engages the proximal end of the sleeve 20.

The chain for interconnection of the proximal bone fragment to the distal bone fragment is as follows:

screws 4, 5;
insert 30,
Belleville washers 33,
sleeve 20 (urged downwardly by the washers 33);

ratchet 40;

ratchet spring 60 snap-fitted into one of the stem 7 grooves 15, the stem 7, secured to the distal bone fragment at the screw holes 8 and 9.

In the surgical procedure the surgeon chooses a particular nail to suit the weight and size of the patient. The surgeon will then choose the appropriate motion assembly which will be labelled according to patient weight and put the motion assembly into the nail 1 during the surgical procedure. This nail 1 will have the appropriate number of Belleville washers 33 (as described above). In the surgical procedure the surgeon rotates the pusher piece 50 to urge the ratchet 40/60 down to snap-fit into an appropriate groove 15. This in turn pushes down the sleeve 20.

Figure 13:
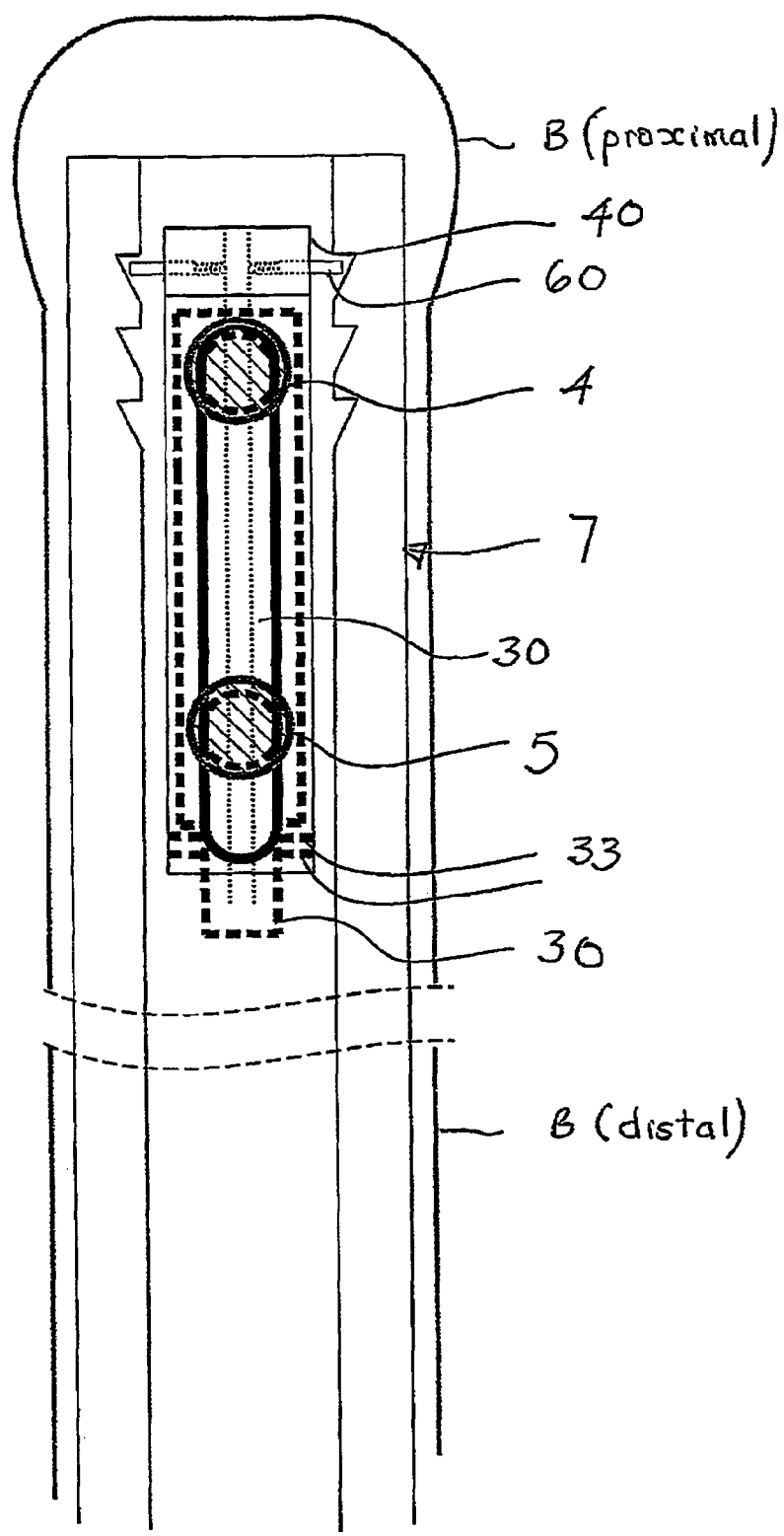
FIGS. 13 and 14 are diagrams showing operation of the nail of FIGS. 2 to 11, particularly how micromotion automatic adjustment is achieved.
Figure 14:
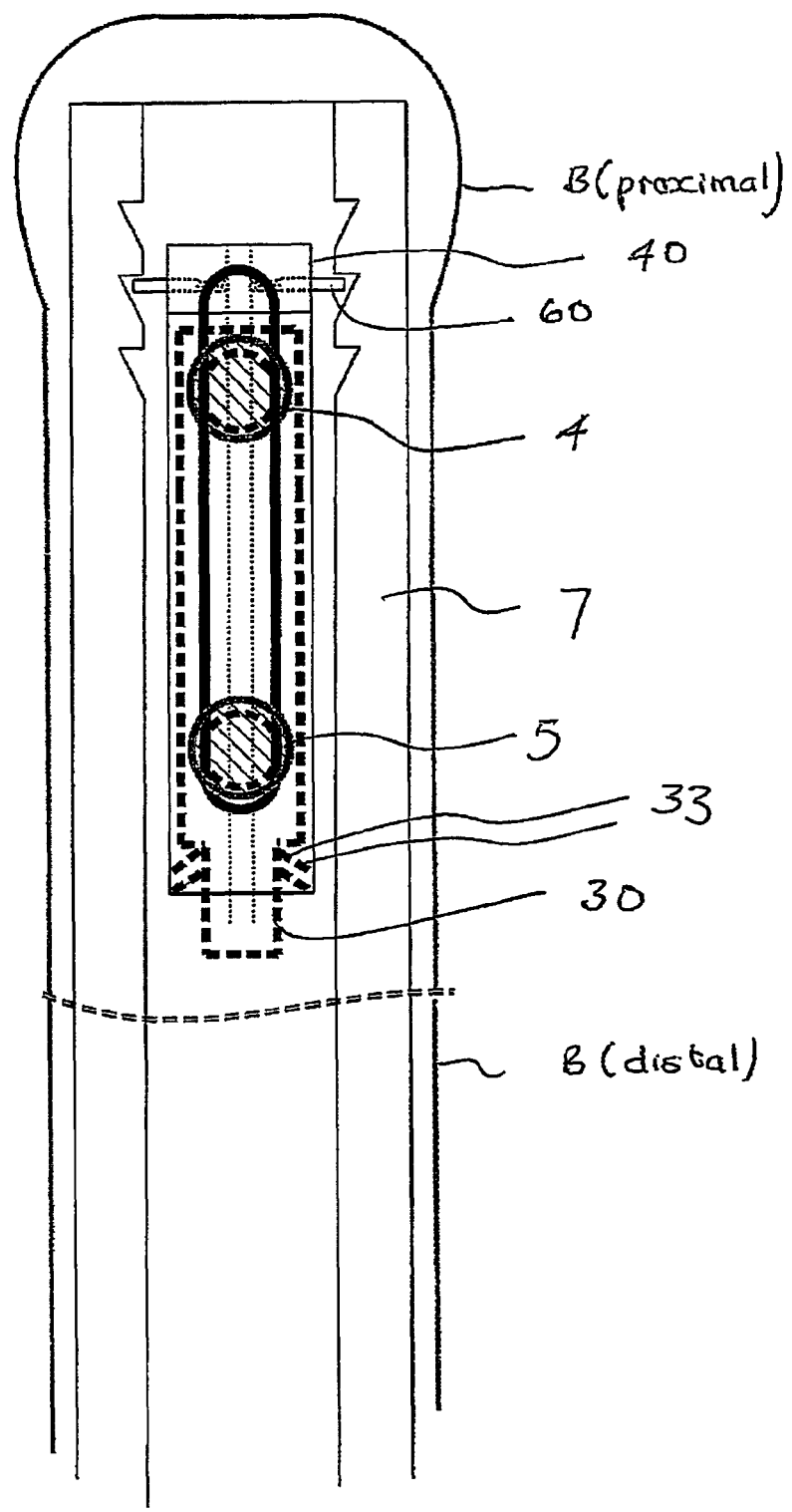

FIGS. 13 and 14 show diagrammatically operation of the nail 1 to achieve automatic micromotion adjustment. FIG. 13 shows the nail 1 after the surgical procedure, with the Belleville washers 33 fully compressed. On application of weight the insert 30 cannot move further and so the insert 30 and sleeve 20 move as one unit pulling the ratchet 40/60 to the next groove 15, provided enough force is applied to overcome the ratchet forces. FIG. 14 shows the position after this automatic adjustment, and the fracture between the proximal and distal bone fragments has closed. The sleeve and the insert 30 have moved downwards, as has the proximal bone fragment relative to the distal bone fragment. The Belleville washers 33 are no longer compressed because the sleeve 20 has moved down relative to the stem 7. Thus, the invention aids the bone-healing process, for example for tibia fractures or femoral fractures.

During leg swing phase, the tendency is for the bone fragments to separate therefore releasing the compressive forces on the Belleville washers 33 such that they tend to return to their original profile. The extent to which the bone fragments can separate is maximised by the existence of the ratchet mechanism 40, which serves as a hard stop for the motion assembly (and therefore bone fragment separation process) during the leg swing motion.

It will be appreciated that the invention of at least some embodiments achieves micromotion between bone fragments, while maintaining the overall stability achieved by an intra-medullary device, accurate setting of bone separation distances during the surgical procedure, non-invasive correction of bone fragment separation distances post-operation in the event that the bone fragment separation distances were miscalculated during the procedure, and/or prevents post-operative bone fragment separation during leg swing phase.

The ratchet mechanism 40 allows one to increment the motion assembly down into the intra-medullary nail in a controlled fashion. This will allow the surgeon to accurately locate the insert 30 within the nail 1 as well as move the insert 30 incrementally down into the stem 7 on application of a force. The ratchet facilitates accurate location of the insert 30 and hence accurate separate distance of apposing bone fragments during the surgical procedure. Also, the ratchet mechanism 40 aids progressive compression at the fracture site. The internal screw threads 16 accommodate the mating screw thread 51 on the pusher piece 50. Ability to screw in the pusher piece 50 means that the vertical location of the insert 30 can be controlled by controlling the amount by which the pusher piece 50 is screwed down into the sleeve 10. Slots may be in either the proximal or distal locations or both.

The following describes other embodiments.

The pusher piece may or may not be attached to the motion assembly 30. It is used to push the sleeve in a controlled and measured fashion. The bottom of the pusher piece butts against the top of the sleeve or the ratchet either directly of by use of an interposition device such as a spring. The pusher piece has an internal cental lumen to facilitate tracking of a guide-wire during the procedure. The rotational action of the pusher piece is translated into vertical motion of the motion assembly 30. Alternative methods for inserting the pusher piece may be employed, such as direct vertical force and clicking into a slot. The insert and the sleeve must not rotate as its rotational orientation must remain constant so as to align it with the slots in the stem. This is facilitated by keying the insert assemblies with the inside of the nail.

Rotational stability of the insert and the outer sleeve can be maintained by keying mechanisms or other appropriate rotational stability mechanisms. An objective is to ensure alignment of the screw slots and screw holes in the nail 1 and the insert. For this to happen, the rotational motion of the pusher piece is translated into vertical motion of the insert with no possibility of rotation of the insert 30 once it has engaged. If the pusher piece is inserted by direct vertical force or by clicking into a slot, rotational alignment of the insert/assembly should be maintained.

The ratchet is such that a threshold force is exceeded for the insert to move from one ratchet position to the next. This may be a function of ratchet pitch or spring stiffness. The distance between ratchet grooves provides accurate setting of bone fragment separation during the procedure. High resolution in the mechanism for accurate setting and maintenance of bone fragment separation distance and resultant optimum fracture union.

The ratchet prevents the outer sleeve and insert from migrating up the nail. Positioning of the outer sleeve and therefore the insert is achieved initially by means of screwing/pushing/clicking the pusher piece down into the nail and thereafter (auto adjustment) by having the patient apply weight until a threshold weight is exceeded.

Keying mechanisms operate to:
i. retain correct relative orientation of the sleeve and the insert during insertion into the nail stem 7, and
ii. interface with the internal diameter of the tibia nail.

A full length slot (or plurality of slots) facilitates the dynamic fixation process. The slot in the sleeve lines up with the dynamic slots in the nail stem and the screw holes in the insert. These slots may be parallel, or in sequence or in differing positions on the nail. It is important to retain rotational alignment between the slots in the nail and in the insert/sleeve assembly and the screw holes in the insert. Keying mechanisms ensure alignment while the motion assembly is being inserted into the nail.

Figure 15:
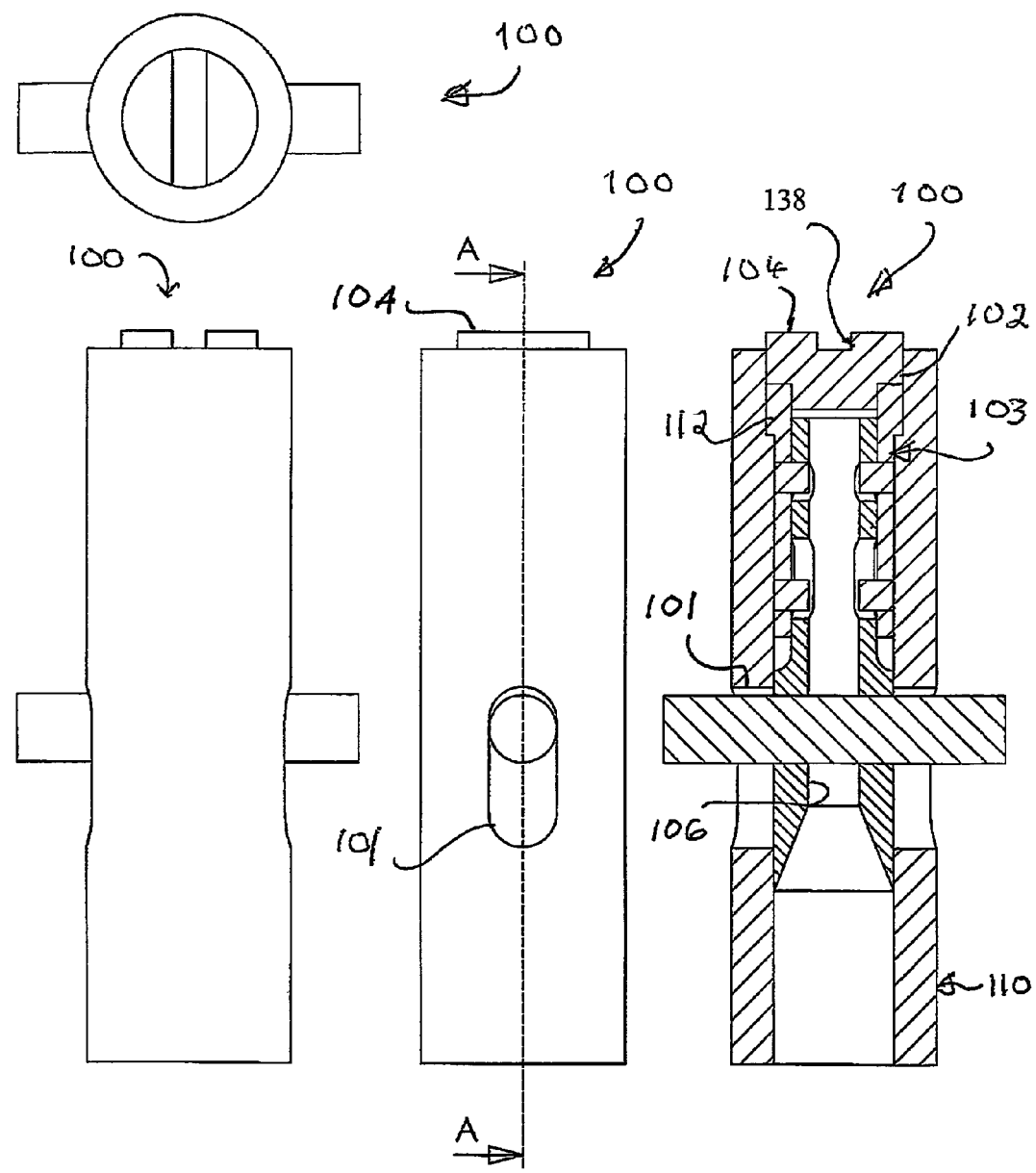
FIG. 15 shows an alternative nail of the invention from the top, front, and right views, as well as a section view.
Figure 16:
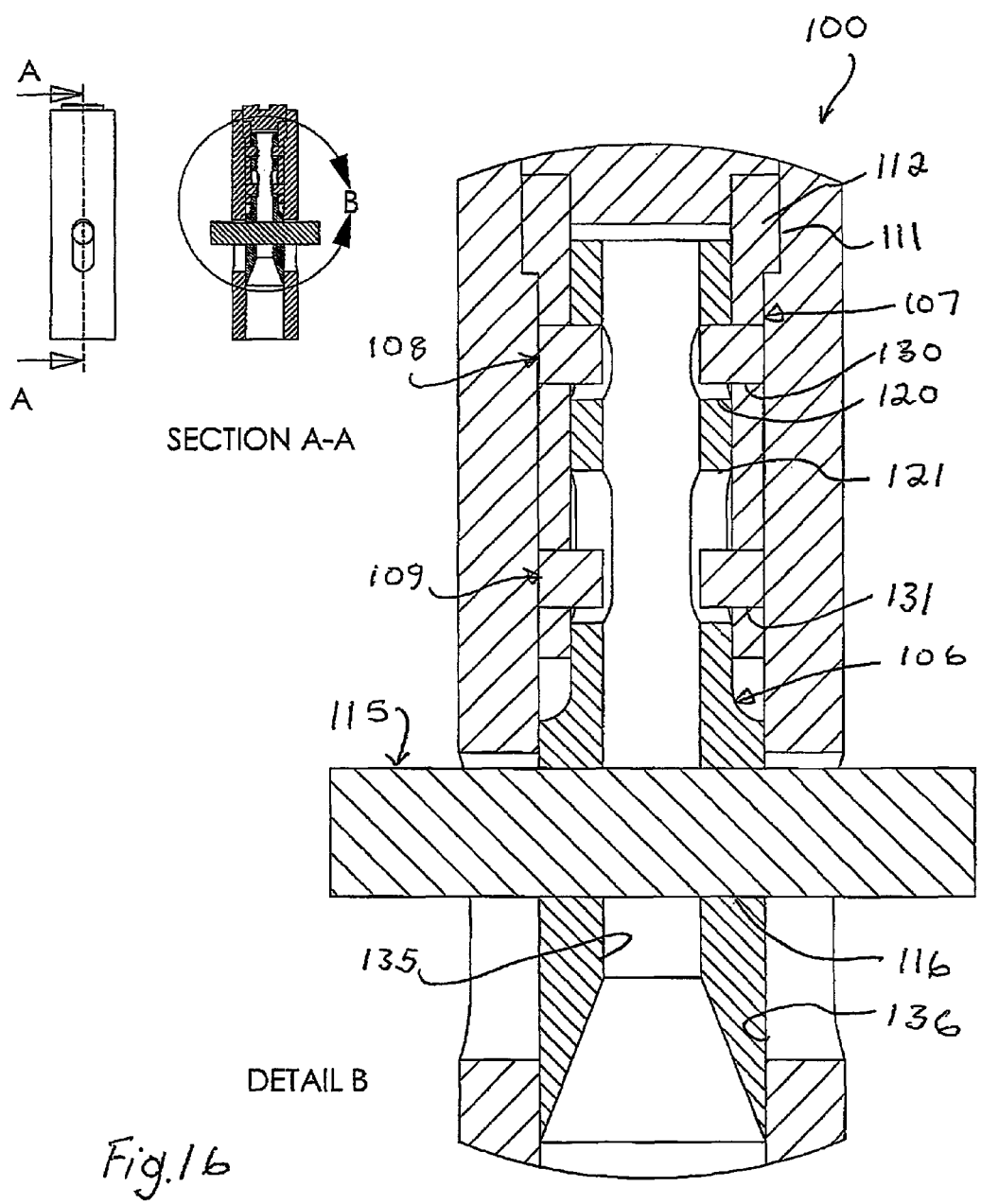
FIG. 16 is a cross-sectional view of part of the nail.
Figure 17:
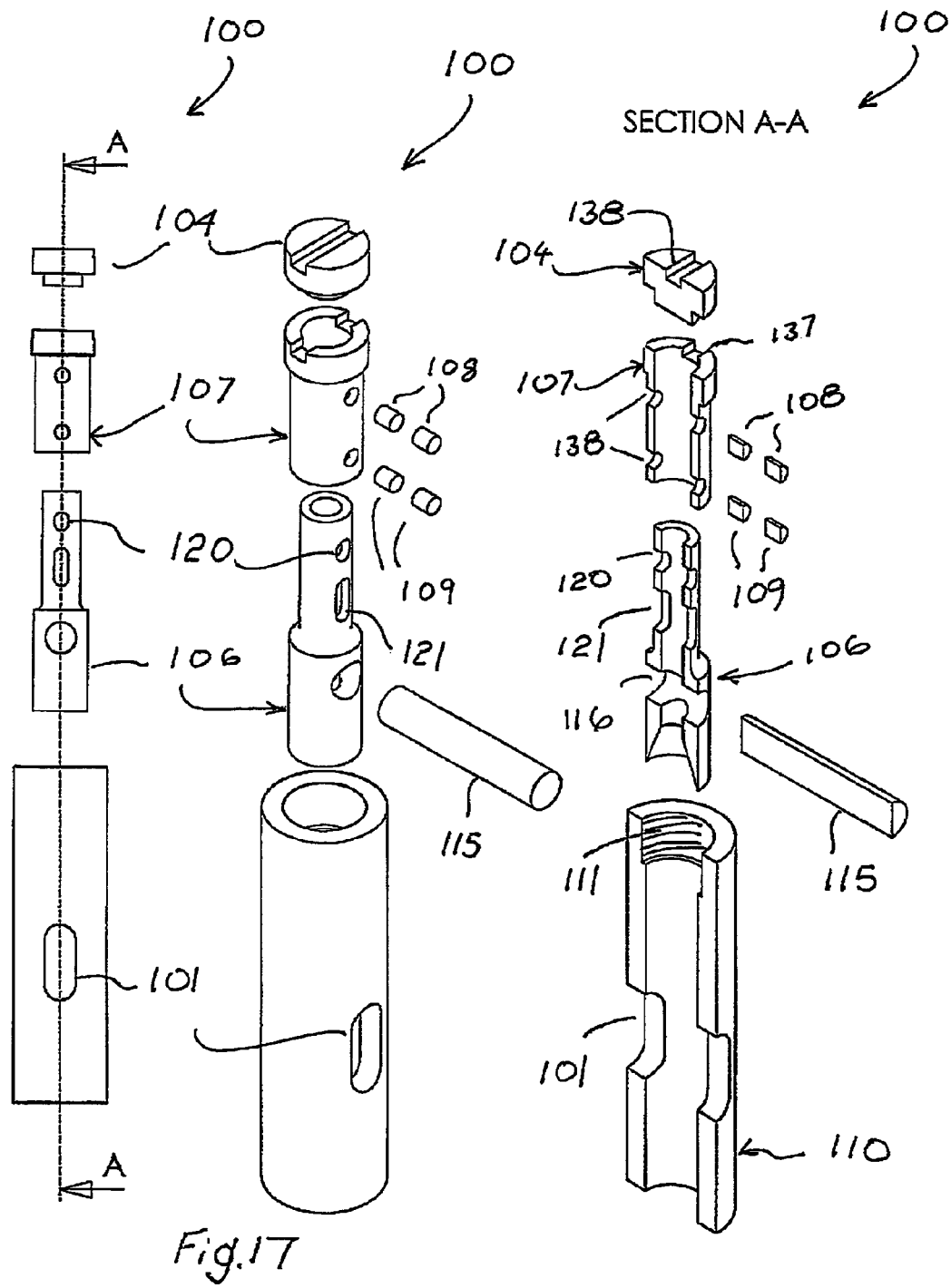
FIG. 17 is a set of exploded assembly drawings of this nail including a left view, an isometric view, and a sectioned isometric view.

Referring to FIGS. 15 to 17, only the proximal end of an intramedullary nail 100 of another embodiment is shown. The nail 100 is shown in simplified form with a single stem slot 101 by way of example. The nail 100 has a stem 110 with a short threaded section 102 in the proximal end, which may receive likewise threaded components including but not limited to a motion assembly 103 incorporating both micromotion and dynamisation capabilities and an end cap 104.

In the embodiment shown in FIGS. 15 to 17, an inner insert 106 and an outer insert 107 are pre-assembled using two pairs of shear pins 108 and 109 for dynamisation. The motion assembly 103 (shown most clearly in FIG. 15) is inserted into the nail stem 110 and secured to the internal threads 111 in the proximal end of the nail stem 110 via external threads 112 in the top of the outer insert 107 (shown most clearly in FIG. 17). A proximal bone fragment is secured by engagement with a bone screw 115 inserted through the slot 101 in the nail stem 110 and a hole 116 in the inner insert 106. The end cap 104 is secured inside the nail stem 110 by engagement with the internal threads 111 in the proximal end of the nail stem 110 and/or the outer insert.

After the motion assembly 103 is secured inside the nail stem lumen, the inner insert 106, which is attached to the proximal bone fragment via the bone screw 115, is movable with respect to the nail stem 110, which is attached to the distal bone fragment via the distal bone screw. This relative motion comprises three phases:

Phase I (Micromotion)—The dynamisation unit 103 allows controlled bone fragment separation as the upper shear pin pair 108 travels in an upper slot 120 in the inner insert 106. The interfragmentary micromotion distance is chosen to accelerate callus formation and fracture healing by mechanical stimulation. The motion assembly 103 operates in Phase I until a defined threshold load is applied by the patient by bearing weight on the leg containing the device. Above the threshold load, the upper shear pins 108 will be severed by the shearing action of the inner insert 106 and outer insert 107.

Phase II (Partial Dynamisation)—In the event that nonunion occurs the patient can be asked to apply weight to the bone, to thereby cause dynamisation to occur. This is because the upper shear pins 108 fail, and the motion assembly 103 allows controlled bone fragment separation as the lower shear pin pair 109 travels in a lower slot 121 in the inner insert 106. The partial dynamisation distance is chosen to improve fracture apposition to promote healing in cases of delayed union or non-union. The motion assembly 103 operates in Phase II until a defined threshold load is applied by the patient by standing on the leg containing the device. Above the threshold load, the lower shear pins 109 will be severed by the shearing action of the inner insert 106 and outer insert 107.

Phase III (Full Dynamisation)—After both pairs of shear pins 108 and 109 have failed, the separation of bone fragments is controlled by translation of the bone screw 115 in the slot 101 in the proximal end of the nail stem 110 a distance dictated by the length of the slot 101 in the nail stem 110.

Hence, the device described in this embodiment achieves mechanical stimulation for accelerated healing via interfragmentary micromotion, controlled bone separation during both stance and swing phases via mechanical hard-stops, and multi-stage non-surgical dynamisation to provide controlled apposition of the proximal and distal bone fragments.

In more detail, the motion assembly 103 comprises:

The inner insert 106 having a larger-diameter lower end for insertion into the lumen of the nail stem 110, a smaller-diameter upper end for insertion into the outer insert 107, an inner diameter tapered at the proximal end, a through-hole 116 for the bone screw 115, and two pairs of slots 120 and 121 for the upper and lower shear pin pairs 108 and 109.

The outer insert 107 having external threads 112 for attachment to the internal threads 111 of the nail stem 110, a tooling slot 137 to allow insertion of the dynamisation unit 103 into the nail stem 110 using a surgical screwdriver or similar instrument, and through-holes 130 and 131 to hold the upper and lower shear pin pairs 108 and 109.

The upper shear pin pair 108 having a uniform cross-section or having a groove or other stress concentrating feature at the sliding interface between the inner insert 106 and outer insert 107, depending on the desired threshold load limit for dynamisation from Phase I to Phase II as described above. Varying the diameter of the shear pins and/or the shape and size of the groove can be used to give a wide range of threshold loads for pin failure.

The lower shear pin pair 109 of the same or similar design as the upper shear pin pair 108, depending on the desired threshold load limit for dynamisation from Phase II to Phase III as described above.

The end cap 104 having a threaded end for attachment to the internal threads 111 of the nail stem 110, a smaller diameter end to interface with the inner diameter of the outer insert 107, and a tooling slot 138 to allow insertion into the nail stem 110 using a surgical screwdriver or similar instrument.

The motion assembly 103 preserves a central lumen 135 to allow the passage of a guide wire during the surgical procedure. The tapered proximal end of the inner insert 106 provides a smooth transition from the larger diameter of the nail stem lumen 136 to the smaller inner diameter of the dynamisation unit 103.

The motion assembly 103 allows controlled bone separation (micromotion) by limited freedom of movement of the inner insert 106 relative to the outer insert 107 as constrained by the upper shear pin pair 108 during Phase I or the lower shear pin pair 109 during Phase II. The load required to cause failure of the shear pins is determined by the size and cross-section of the shear pins and/or the shape and size of any stress-concentrating feature, so the shear pin characteristics can thus be tailored for a specific patient weight class. The surgeon is provided with a choice of motion assemblies, which are assembled, sterilised, and labelled according to patient weight. Before inserting the nail 100 into the patient, the surgeon chooses the appropriate motion assembly and secures it in the nail stem 110 by mating of the internal threads 111 in the nail stem 110 with the external threads in the motion assembly. The surgeon checks that the hole 116 in the inner insert 106 and the slot 101 in the nail stem 110 are aligned so as to freely accept the bone screw 115. This check may be accomplished by simply inserting the bone screw 115 through the nail 100 with the motion assembly 103 installed and adjusting the rotational position of the motion assembly 103 using a surgical screwdriver or similar instrument engaged in the tooling slot 137 in the outer insert 107. The surgeon may then proceed with the standard surgical procedure for inserting the nail 100 into the patient.

After surgery, the chain for interconnection of the proximal bone fragment to the distal bone fragment is as follows:

proximal bone screw 115;
inner insert 106;
upper shear pin pair 108 (if in Phase I) or lower shear pin pair 109 (if in Phase II);
outer insert 107;
nail stem 110, secured to the distal bone fragment at screw holes (not shown).

During the stance phase, the bone fragments tend to move together as the patient applies weight on the injured leg. During this phase, the distal bone fragment is considered fixed. The patient's body weight is transmitted through the proximal bone screw 115 to the inner insert 106, which slides downward relative to the shear pins 108 and 109. In Phase I, the upper slot 120 of the inner insert 106 bears downward on upper shear pin pair 108, which transmits the load to the outer insert 107. In Phase II, the lower slot 121 of the inner insert 106 bears downward on the lower shear pin pair 109, which transmits the load to the outer insert 107. The outer insert 107 is attached to the nail stem 110 via screw threads, so the load travels through the nail stem 110 to the distal bone screw(s)

and distal bone fragment. In Phase III, when all shear pins have failed, the inner insert 106 travels freely relative to the outer insert 107 until the bone screw 115 bears down on the bottom of the slot 101 in the nail stem 110.

During the swing phase, the bone fragments tend to move apart as the patient takes weight off the injured leg. During this phase, the proximal bone fragment is considered fixed. The combined weight of the foot and shank pulls downward on the distal bone screw(s) and this load is transmitted to the nail stem 110 and the outer insert 107 via the screw threads 111 and 112. In Phase I, the outer insert 107 and both shear pin pairs 108 and 109 translate downward until the pins bear down on the slots 120 and 121 in the inner insert 106. In Phase II, after the upper shear pins 108 have failed, only the lower shear pins 109 bear down on the lower slot 121 in the inner insert 106. The foot and shank weight is thus transmitted through the pins, the inner insert 106, and the bone screw 115 to proximal bone fragment. In Phase III, when all shear pins have failed, the outer insert 107 travels freely relative to the inner insert 106 until the bone screw 115 bears upward on the top of the slot 101 in the nail stem 110.

This embodiment facilitates several improvements including some or all of allowing axial interfragmentary micromotion to stimulate callus formation at the fracture site and accelerate healing (Phase I functionality), controlling the interfragmentary displacement in both the stance and swing phases, allowing for non-surgical post-operative adjustment of bone separation distance, or dynamisation (Phases II/III functionality), and/or achieving the aforementioned improvements while maintaining the torsional and bending rigidity of a standard IM nail.

The following describes other aspects of the illustrated embodiments and various alternative embodiments.

In one embodiment, the nail may include a plurality of slots or other fixture holes in the proximal end to accommodate a plurality of bone screws or other fixtures. The slots or fixture holes may be arranged in a single plane or in a series of oblique planes rotated about the longitudinal axis of the nail. The inner insert may contain a plurality of through-holes for a plurality of bone screws or other fixtures aligned with the slots in the proximal end of the nail.

In one embodiment, the dynamisation unit may be attached to the nail stem by screw threads or by one or a plurality of pins or other fasteners positioned in slots, holes or openings in the proximal end of the nail, which has been shown in simplified form in FIGS. 15 to 17, for illustrative purposes only.

In one embodiment, the nail may be cast, machined, or otherwise formed so as to include any or all of the features of sub-components described (including but not limited to the outer insert and shear pins) as an integrated single part while achieving the same or similar functionality.

In one embodiment, the dynamisation unit may be mounted in the distal end of the nail to achieve the same or similar effects as described in any other embodiment herein.

In one embodiment, the shear pins may comprise a non-circular cross-section, including but not limited to any n-sided prismatic polyhedron, or any elliptic, parabolic, or hyperbolic cylinder. The shear pins may be symmetric or asymmetric about any axis and may comprise a combination of cross-sections. The pins may also take the shape of a parallel, gib head, tapered, or woodruff key, or any other demountable machinery part that may be assembled into a keyseat or other receiving slot to provide a positive means of transmitting force between two components. These keys may also be used to provide rotational alignment of the insert and stem and additional torsional stability. The pins may or may not contain stress-concentrating features such as grooves, notches, depressions, divots, or step-changes in geometry. The pins may be formed from one piece of material machined or otherwise shaped to give the desired shape, or they may be formed of a plurality of pieces and or materials joined together to form the desired shape.

In one embodiment the surface of the inner insert 106 may incorporate two flat areas to facilitate a perpendicular shearing interface relative to the shear pins 108. This will result in a more uniform loading through the dynamisation phases I-III.

In one embodiment, the bone fragment separation distance (micromotion) facilitated in Phase I may be altered to any distance desired by changing the length of the upper slot 120 in the inner insert 106.

In one embodiment, the bone fragment closure distance (partial dynamisation) facilitated in Phase II may be altered to any distance desired by changing the length of the lower slot 121 in the inner insert 106.

In one embodiment, the invention may comprise more than two shear pin pairs to achieve a plurality of micromotion/dynamisation phases for non-surgical adjustment of bone separation distance. The plurality of pin pairs may be of the same or similar design and may be arranged in a single plane or in a series of oblique planes rotated about the longitudinal axis of the nail.

In one embodiment, dynamisation may be achieved by the patient bearing weight statically or by impact loading, with or without assistance from the surgeon or another person, or by any other means of generating a sufficient force component directed along the longitudinal axis of the nail so as to achieve failure of one or more shear pin pairs.

In one embodiment, the shear pins may be encapsulated within or inserted into a bearing sleeve comprised of a viscoelastic, hyperelastic, rubber, or other energy-absorbing material to cushion the impact of the pins on their bearing surfaces in the slots and in the inner insert. In a further embodiment, the energy-absorbing material may be affixed to the bearing surfaces of the inner insert.

In one embodiment, the shear pins may be press-fit, welded, threaded, or otherwise rigidly affixed to the outer insert to achieve pin fragment control after dynamisation (Phases II and III).

In one embodiment, a biocompatible radiopaque material, including but not limited to platinum or tantalum, may be embedded in or attached to one or more components previously described in order to determine their position relative to one another, the bone screw(s), or the IM nail.

In one embodiment, the device may also comprise an integrated electronic or magnetic sensor or indicator to detect or measure axial movement within the device (e.g. interfragmentary motion, micromotion, dynamisation), which may be indicative of fracture healing or other clinically-relevant outcome.

Figure 18:
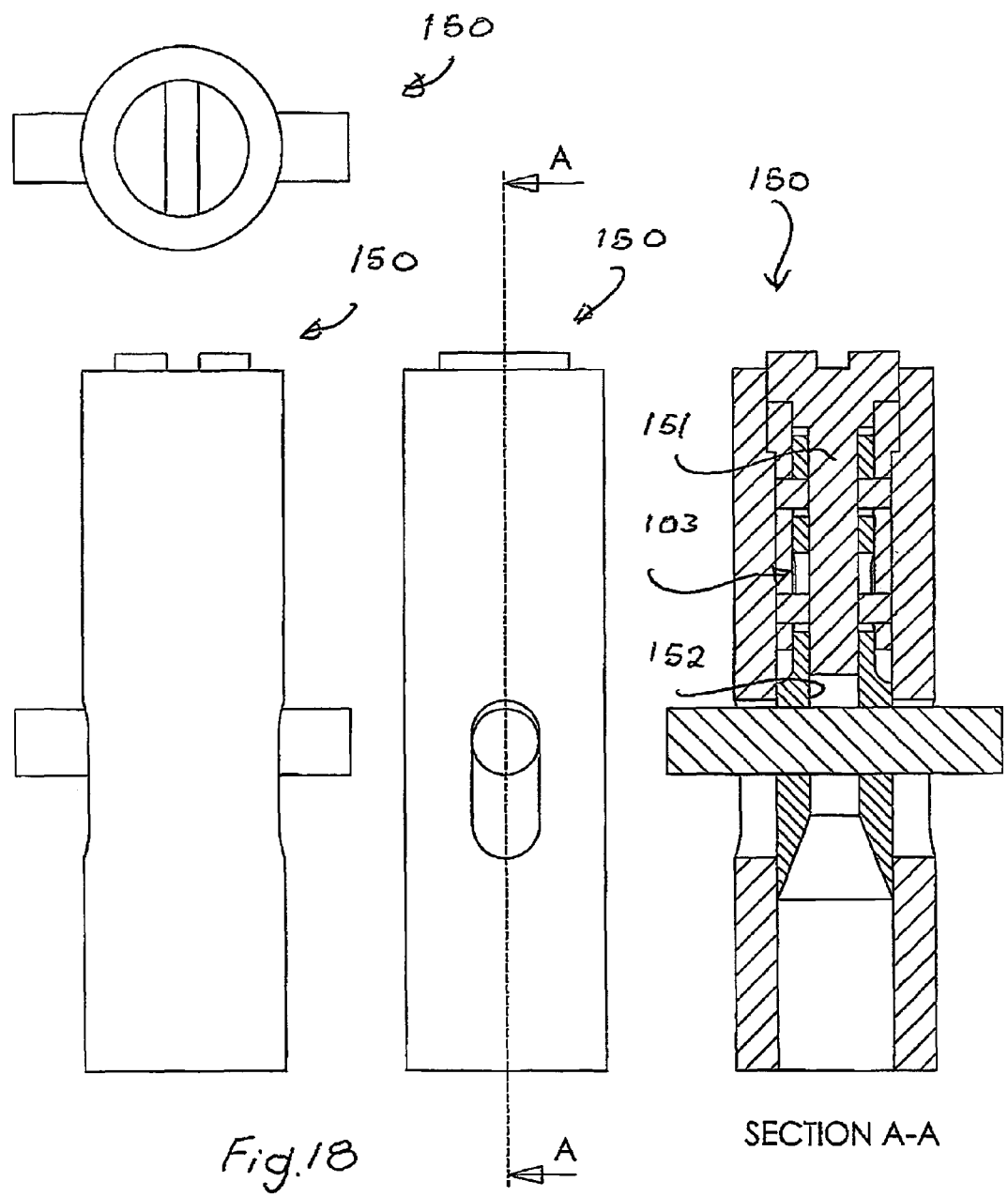
FIG. 18 is a set of views showing a variation on the embodiment of FIG. 15 in which the end cap is extended to form a plug filling the central lumen of the nail.

In one embodiment, a nail 150 has an end cap 151 extended as illustrated in FIG. 18, to form a plug for the central lumen 152 of the dynamisation unit 103, so that shear pin fragments generated during the transition from Phase I to Phase II/III are prevented from falling into the central lumen of the dynamisation unit.

In a further embodiment, the lumen plug may comprise a component inserted into the device separately from the end cap and threaded or otherwise secured to the inner insert and/or the outer insert, and/or the subsequently-attached end cap. In a further embodiment, the lumen plug may be an integrated feature of any existing component to achieve the same or similar functionality.

Figure 19:
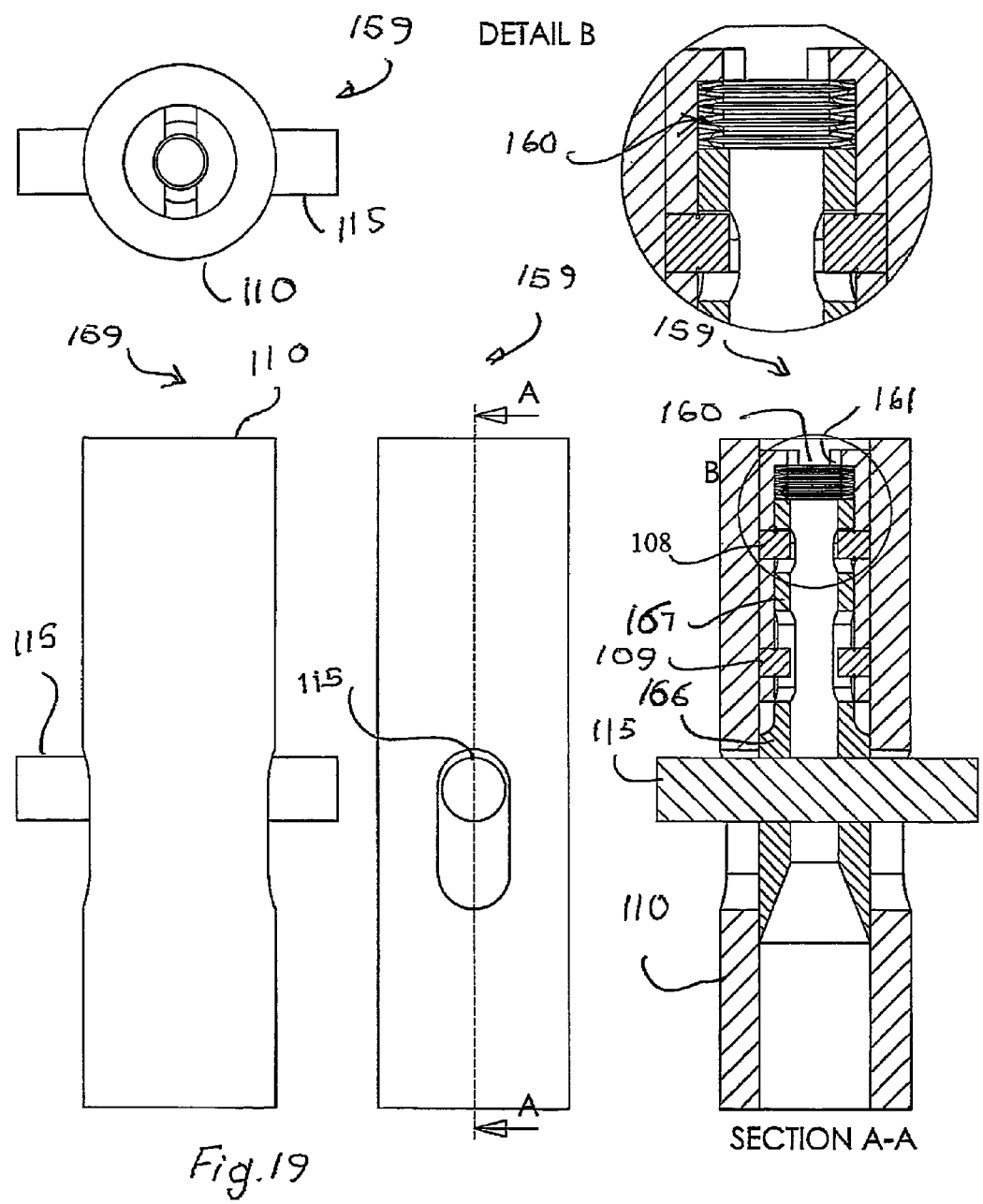
FIGS. 19 and 20 show a variation in which Belleville washers are added to control swing-phase micromotion.
Figure 20:
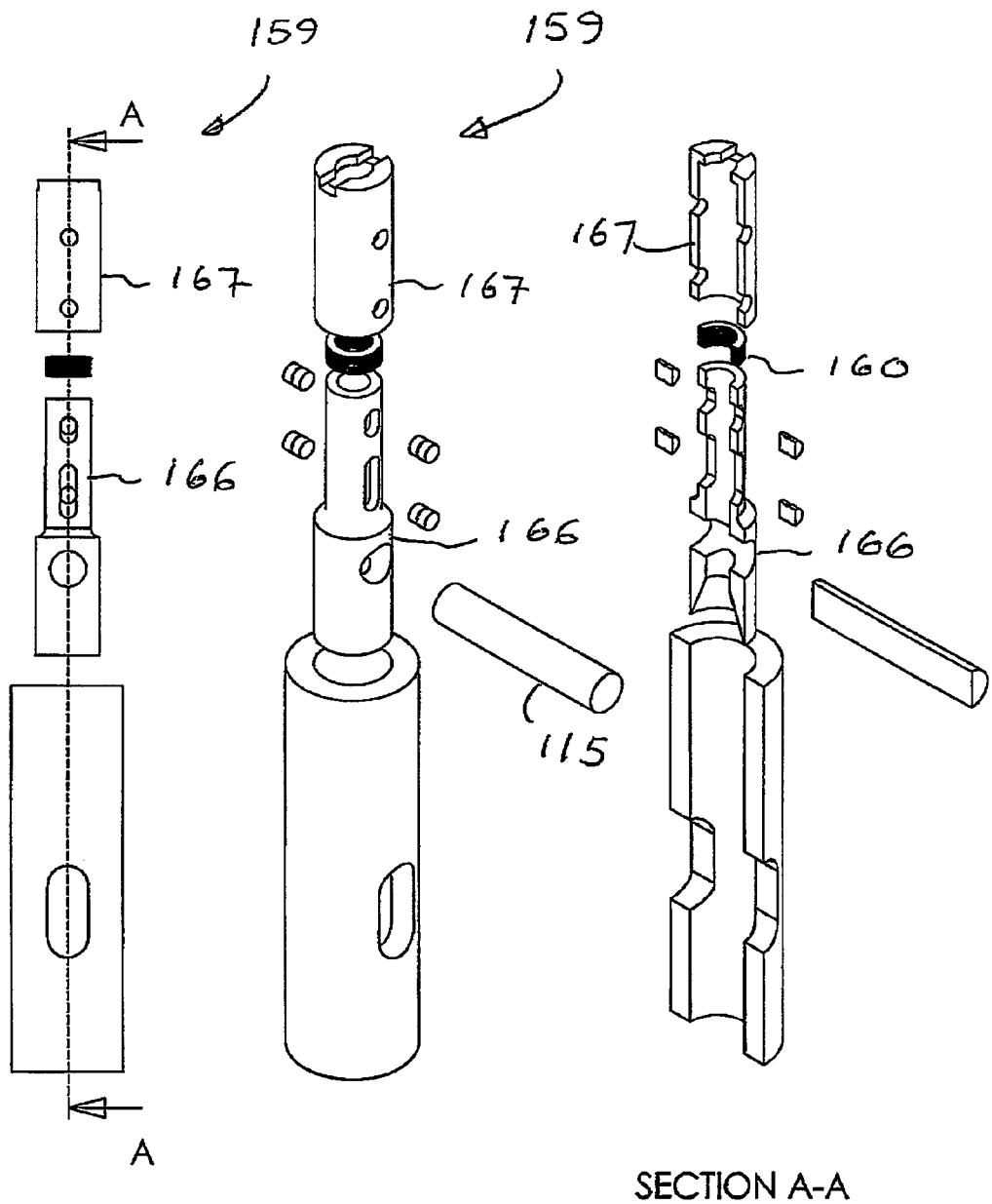

In one embodiment a nail 159 (FIGS. 19 and 20) has a Belleville washer or a plurality of Belleville washers 160 located between an inner insert 166 and the outer insert 167. The Belleville washers 160 are constrained between the top surface of the inner insert 166 and an added lip 161 on the top edge of the outer insert 167. The Belleville washers 160 compress during the swing phase when the weight of the shank and foot cause the nail stem 110, outer insert 167, and shear pins 108 and 109 to translate downward relative to the proximal bone fragment, bone screw 115, and inner insert 166.

Figure 21:
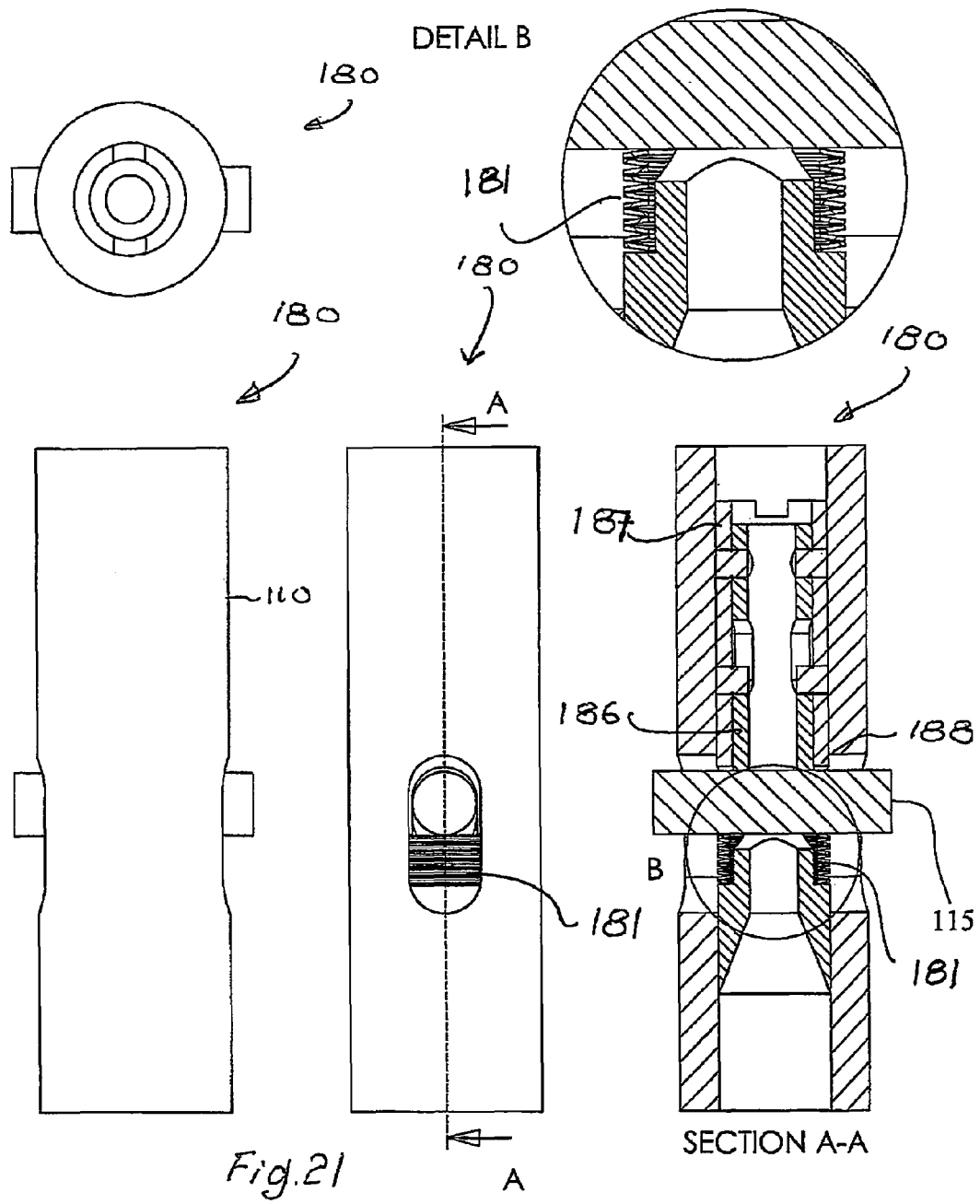
FIGS. 21 and 22 show a variation in which Belleville washers are added to control stance-phase micromotion.
Figure 22:
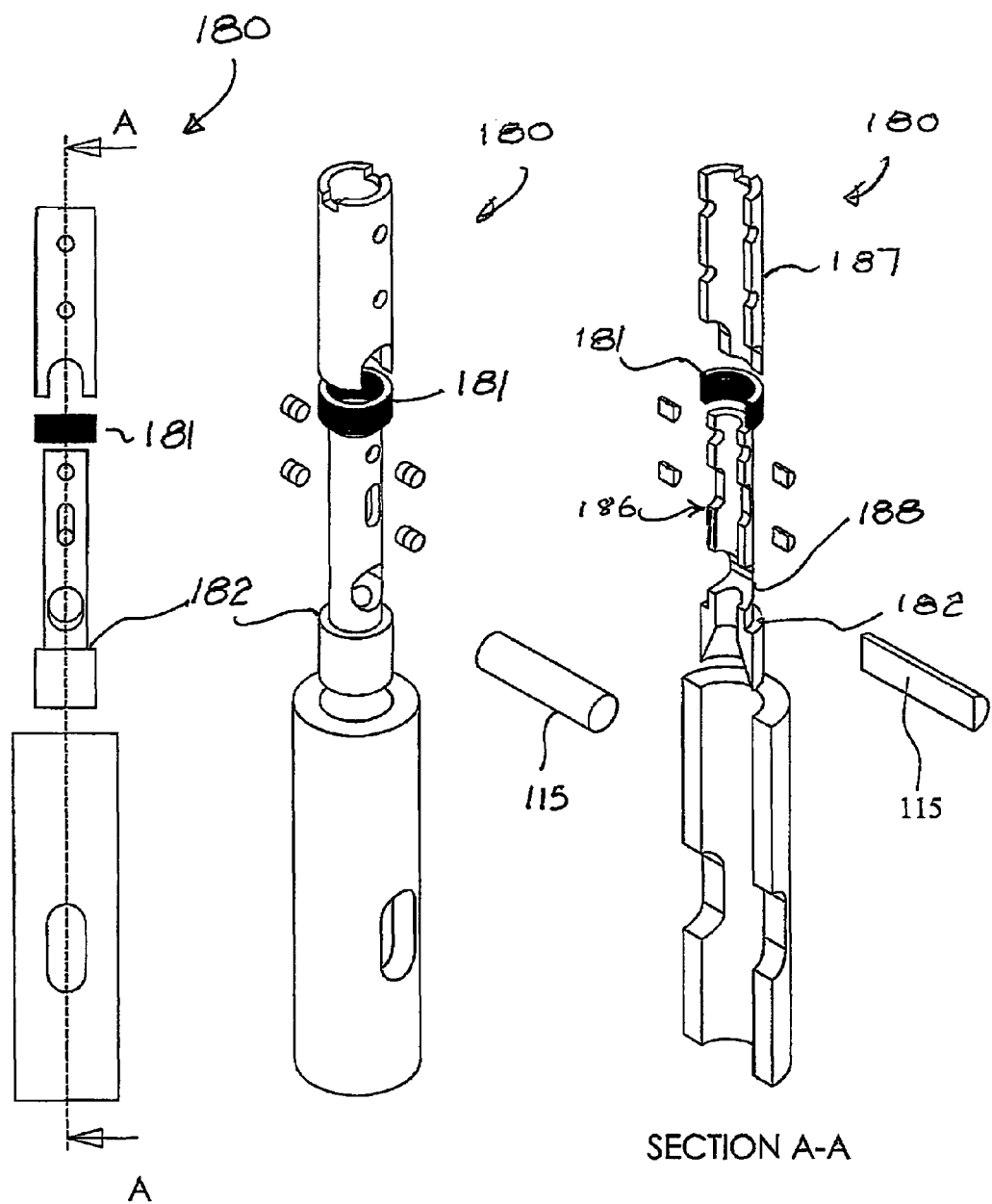

In a further embodiment (FIGS. 21 and 22) in a nail 180, a Belleville washer or a plurality of Belleville washers 181 may be added between the bone screw 115 and an inner insert 186 to provide damped micromotion. The Belleville washers are seated on a bearing lip 182 of the inner insert, which is then inserted into an outer insert 187 and secured by the shear pins 108 and 109 to form the pre-assembled dynamisation unit. The dynamisation unit is inserted into the nail stem 110, which is then implanted in the patient as previously described. There may or may not be a spacer ring, flat washer, or other insert positioned on top of the stack of Belleville washers 181 to maintain their position during insertion of the bone screw 115. The bone screw passes through a slot 188 in the inner insert 186 to allow micromotion. During the stance phase, the patient's weight is transmitted by the bone screw 115 through the Belleville washers 181 to the inner insert 186. As the Belleville washers 181 compress, the bone screw 115 translates downwards until it bears on the bottom of the slot 188 in the inner insert 186. Then the load is transmitted from the inner insert 186 through the shear pins 108 and 109 to the outer insert 187 and the nail stem 110 as described previously.

In a further embodiment, damped micromotion may be achieved by one or a plurality of energy storage elements arranged in any series or parallel combination, including but not limited to Belleville washers, coned-disc washers, wave washers, slotted washers, finger washers, split washers, curved washers, volute springs, or coil springs (standard, variable pitch, barrel, hourglass, or conical).

In one embodiment, (FIGS. 23 and 24), in a nail 200 micromotion and dynamising functionality may be achieved through a two-part assembly during the surgical procedure. The nail 200 is prepared for insertion into the patient according to the standard operative technique. An insertion handle is attached to the nail 200 via a standard insertion bolt (not shown for simplicity), which has been modified to allow an anchor 206 to thread or press onto the end of the insertion bolt. The anchor 206 has a central lumen to accommodate a guide wire and a tapered end to aid passage of the guide wire from the larger diameter of the nail lumen through the anchor 206. The surgeon checks the alignment of a hole 207 in the anchor 206 relative to a slot 220 in the nail stem 210 and turns the insertion bolt to make any necessary rotational adjustments before inserting the nail 200 into the intramedullary canal. After the nail has been implanted in the patient, the distal bone screw(s) are inserted and a bone screw 115 is inserted through the proximal bone fragment, the slot 220 in the nail 200, and the hole 207 in the anchor 206. The insertion bolt and insertion handle are then removed. Another component of the dynamisation unit comprises a pre-assembled module containing a modified end cap 216, a shear pin 221, and a slider 209. This module is threaded simultaneously into both the internal threads 211 in the proximal end of the nail stem 210 and the internal threads 208 in the anchor 206. The dynamisation unit may contain a single shear pin 221 for dynamisation or a plurality of shear pins. When the patient bears weight, the load is transmitted from the bone screw 115 through the anchor 206 to the shear pin 221 and the slider 209. As the top of the slot 215 in the slider 209 bears down on the shear pin 221 and the load is transmitted through the modified end cap 216 to the nail stem 210 and the distal bone fragment. The embodiment may also contain a Belleville washer or a plurality of Belleville washers 201 to provide damped micromotion in the swing phase.

In any embodiment previously described, the correct rotational alignment of the parts (including but not limited to the pre-assembled dynamisation unit relative to the nail) may be achieved by one or more hard-stops and may or may not be accompanied by one or more audible clicks to signify to the surgeon that the device is properly inserted.

Figure 25:
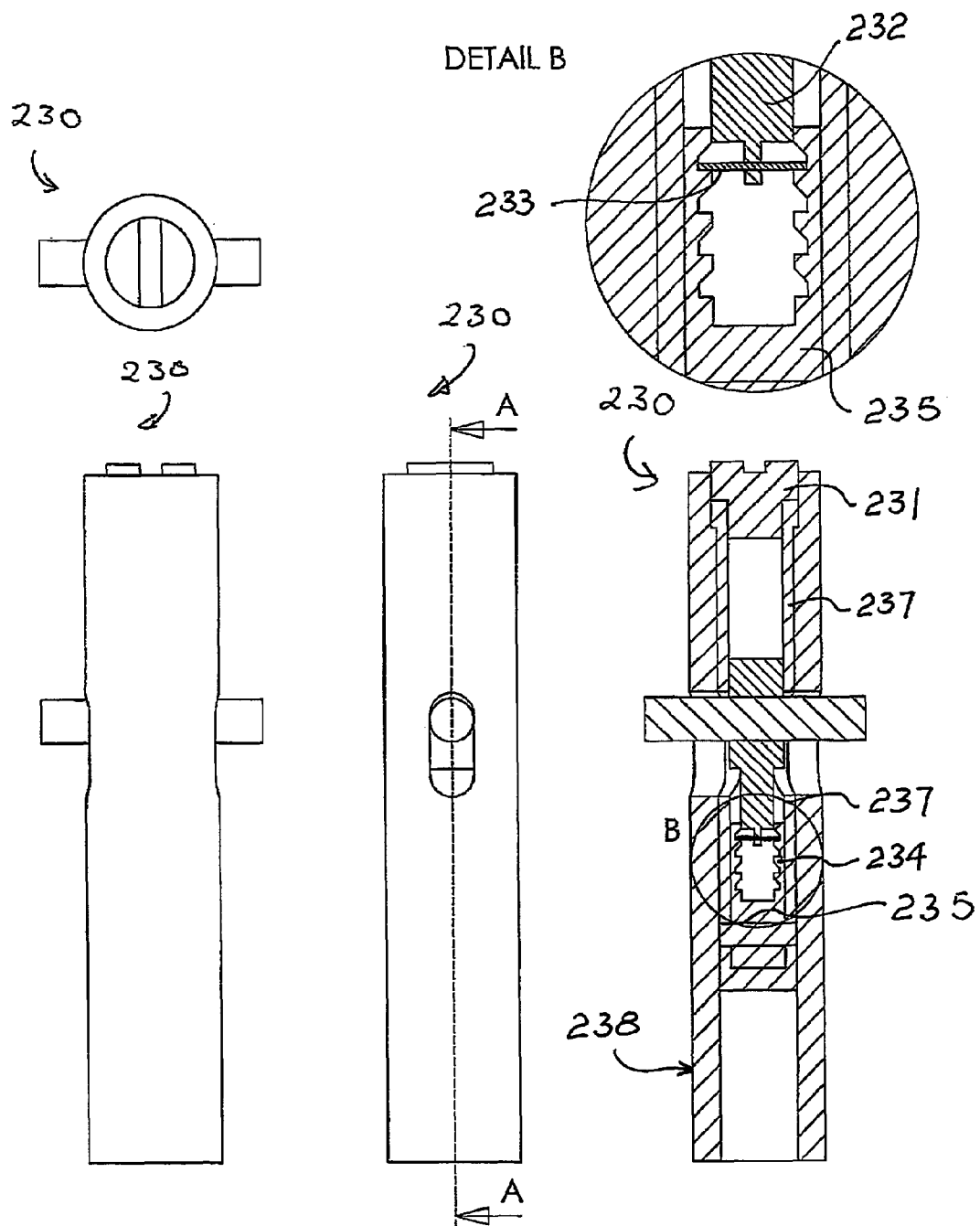
FIGS. 25 to 39 are views in the same general formats of still further embodiments.
Figure 26:
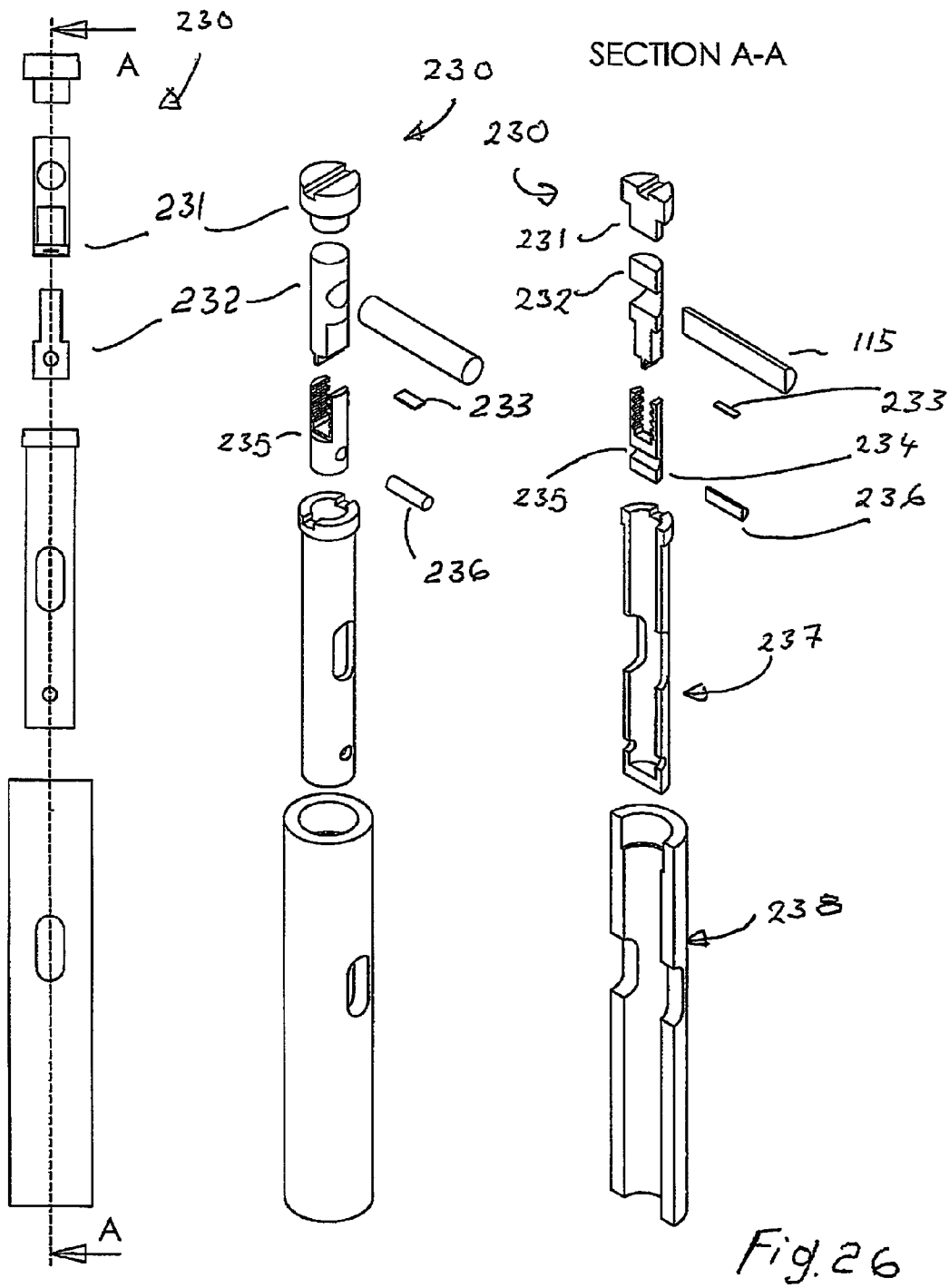

In another embodiment (FIGS. 25 and 26) in a nail 230, the micromotion and dynamisation functionalities of the invention are achieved via a beam-ratchet mechanism. Initially, a beam 233 or energy storage element rests on the bearing surface of the uppermost ratchet as shown. The beam 233 passes through a slot in a slider 232 to admit micromotion. If the patient applies sufficient weight, the beam 233 snaps downwards to the next ratchet increment, bringing the bone fragments closer together. The load at which the beam 233 will progress to the next increment is determined by the beam 233 cross section (constant or non-constant), initial shape (flat or curved), and material properties. The beam may also comprise a plurality of beams such as a leaf spring. A ratchet 234 profile, including the angle, depth, width, spacing, and orientation of bearing surfaces and sliding surfaces shown in FIGS. 25 and 26 is given for illustrative purposes only to represent a series of grooves that differentiate unique ratchet increments for bone separation distance control. In this embodiment, the rotational orientation of the ratchet-beam-slider sub-assembly is controlled relative to the insert sleeve 237 by a pin 236. After the nail is implanted in the patient and locked distally, the insert sleeve 237 is threaded into the proximal end of the nail stem 238. The proximal bone screw 115 is then inserted and an end cap 231 is screwed into the nail stem 238 and/or the insert sleeve 237.

Figure 27:
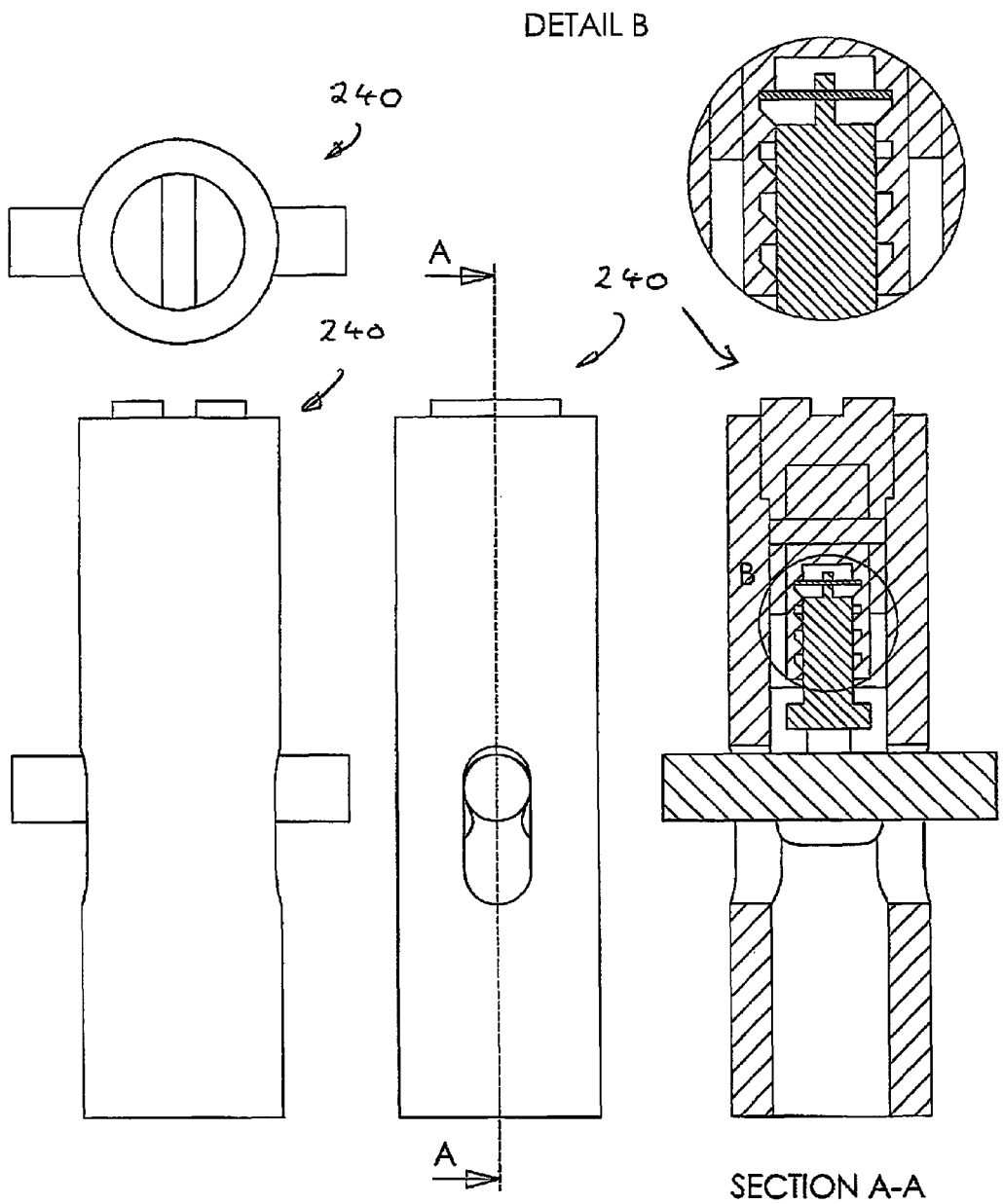
Figure 28:
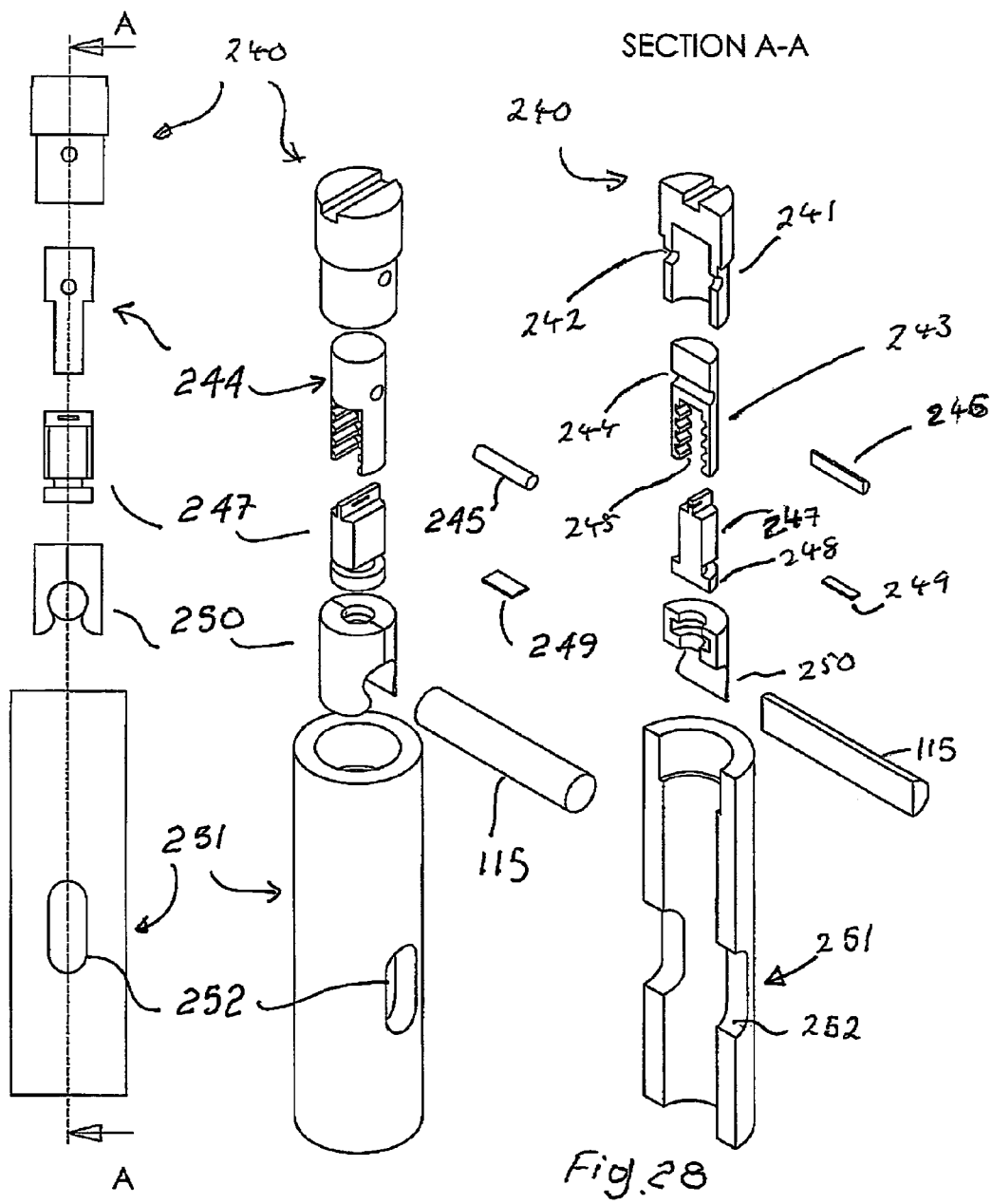

In a further embodiment (FIGS. 27 and 28), in a nail 240 the beam-ratchet mechanism illustrated in FIGS. 25 and 26 is inverted and positioned above the bone screw 115 to accommodate a different operative technique. In this instance, the complete dynamising unit is pre-assembled and comprises the following components. A beam 249 spring element passes through a slot in a slider 247 and is initially positioned in an uppermost groove 245 of a ratchet 243. The slider-beam-ratchet unit is then affixed by a pin 245 or otherwise mounted inside a modified end cap 241. Two identical curved grips 250 are mounted on the circular bearing lip 248 of the slider 247 and the grips are pinned or otherwise fastened together (not shown for simplicity). Thus, the grips 250 have rotational freedom relative to the end cap 241. During the operation, the surgeon implants the nail as normal and inserts bone screws in the distal holes and proximal slot. The dynamising unit is threaded into the proximal end of the nail stem 251 and curved grips 250 snap onto the bone screw 115 in a proximal slot 252.

Figure 23:
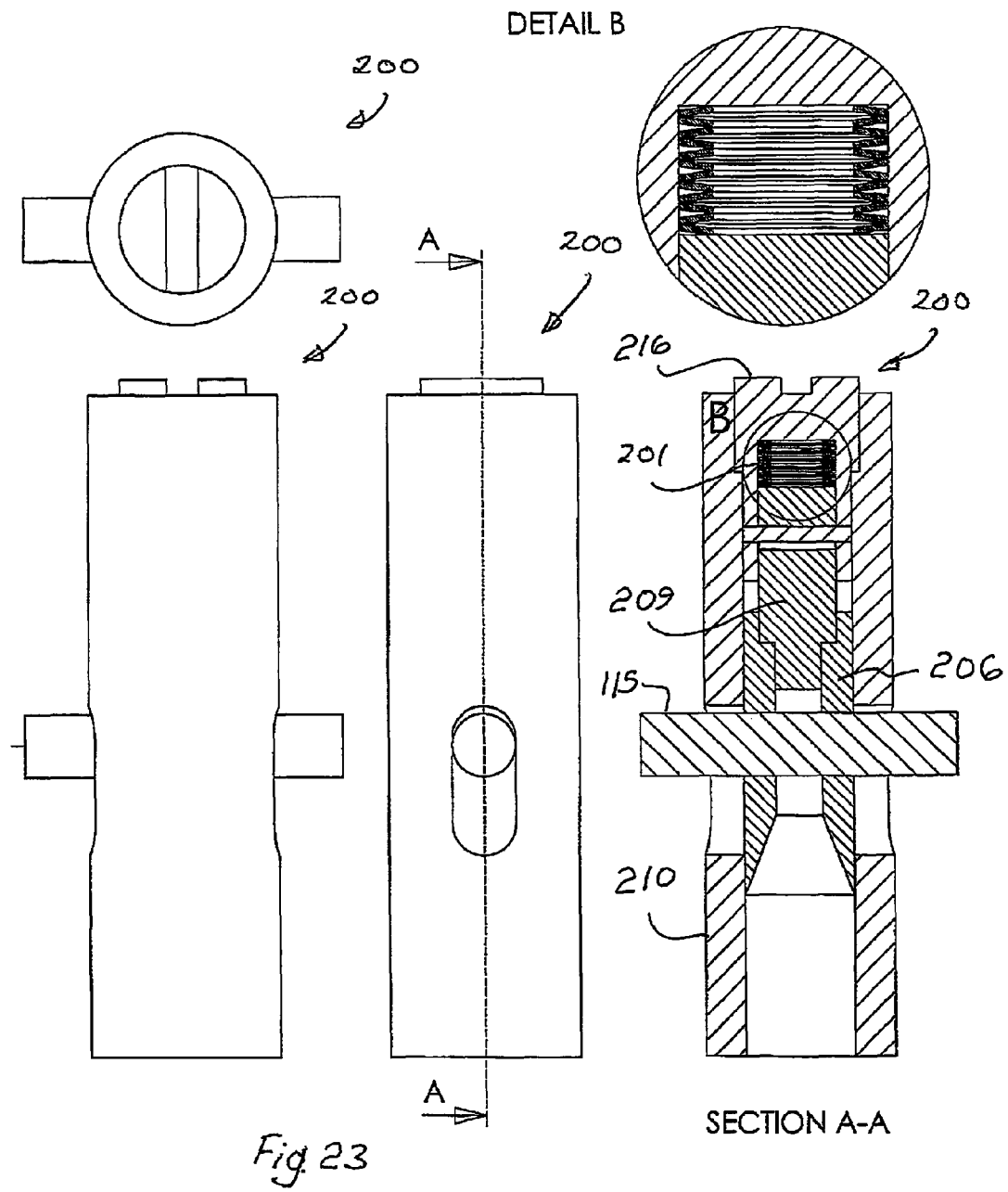
FIGS. 23 and 24 show a variation on the embodiment of FIG. 15 in which the device is comprised of an anchor part, positioned inside a nail central lumen before the nail is implanted into the patient via attachment to an insertion handle used in a standard operative technique, and a modified end cap that mates with the anchor and is inserted after the nail is implanted.
Figure 24:
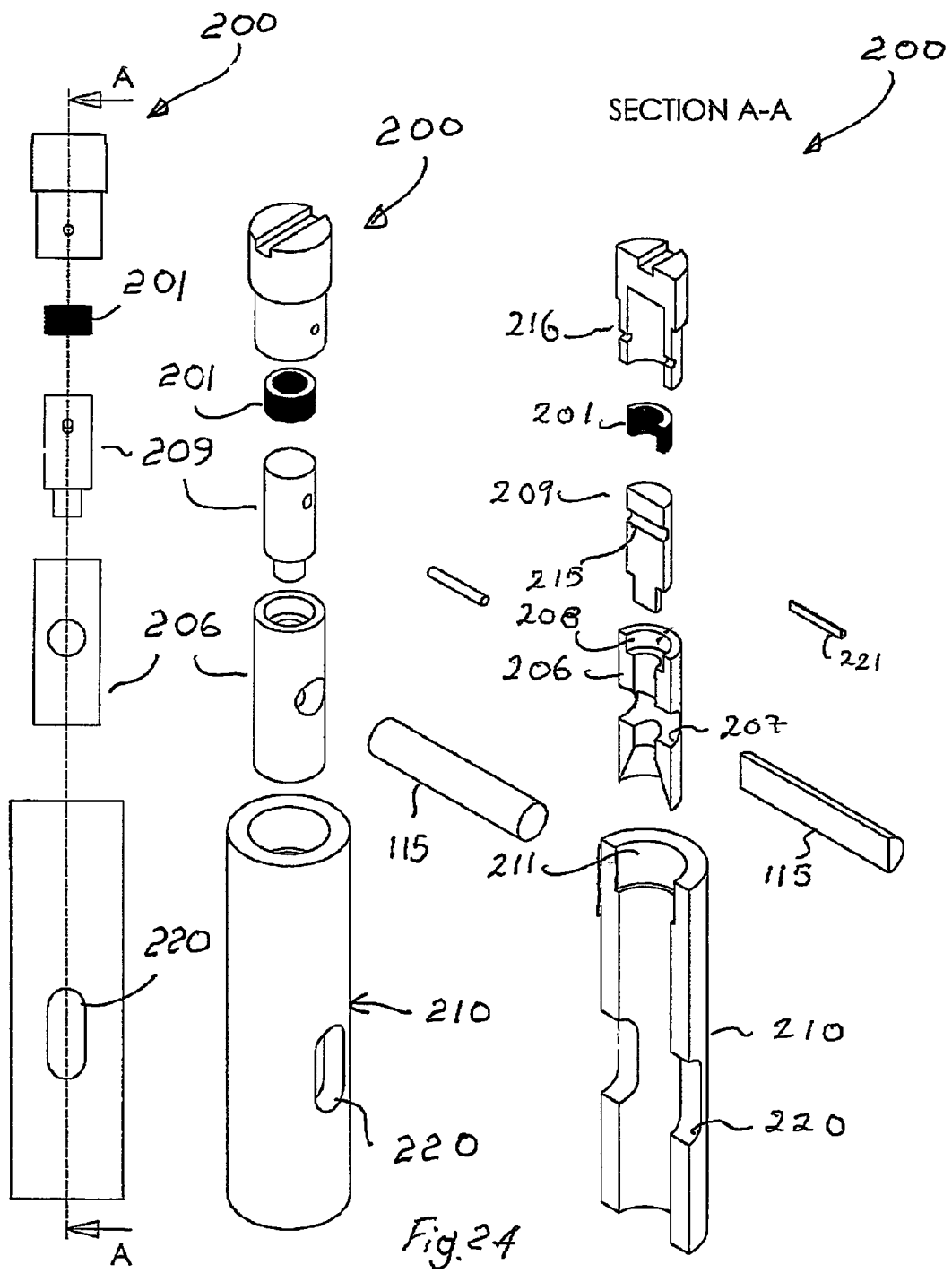
Figure 29:
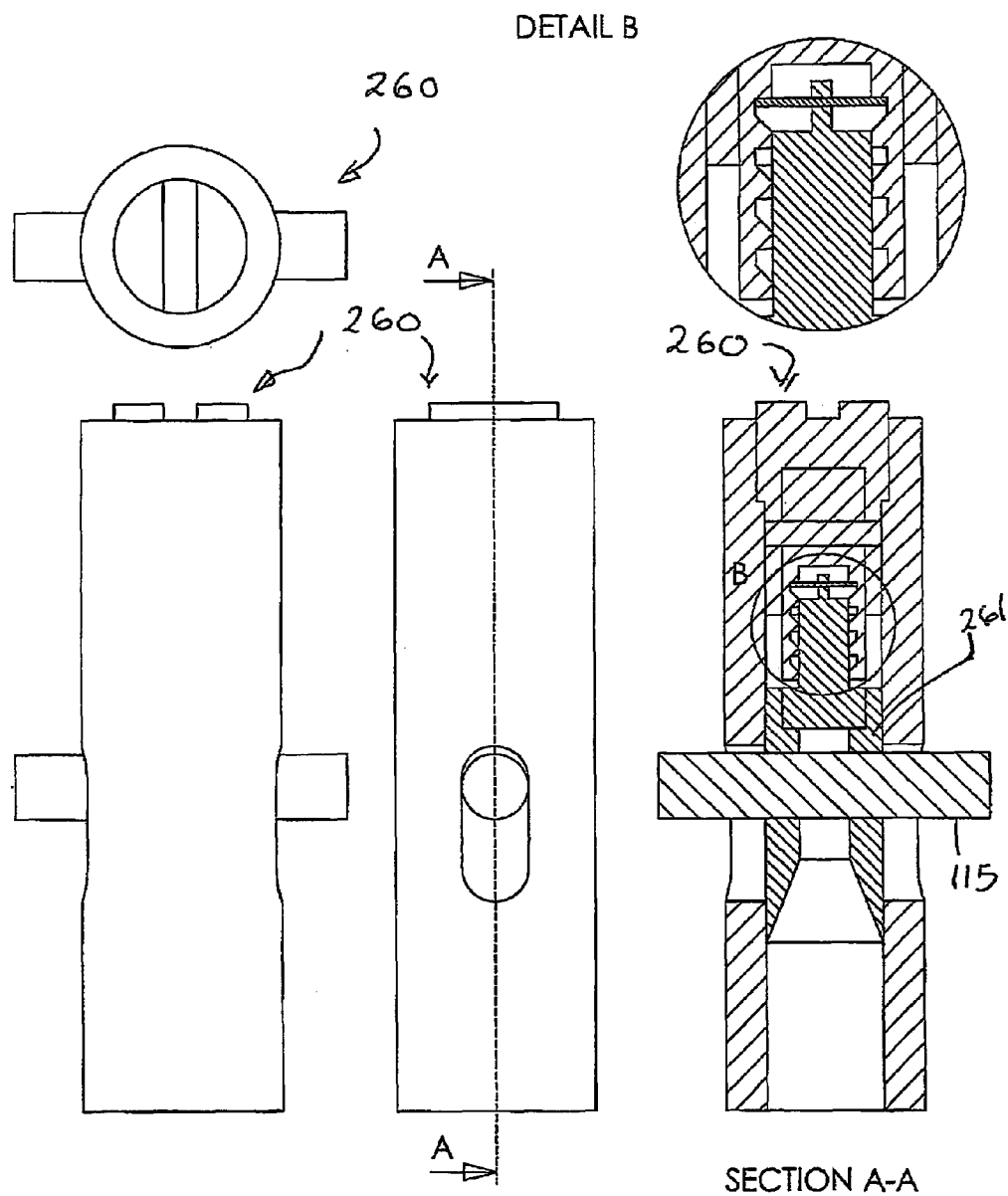

In a further embodiment (FIG. 29), the beam ratchet mechanism illustrated in FIGS. 25 to 28 is assembled inside the nail through a two-part assembly similar to the procedure described for FIGS. 23 and 24. In short, an anchor 261 is initially attached to an insertion bolt until the proximal bone screw 115 is inserted. Then the insertion handle and bolt are removed, leaving behind the anchor 261. The dynamisation unit is then simultaneously threaded into the proximal end of the nail and the anchor 261. In this way, connectivity is achieved between the proximal and distal bone fragments.

Figure 30:
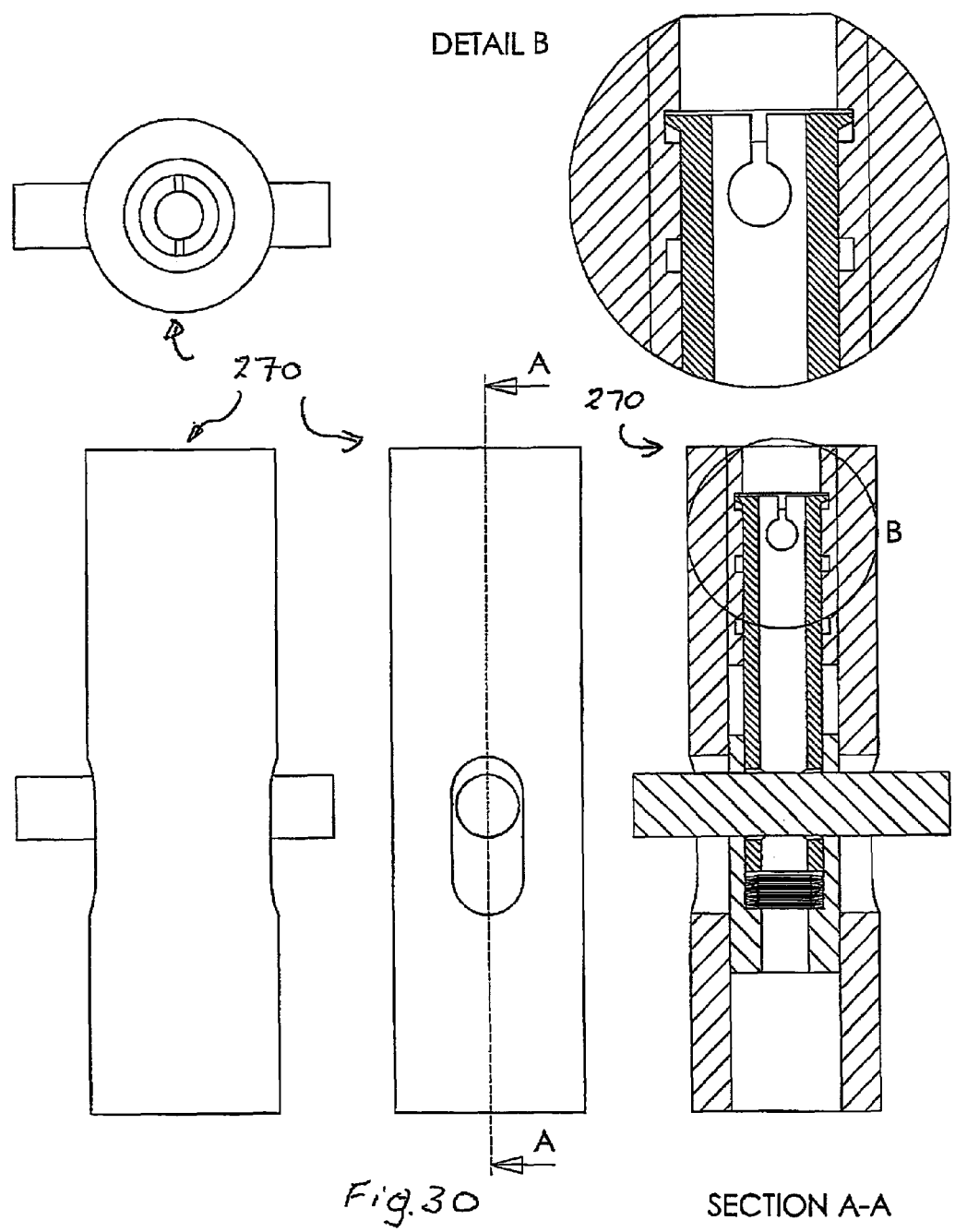
Figure 31:
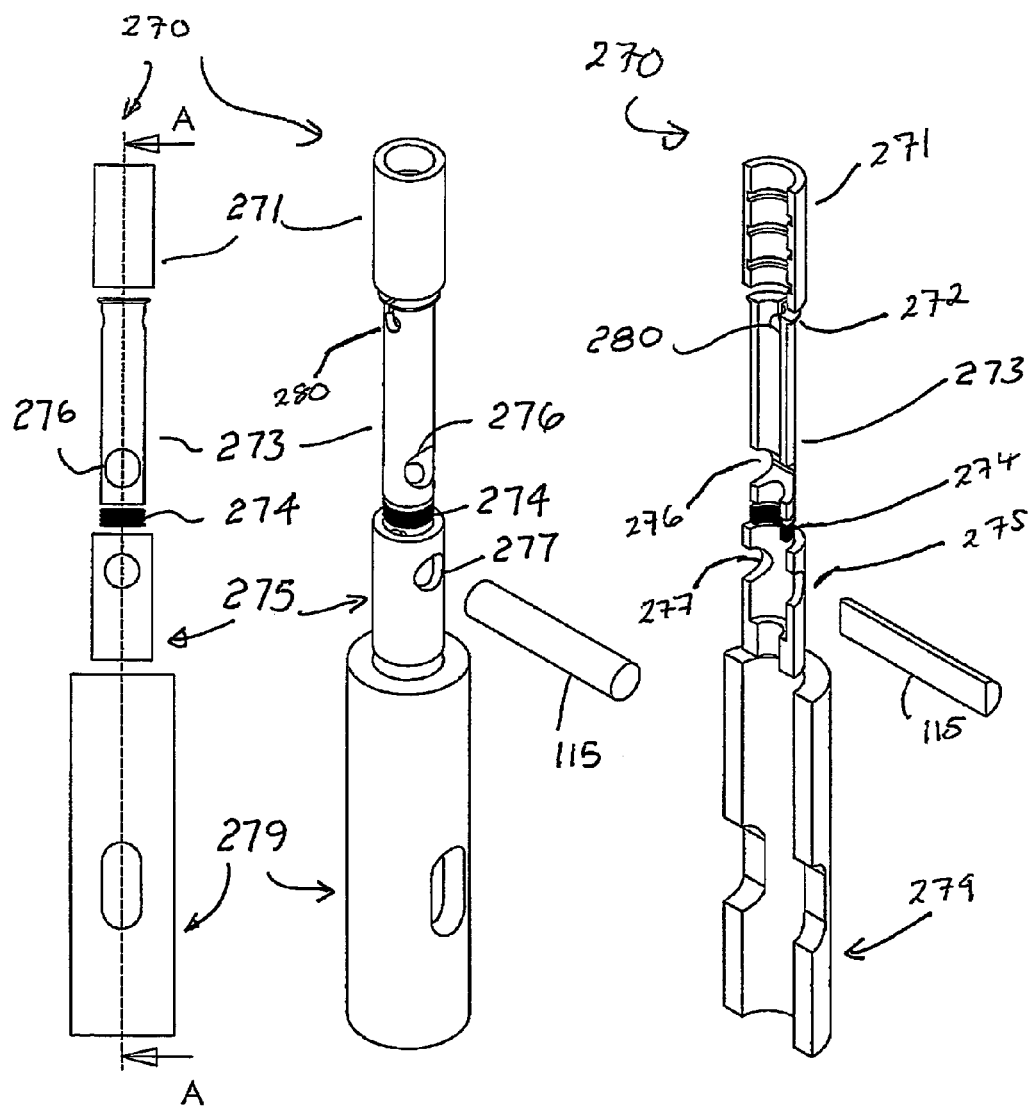

In a further embodiment (FIGS. 30 and 31), in a nail 270 the ratchet mechanism is integral with a slider 273. The ratchet grooves are contained in an upper sleeve 271 and are shown here with a square cross-section for illustrative purposes only to represent a series of grooves that differentiate unique ratchet increments for bone separation distance control. The upper sleeve 271 attaches to a nail stem 279 via screw threads, pins, or other rigid fixation not shown in this illustration for simplicity. The top of the slider 273 has a tapered lip 272 that initially engages in the uppermost ratchet groove. The top of the slider 273 is also formed with a keyhole 280 or other cutout to allow the slider 273 to flex and snap from one ratchet position to the next. In this embodiment, a plurality of Belleville washers 274 is included between the lower sleeve and the slider. The bone screw 115 passes through a hole 277 in the lower sleeve 275 and a slot 276 in the slider 273 to admit micromotion. As the patient applies weight, the Belleville washers 274 deform and the bone screw 115 bears down on the bottom of the slot 276 in the slider 273. If the patient applies sufficient weight, the slider 273 progresses downwards to the next ratchet position, carrying with it the lower sleeve 275, the Belleville washers 274, and the bone screw 115 to close the gap between the proximal and distal bone fragments. In this embodiment, the functionality of the Belleville washers 274 is preserved at all ratchet positions.

Figure 32:
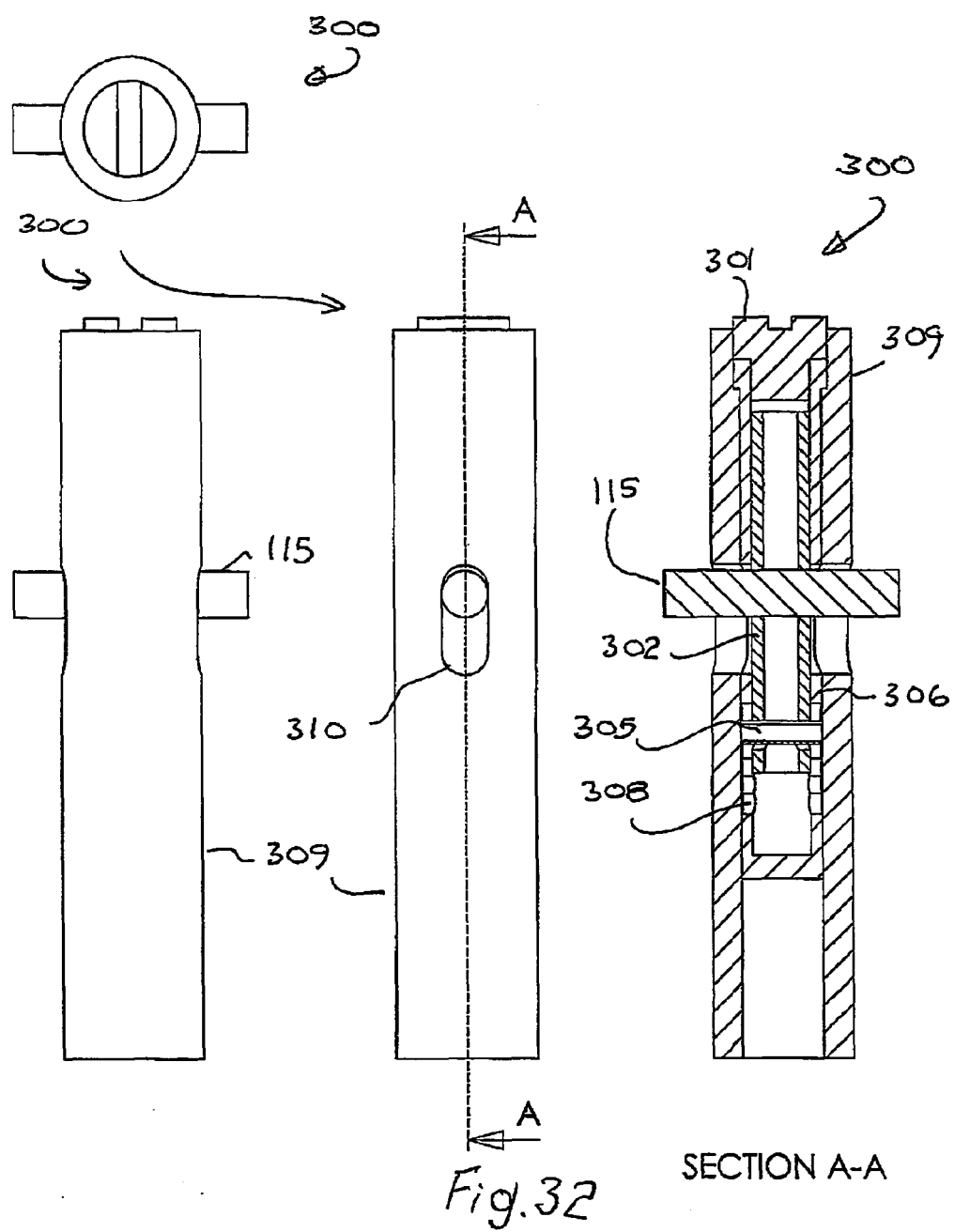
Figure 33:
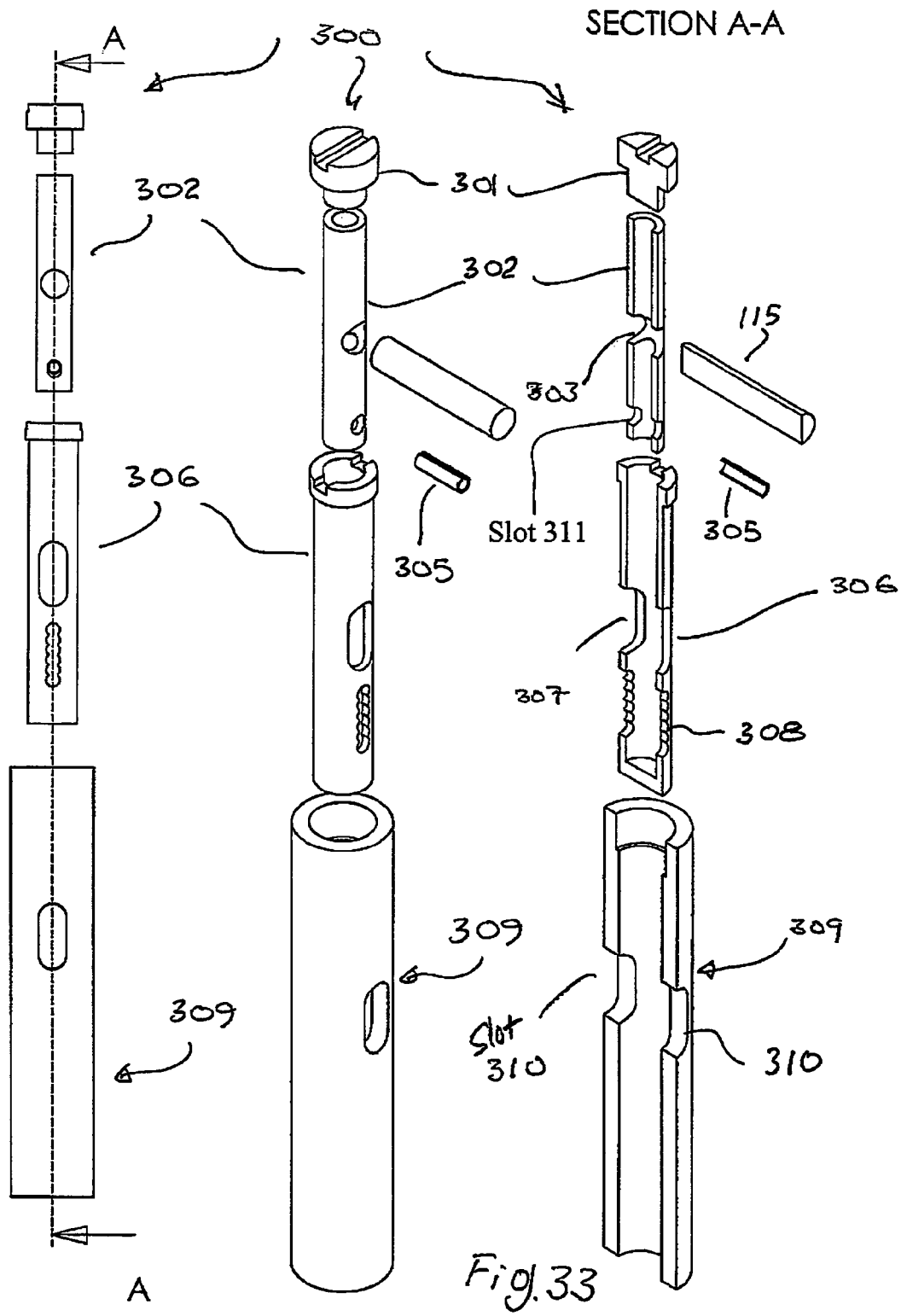

In one embodiment (FIGS. 32 and 33), in a nail 300 a ratchet mechanism comprises a spring pin, split pin, or roll pin engaged in a series of through-holes. A pre-assembled dynamisation unit comprises an outer insert 306, an inner insert 302, and a spring pin 305. The spring pin 305 initially passes through an uppermost through-hole 308 in the outer insert 306 and a slot 311 in the inner insert 302 to admit micromotion. The dynamisation unit attaches to a nail stem 309 via screw threads, pins, or other rigid fixation not shown in this illustration for simplicity. The bone screw 115 passes through slots 310 and 307 in the nail stem 309 and outer insert 306 and the hole 303 in the inner insert 302. When the patient applies weight, the load is transmitted from the bone screw 115 to the inner insert 302 which bears down on the spring pin 305 and transmits the load to the outer insert 306 and the nail stem 309. If the patient applies sufficient weight, the spring pin 305 will snap down to the next ratchet position, carrying with it the inner insert 302 and the bone screw 115 to close the gap between the proximal and distal bone fragments. The spacing and profile of the through-holes 308 comprising the ratchet are given by way of example only to represent a series of unique ratchet increments for bone separation distance control.

Figure 34:
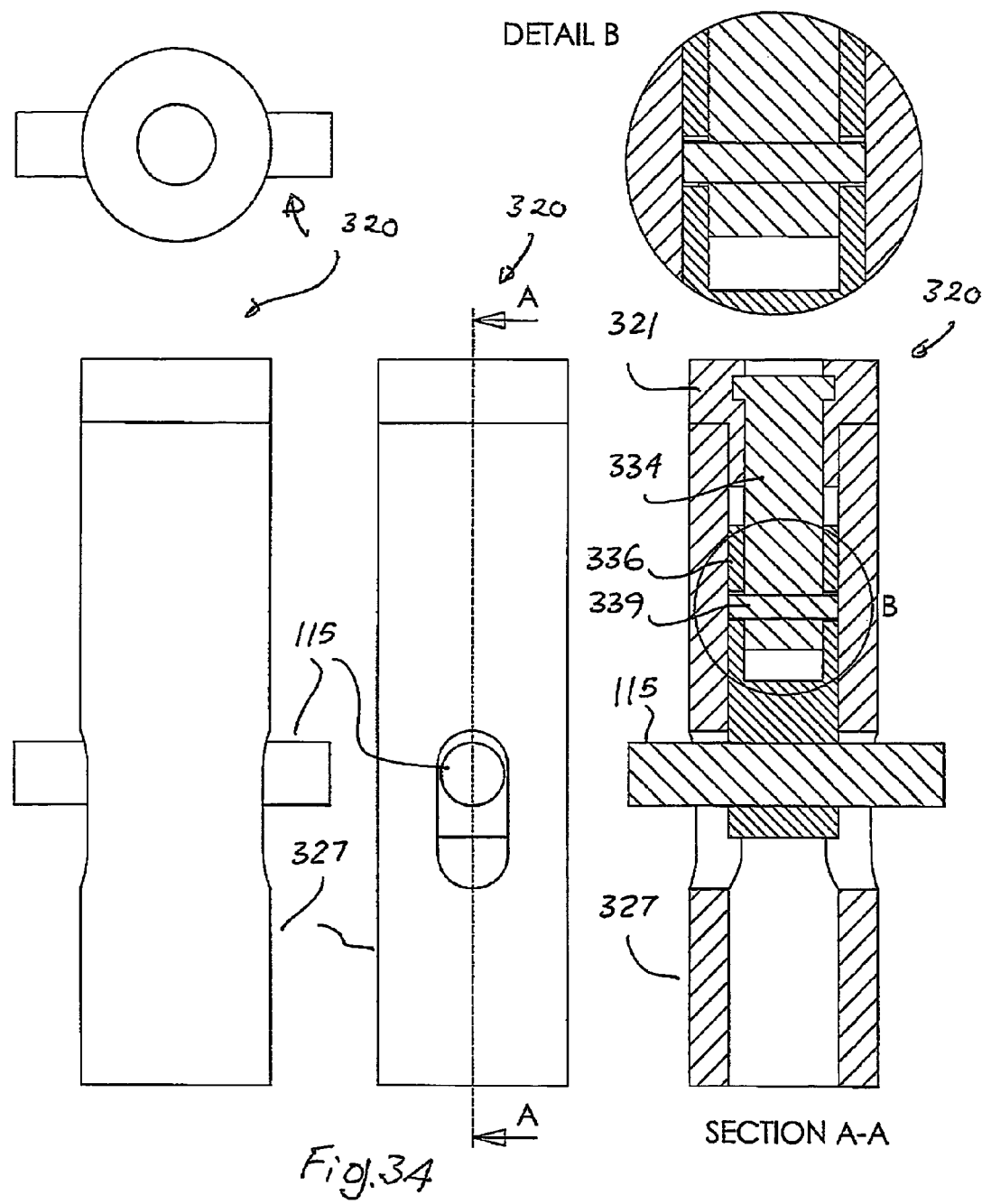
Figure 35:
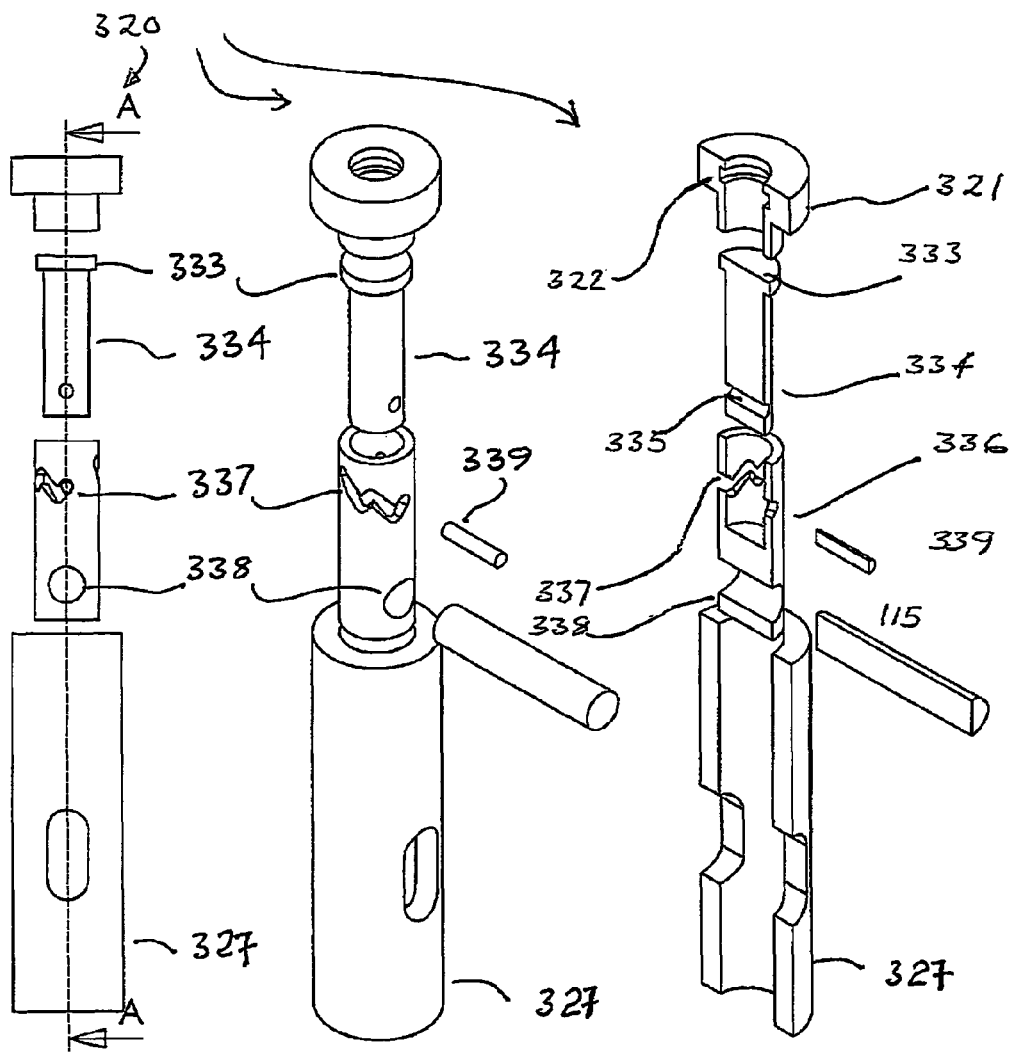

In one embodiment (FIGS. 34 and 35), in a nail 320 a bone separation control mechanism is comprised of a direction-reversing spiral ratchet with the following components. The bone screw 115 passes through a hole 338 in a sleeve 336, which is attached to an insert 334 by a pin 339 that initially rests in the rightmost recess of a spiral ratchet groove 337 in the sleeve 336. A lip 333 of the insert 334 rests in a bearing 322 of an end cap 321, so as to admit axial fixation and rotational freedom relative to the nail stem 327. When the patient applies weight, the load is transmitted from the bone screw 115 to the sleeve 336, which bears down on the pin 339 and transmits the load via the insert 334, end cap 321, and nail stem 327 to the distal bone fragment. Dynamisation is achieved with the patient in a recumbent position, so the proximal bone fragment is considered fixed. The surgeon applies a distraction force to the foot, which causes the nail stem 327, the end cap 321, the insert 334, and the pin 339 to travel downwards relative to the fixed bone screw 115 and the sleeve 336 with the spiral ratchet groove 337. The pin 339 rotates and translates downward to the trough of the spiral ratchet groove 337 and the when the surgeon releases the foot, the pin 339 translates and rotates to the peak of the next ratchet increment, which in turn brings the proximal and distal bone fragments closer together. The embodiment may or may not have a rotational spring element to ensure that the sleeve 336 only rotates in one direction relative to the insert 334. The shape and position of the spiral ratchet groove in the sleeve are shown here by way of example only. In a further embodiment, the spiral ratchet could be formed in the insert 334, with the tracking pin attached to the sleeve 336.

Figure 36:
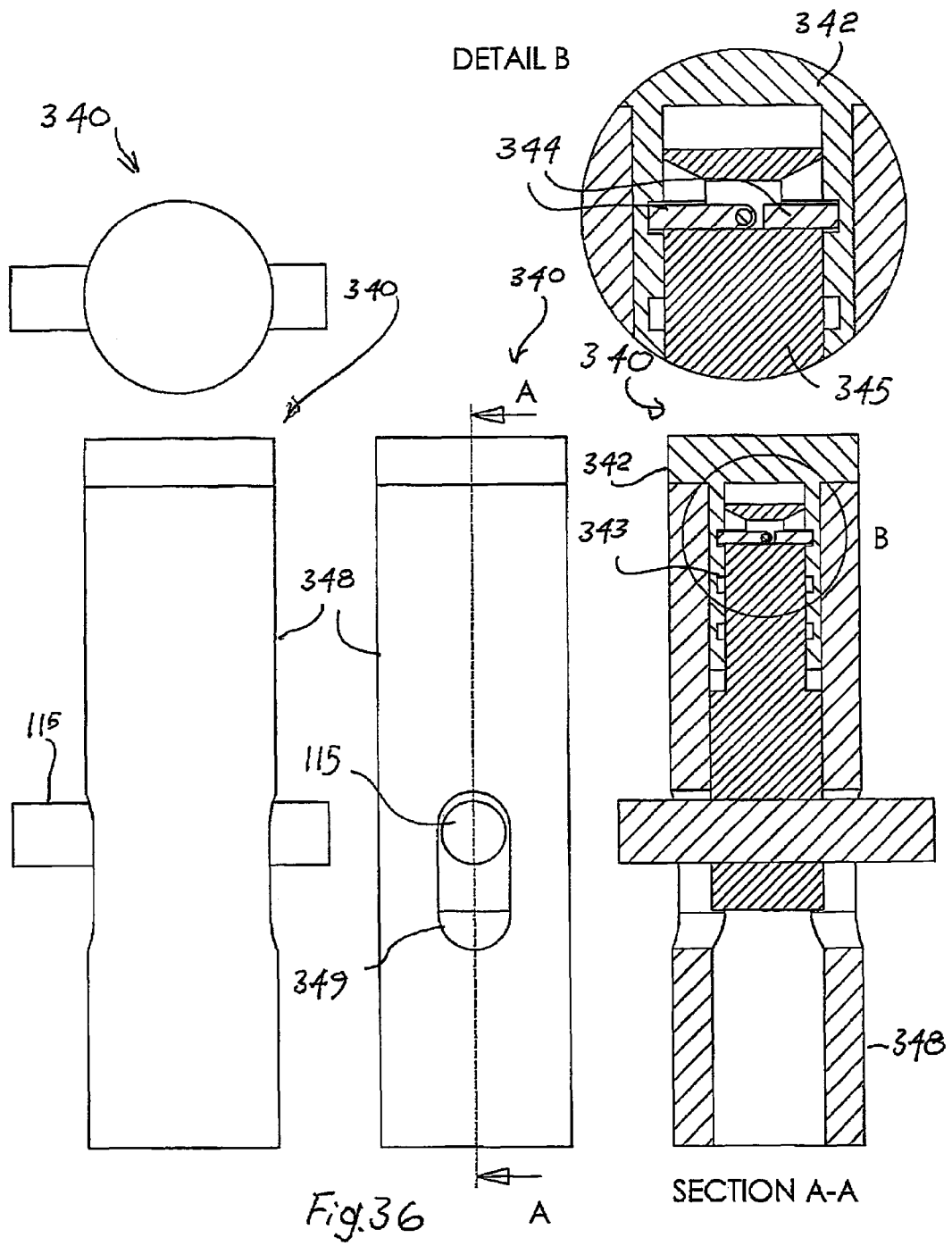
Figure 37:
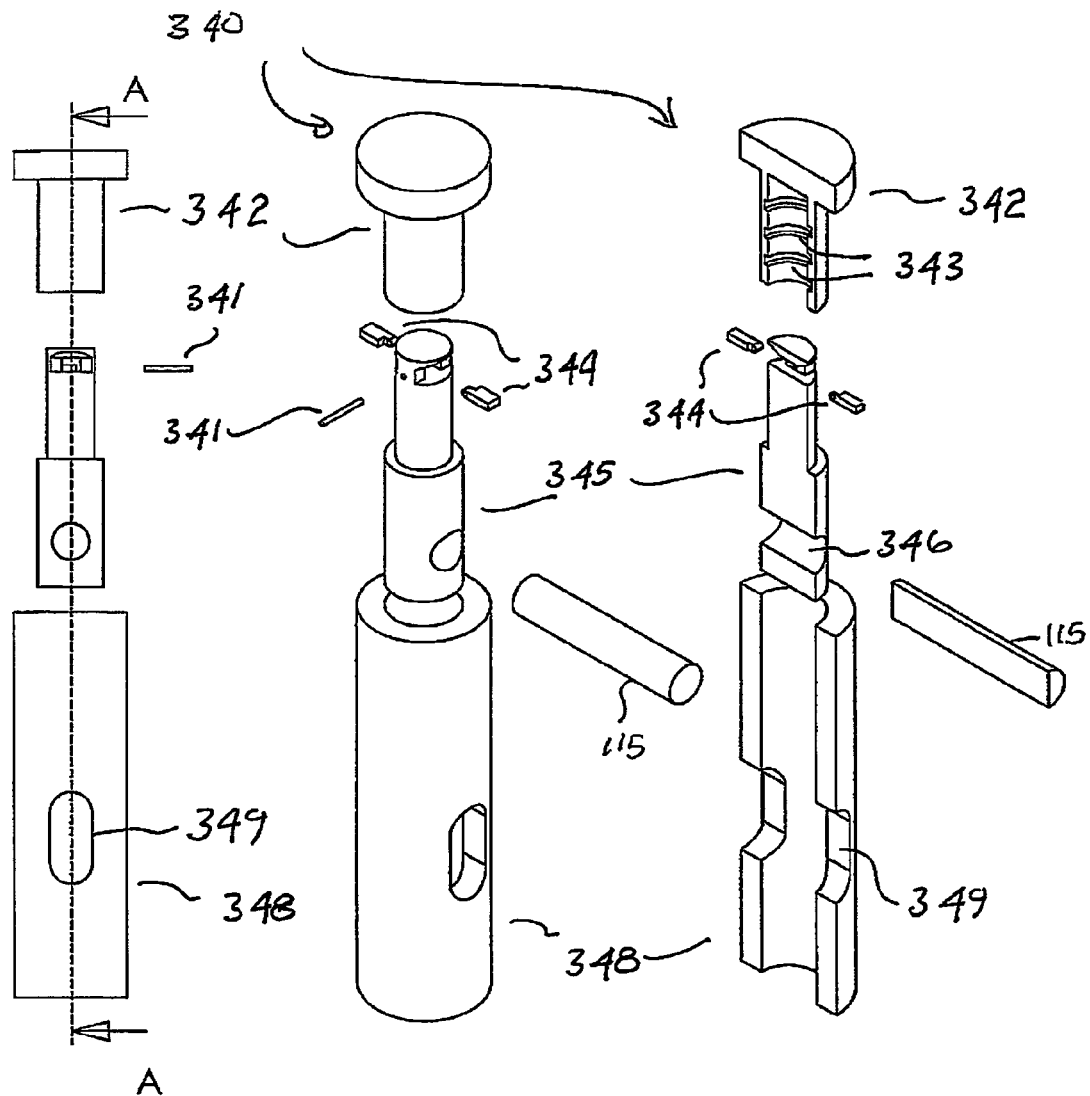

In one embodiment (FIGS. 36 and 37), in a nail 340 a bone separation control mechanism is comprised of a pair of spring-resisted hinged plates. The bone screw 115 passes through a hole in a slider 345. A pair of plates 344 is pinned to the slider 345 and a rotational spring or other energy storage element embedded in or near the pinned joint prevents the plates 344 from freely rotating upward. In their initial position, the pins are engaged in an uppermost groove 343 in an end cap 342. The end cap 342 is threaded into the proximal end of a nail stem 348. When the patient applies weight, the load is transmitted from the bone screw 115 to the slider 345 and the plates 344, which translate downward in the groove 343 to generate micromotion. The plates 344 bear down on the bottom surface of the groove 343 and the load is transmitted to the end cap 342, the nail stem 348, and the distal bone fragment. If the load applied exceeds the threshold of the resistive element at the pinned joint, the plates 344 will rotate upward allowing the slider 345 to progress downwards to the next groove 343 in the modified end cap 342, thereby bringing the bone fragments closer together. The ratchet profile, including the angle, depth, width, spacing, and orientation of bearing surfaces and sliding surfaces shown in FIGS. 36 and 37 is given for illustrative purposes only to represent a series of grooves that differentiate unique ratchet increments for bone separation distance control. In a further embodiment, the hinged plates could be carried on the end cap 342 and the ratchet grooves 343 formed on the slider 345.

In one embodiment (FIGS. 38 and 39), the device may include the capability for post-hoc adjustment of the distance between the proximal and distal bone fragments. In a previous embodiment (FIGS. 15 to 17), the inner insert 106 transmitted loads from the bone screw 115 through shear pins 108 and 109 to the outer insert 107, which was attached to the nail stem 110 via the proximal screw threads 111 and 112. In the current embodiment, in the nail 360 an inner insert assembly 361 may be comprised of three sub-components to facilitate rotational freedom of an outer insert 365 relative to the bone screw 115. A slotted sleeve 362 has a circular bearing lip, which supports a similar circular bearing lip on a bone screw adapter 363. A threaded locking ring 364 holds the slotted sleeve 362 and the bone screw adapter 363 together and allows them to rotate relative to each other. The assembled inner insert 361, comprising the slotted sleeve 362, bone screw adapter 363, and locking ring 364, is then attached to the outer insert 365 via shear pins 108 and 109. The device is threaded into proximal screw threads in the nail stem, which is then implanted into the patient. After the surgeon inserts the bone screw 115 through the nail stem 366 and the bone screw adapter 363, the axial position of the bone screw 115 may be adjusted by rotating the outer insert in the proximal screw threads. Thus, the outer insert 365, the shear pins 108 and 109, and the slotted sleeve 362 rotate together and translate axially in the proximal screw threads 367 while the bone screw adapter 362 and bone screw 115 only translate axially and do not rotate. In this way, the bone separation distance may be adjusted after the bone screws have been inserted while preserving the micromotion and dynamisation functionality of the device. When the bone separation distance has been set to the surgeon's satisfaction, the end cap is threaded into the proximal threads in the nail to fix the position of the device.

The embodiments described are presented by way of example only. Each of the elements described in any of the embodiments may or may not be arranged in combination with elements from another embodiment to achieve the same effect or combination of effects. For example, any of the mechanisms presented for bone separation control (including but not limited to shear pins, beam ratchets, spring pin ratchets, spiral ratchets, hinged ratchets) may be combined with any of the operative assembly techniques (including but not limited to insertion of the pre-assembled module in the nail prior to implantation in the patient or two-part assembly of the module during implantation of the nail) and with or without damped micromotion by one or a plurality of Belleville washers or other energy-absorbing elements arranged in any series or parallel combination. The illustrative figures provided show examples of the mechanical subcomponents arranged in a few selected configurations and are not an exhaustive representation of all of the possible permutations of the subcomponents described herein. A few illustrative examples of these alternative permutations are now presented.

Figure 40:
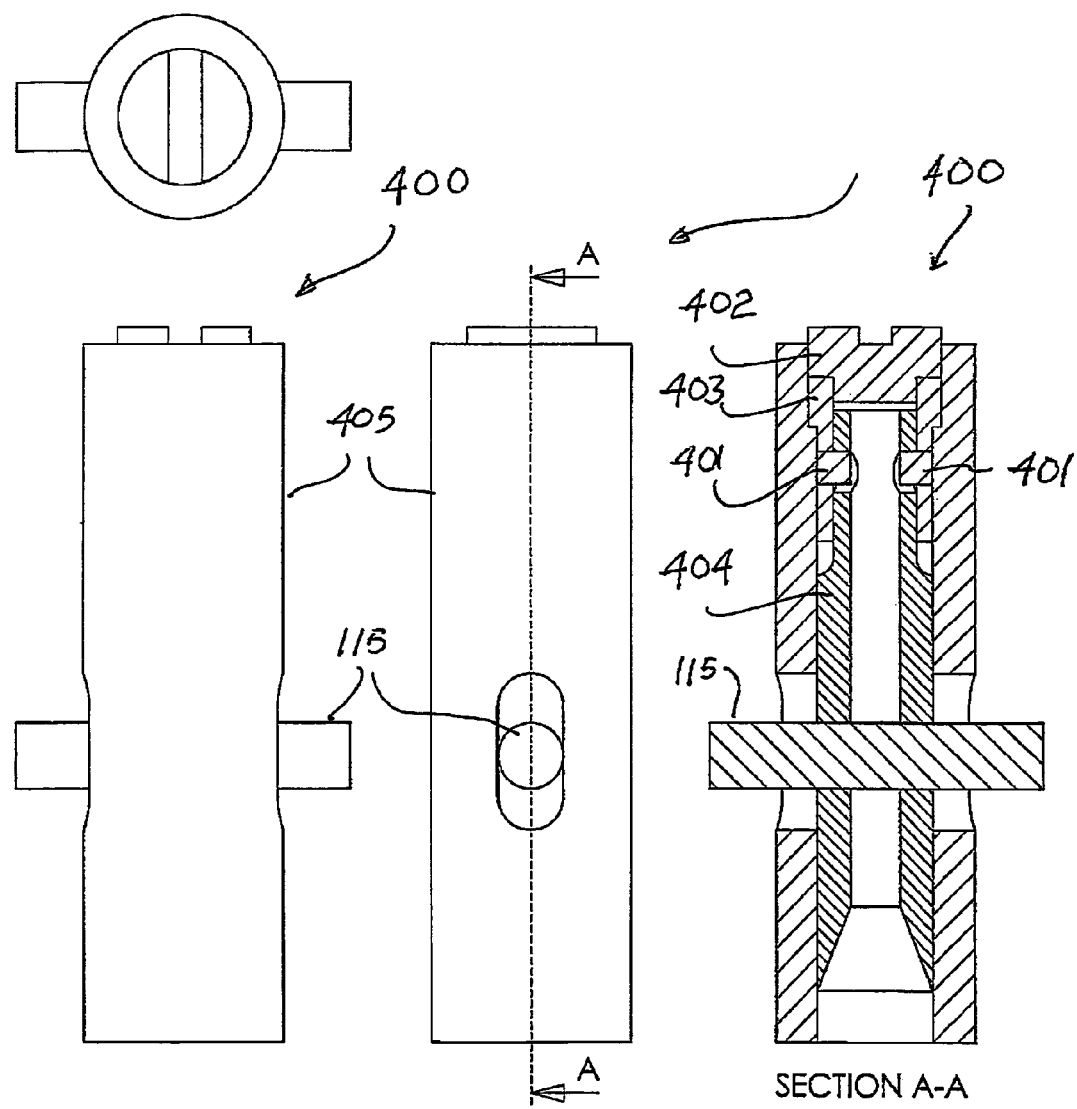
FIGS. 40 to 57 are views shows six further embodiments comprising alternative configurations of the mechanical sub-components described in the embodiments of FIGS. 15 to 19.
Figure 41:
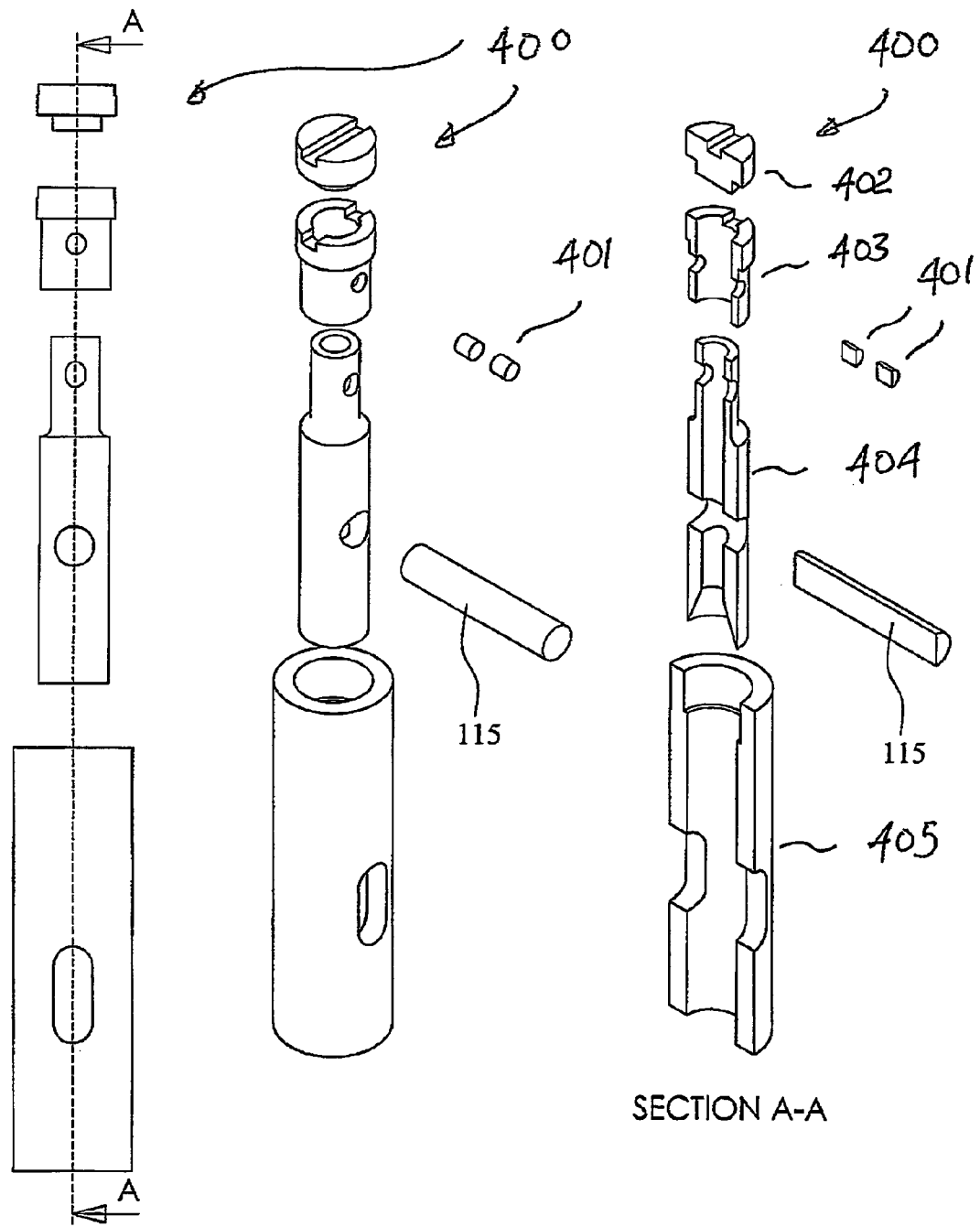

In one embodiment (FIGS. 40 and 41), a nail 400 comprises a single-stage pin-in-slot mechanism for controlling interfragmentary micromotion. The device 400 has an end cap 402, pins 401, an outer insert 403, an inner insert 404, and a stem 405. The pins 401 are large enough to withstand patient weight bearing without shearing, so no dynamisation occurs. The pin in slot allows controlled bone fragment separation as the shear pin pair 401 travels in the slot in the inner insert 404. The interfragmentary micromotion distance is chosen to accelerate callus formation and fracture healing by mechanical stimulation while providing controlled bone separation during both stance and swing phases via mechanical hard-stops. Damping of the motion between bone fragments is provided by the inherent viscoelastic properties of the tissue in the bone gap.

Figure 42:
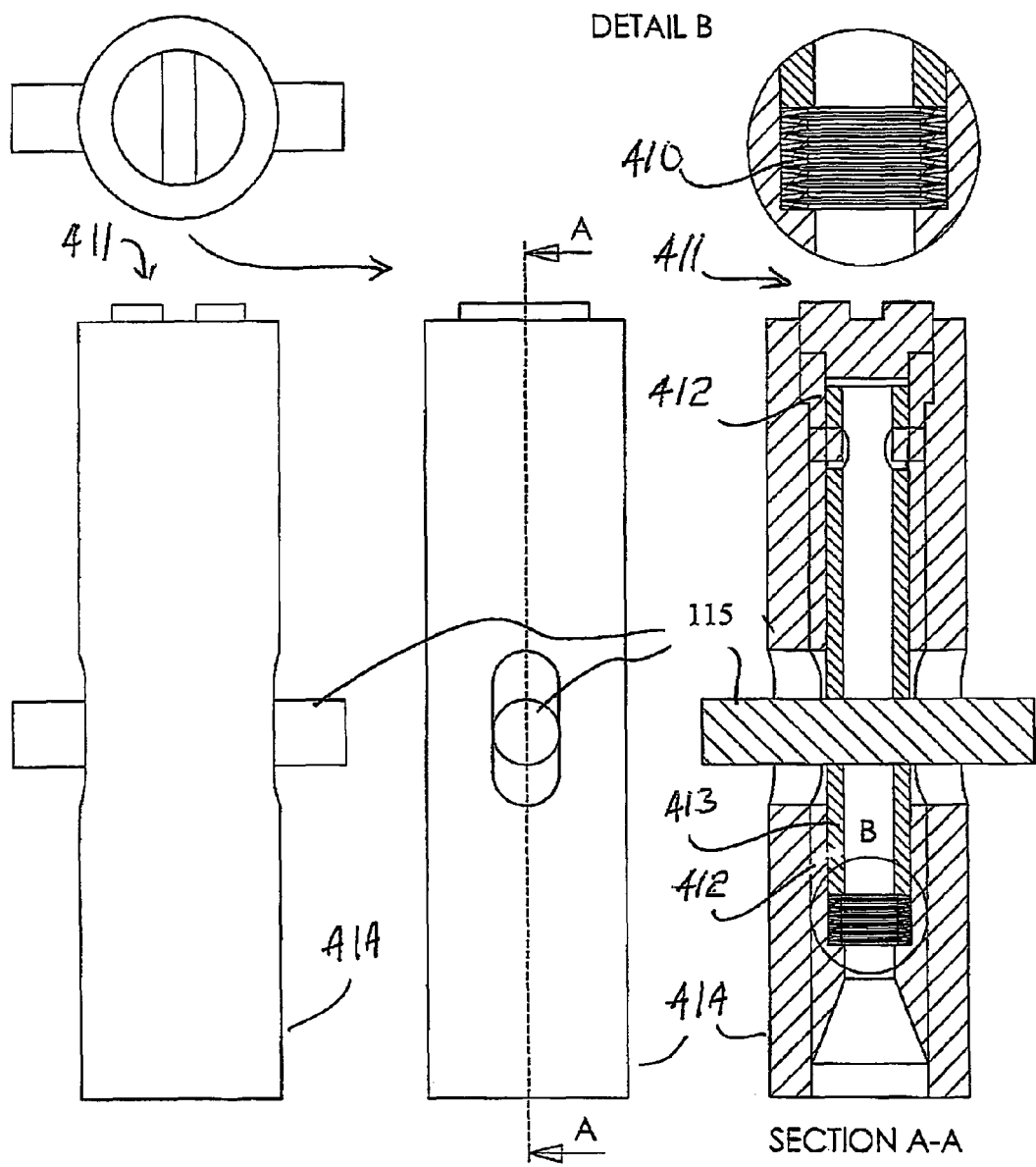
Figure 43:
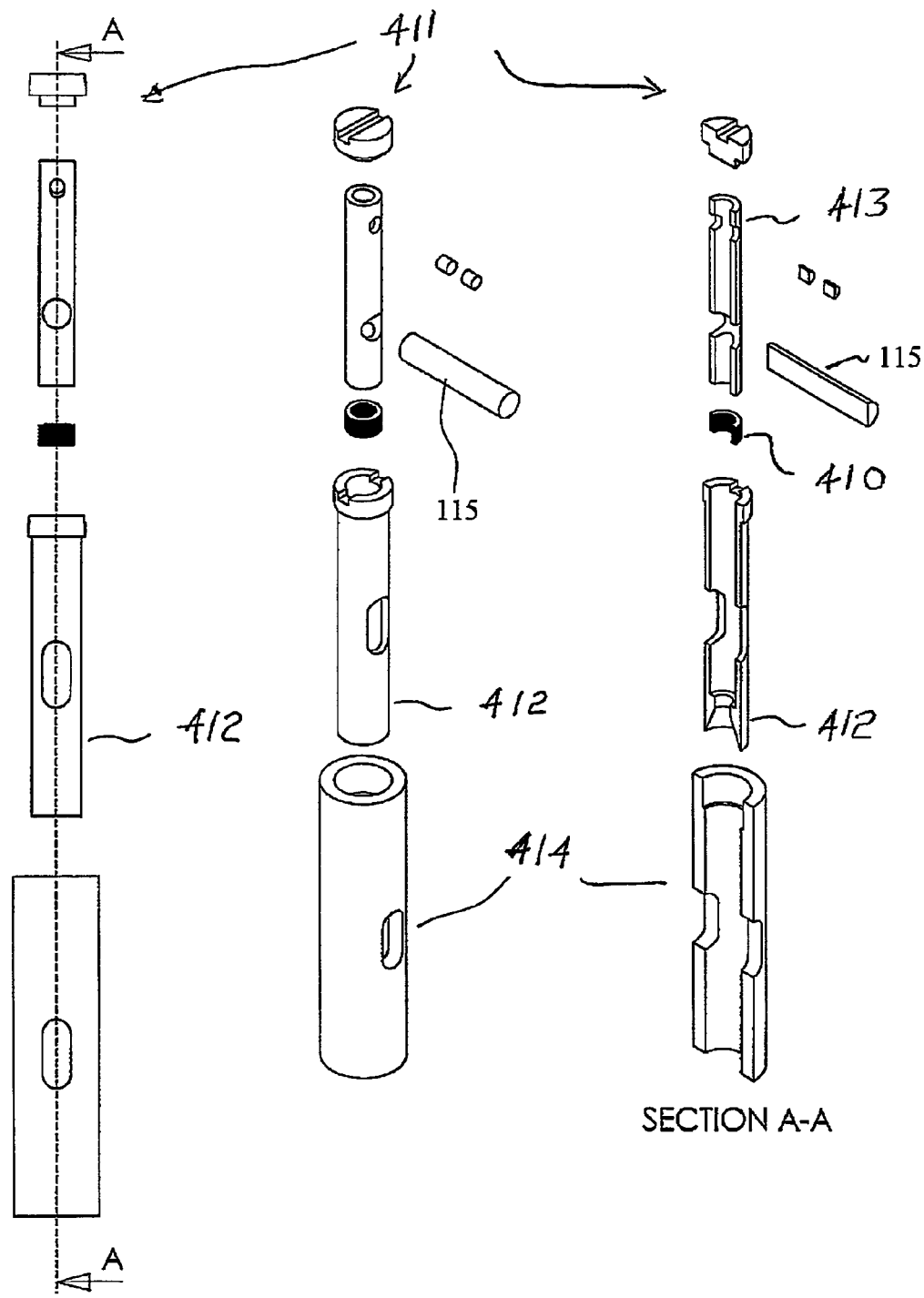

In one embodiment (FIGS. 42 and 43), in a nail 411 damping action provided by the tissue in the bone gap may be augmented by the addition of a plurality of Belleville washers 410 or other energy-storage elements, which are compressed during stance phase and rebound to their initial shape during swing phase. The Belleville washers 410 rest on an outer insert 412 and are compressed by an inner insert 413, which transmits loads from the proximal bone screw 115.

Figure 44:
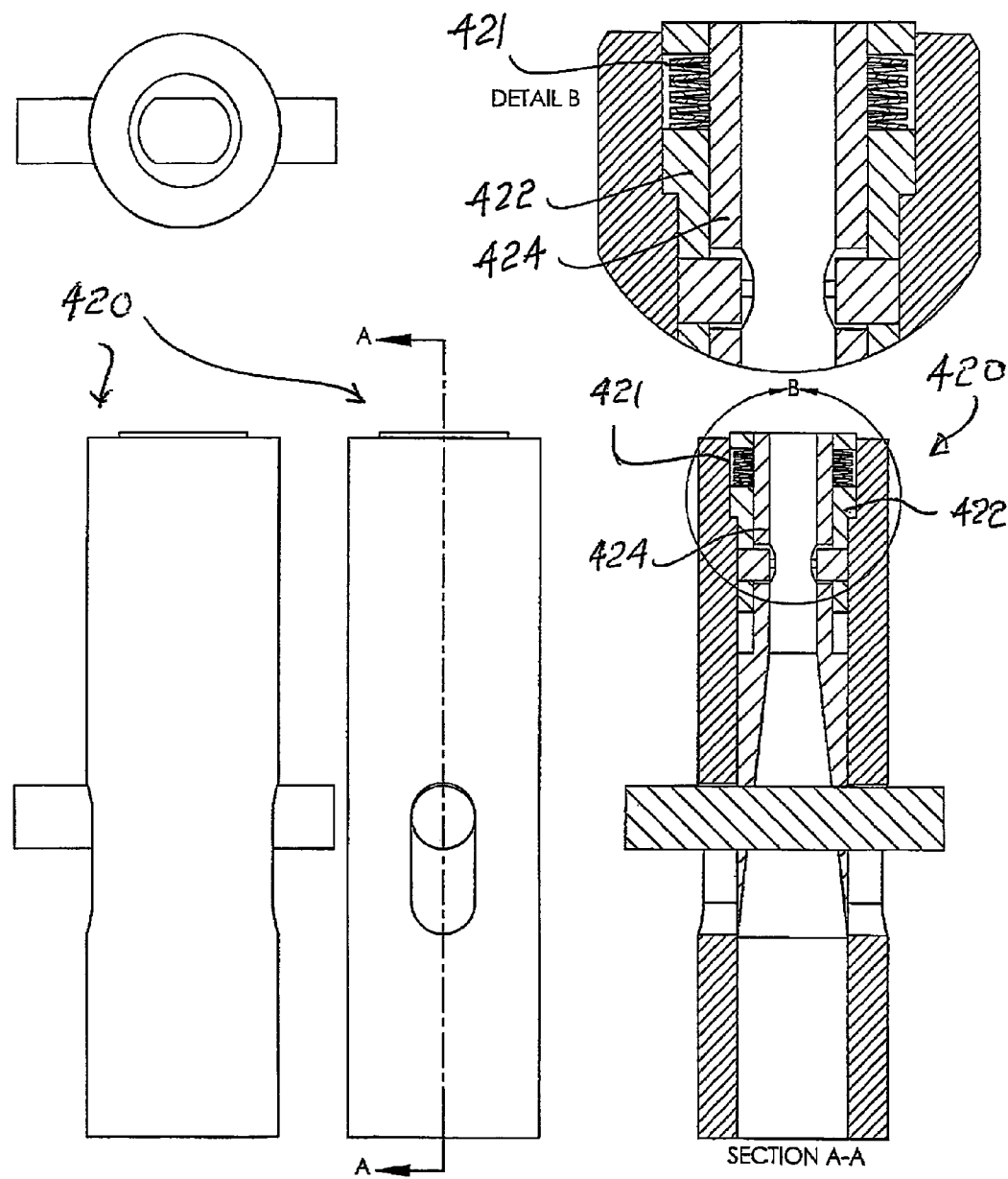
Figure 45:
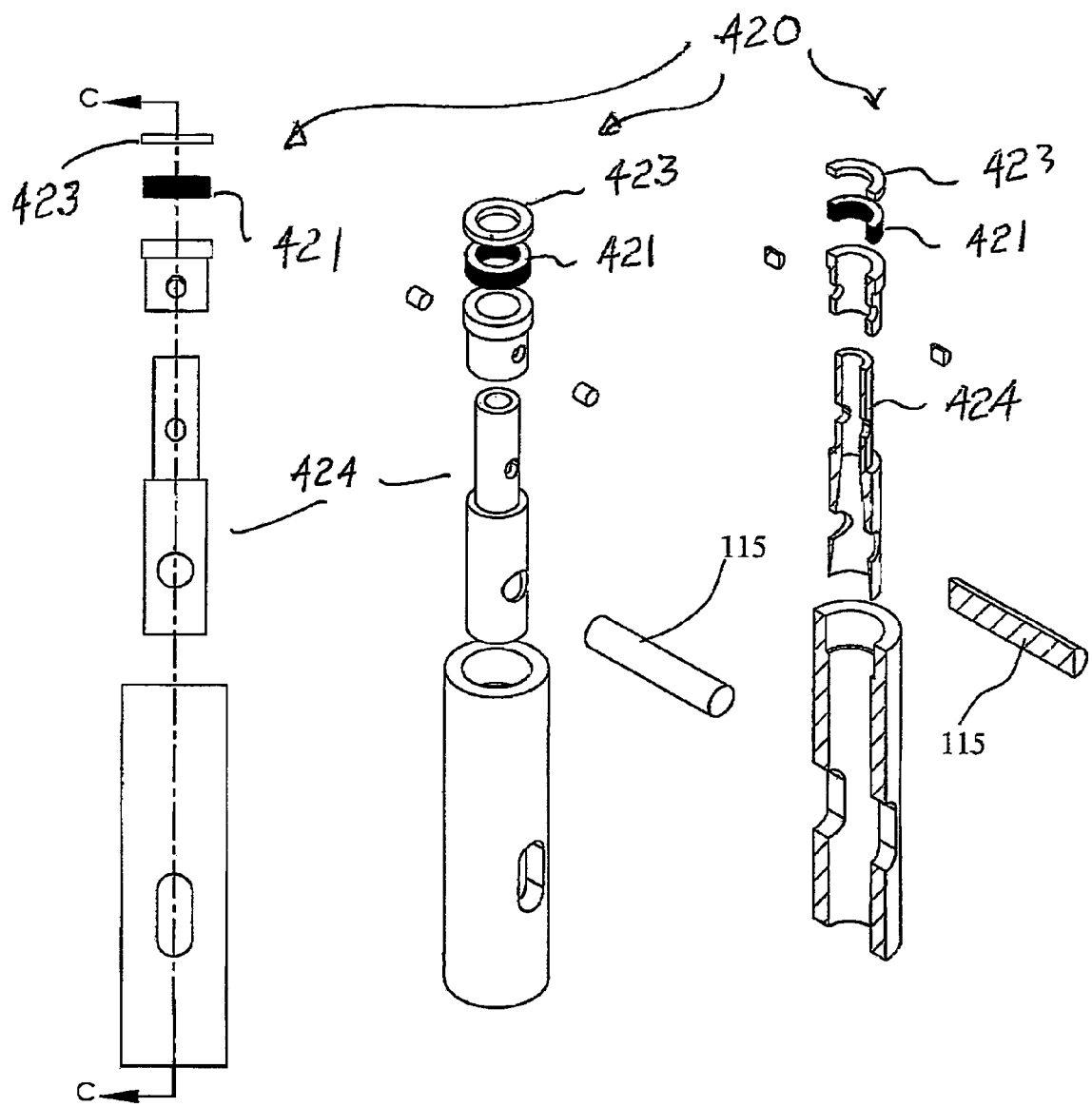

In an alternative embodiment (FIGS. 44 and 45), the nail 420 may comprise Belleville washers 421 seated on top of the outer insert 422 and compressed by a disc 423 that is welded or otherwise affixed to an inner insert 424 which transmits loads from the bone screw 115.

Figure 38:
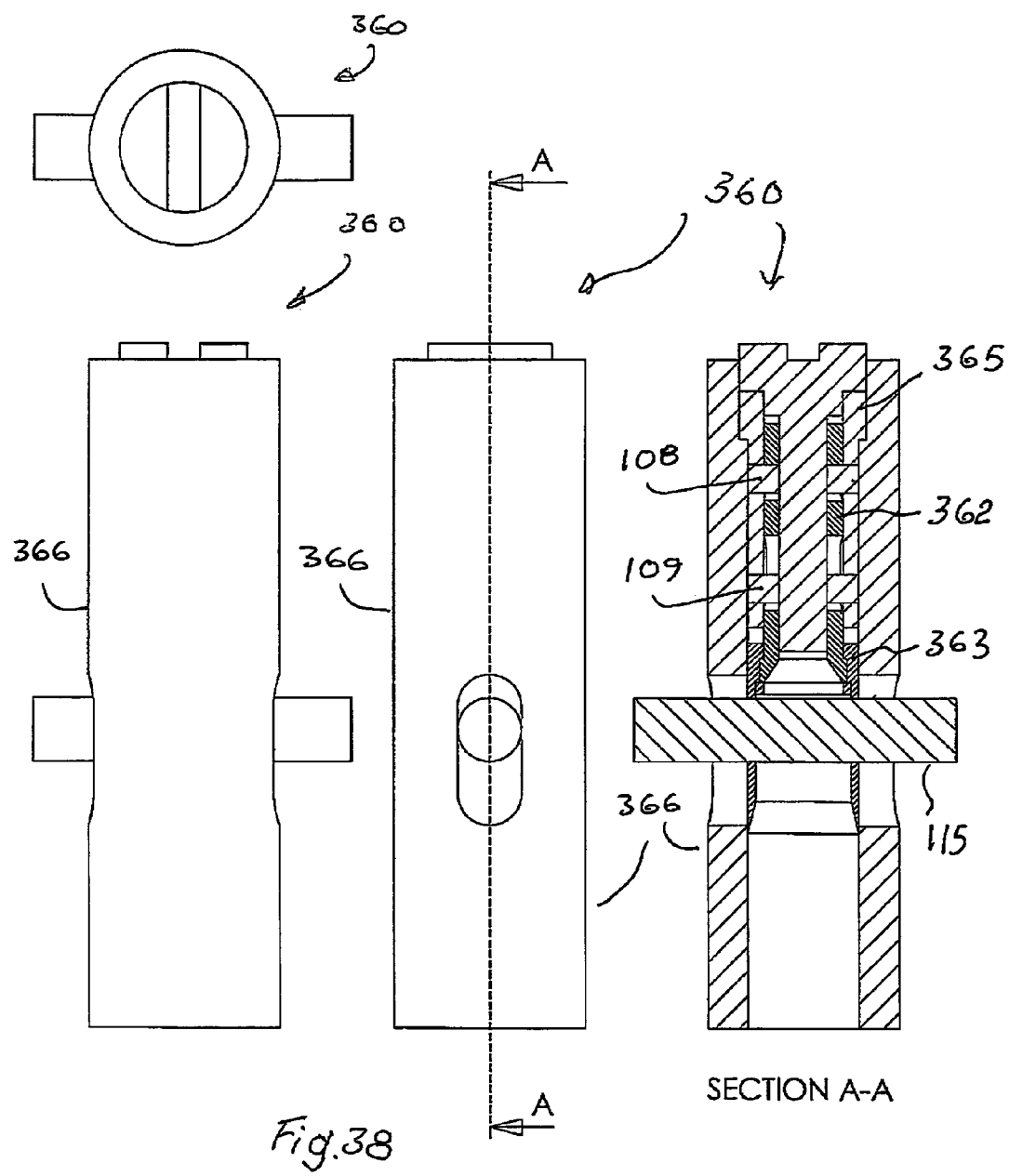
Figure 39:
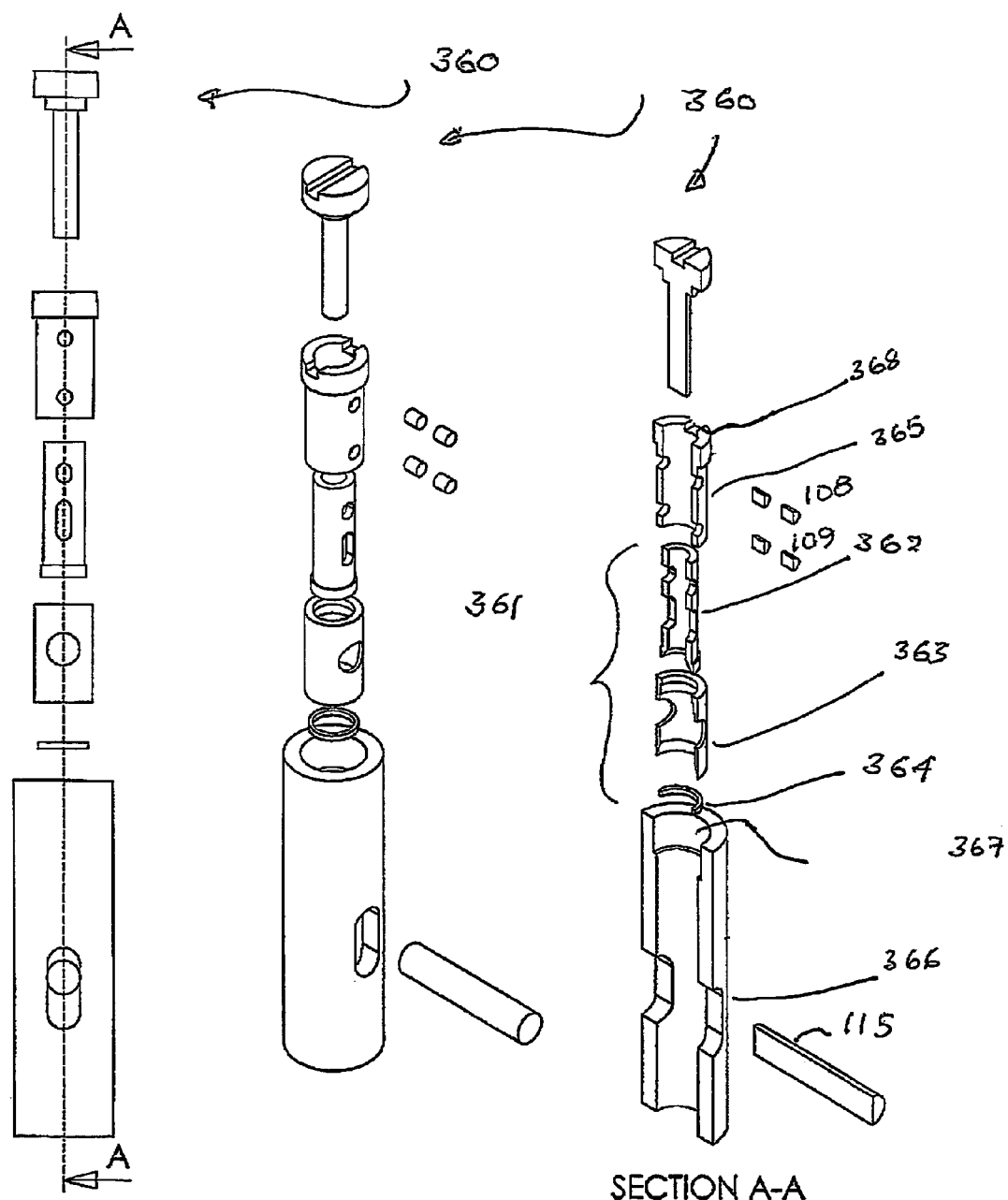
Figure 46:
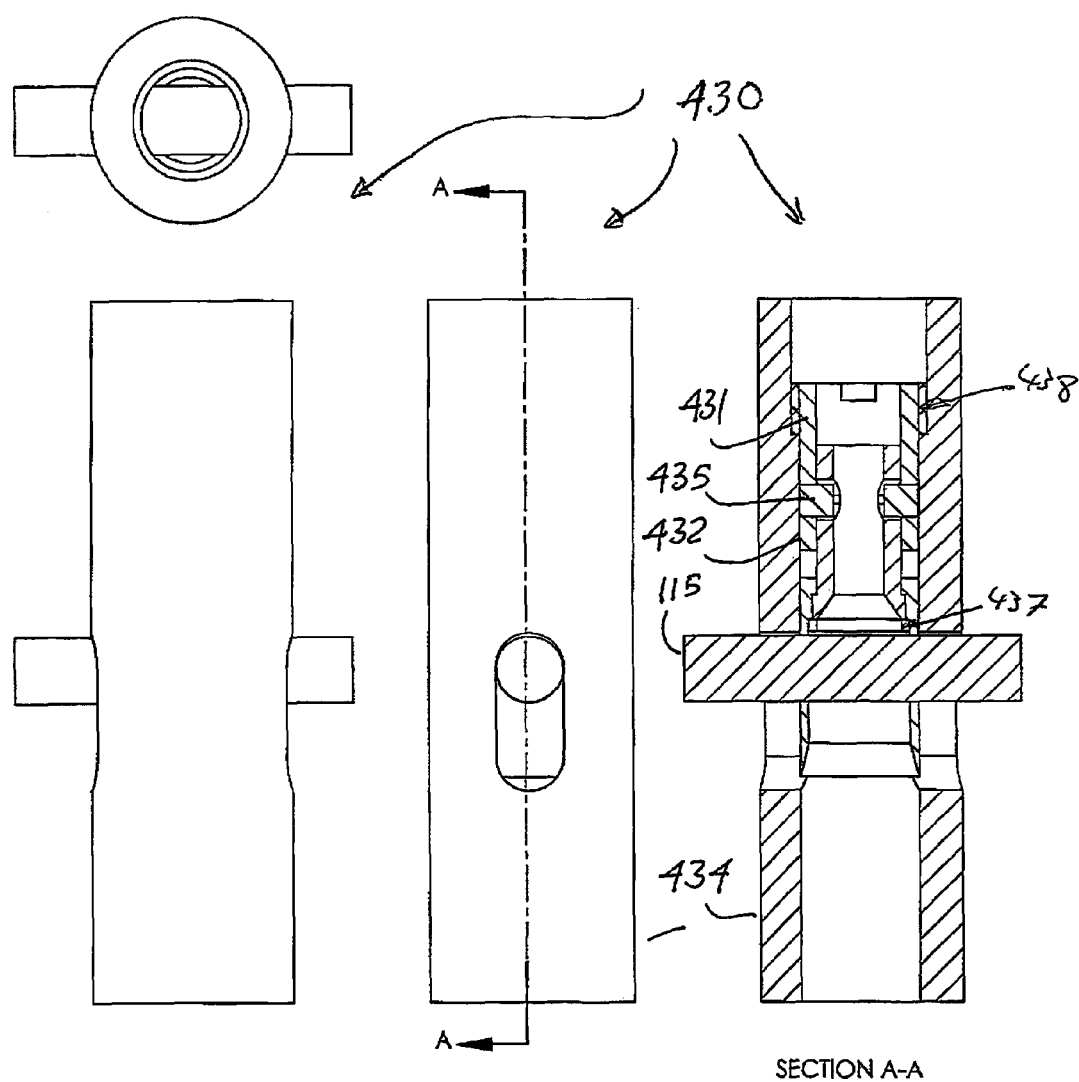
Figure 47:
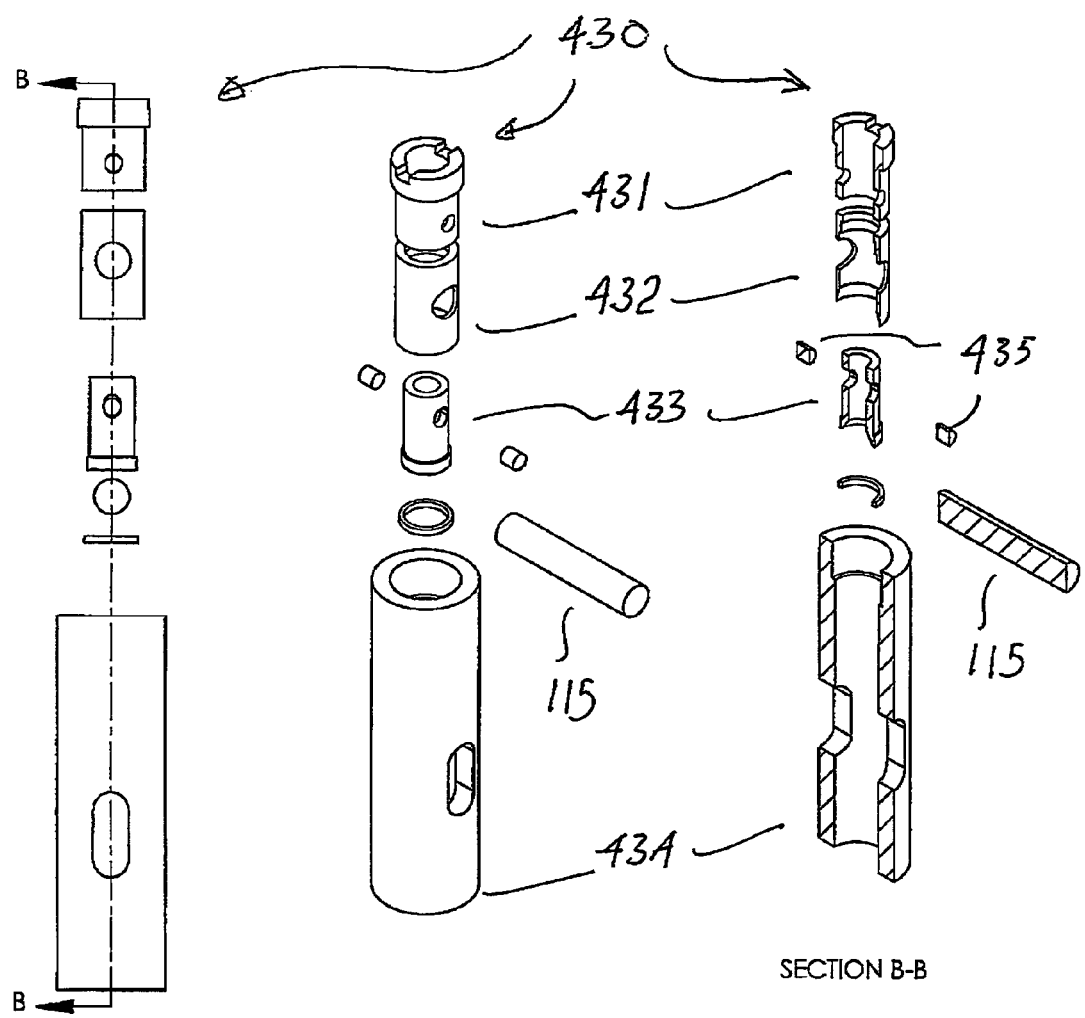

In another embodiment (FIGS. 46 and 47), a nail 430 may comprise the pin-in-slot micromotion mechanism much as described in a previous embodiment (FIGS. 40 and 41) and is augmented to include the capability for post-hoc adjustment of the bone gap as described in a previous embodiment (FIGS. 38 and 39). In this embodiment there are outer insert, inner insert, and bone screw adaptor 431, 433, and 432 in a stem 434. In this embodiment, the nail 430 an inner insert assembly 436 may be comprised of three sub-components to facilitate rotational freedom of an outer insert 431 relative to the bone screw 115. The inner insert 433 has a circular bearing lip, which supports a similar circular bearing lip on a bone screw adapter 432. A threaded locking ring 437 holds the slotted sleeve 433 and the bone screw adapter 432 together and allows them to rotate relative to each other. The assembled inner insert 431, comprising the slotted sleeve 433, bone screw adapter 432, and locking ring 437, is then attached to the outer insert 431 via shear pins 435. The device is threaded into proximal screw threads in the nail stem 434, which is then implanted into the patient. After the surgeon inserts the bone screw 115 through the nail stem 434 and the bone screw adapter 432, the axial position of the bone screw 115 may be adjusted by rotating the outer insert in the proximal screw threads. Thus, the outer insert 431, the shear pins 435, and the slotted sleeve 433 rotate together and translate axially in the proximal screw threads 438 while the bone screw adapter 432 and bone screw 115 only translate axially and do not rotate. In this way, the bone separation distance may be adjusted after the bone screws have been inserted while preserving the micromotion functionality of the device. When the bone separation distance has been set to the surgeon's satisfaction, the end cap is threaded into the proximal threads in the nail to fix the position of the device.

Figure 48:
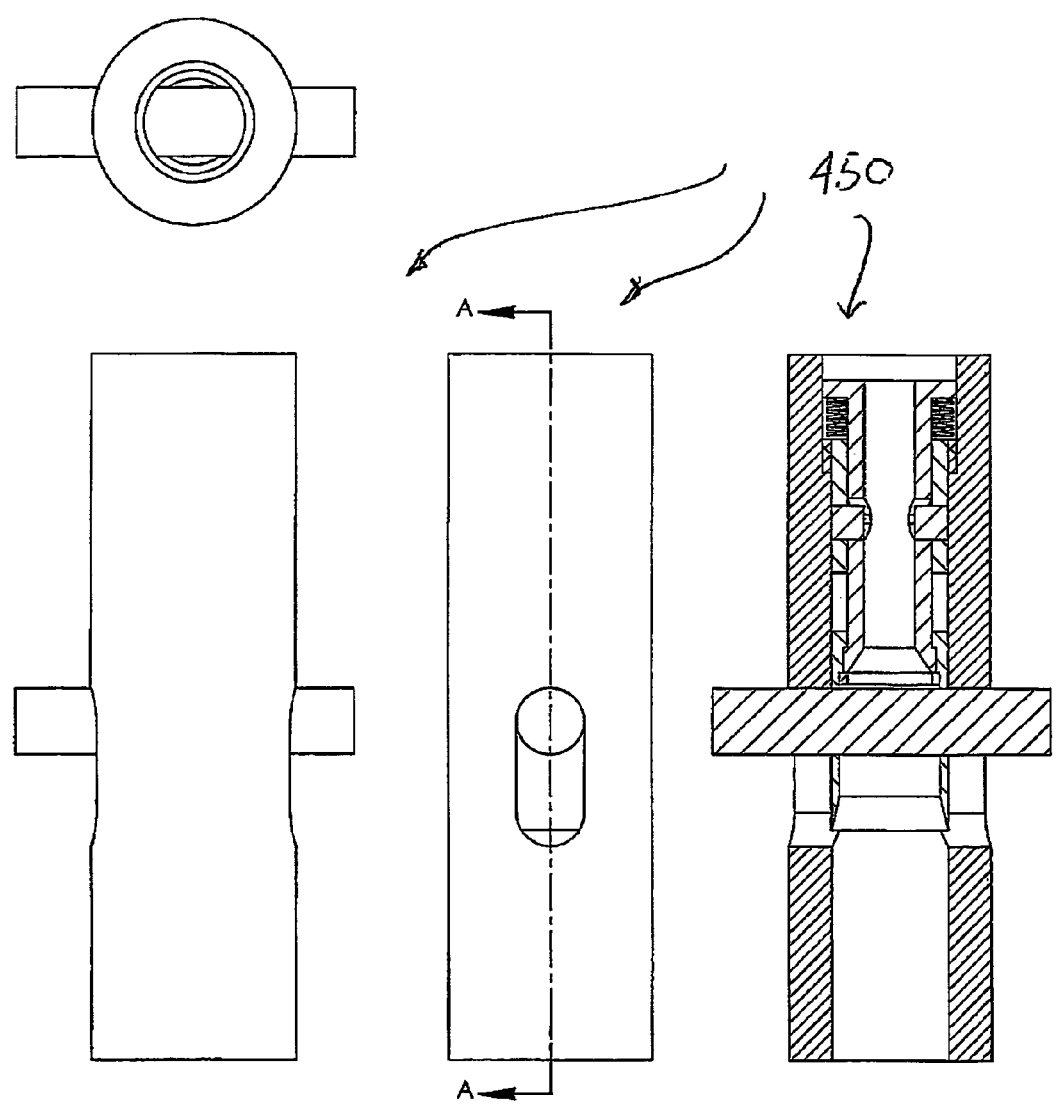
Figure 49:
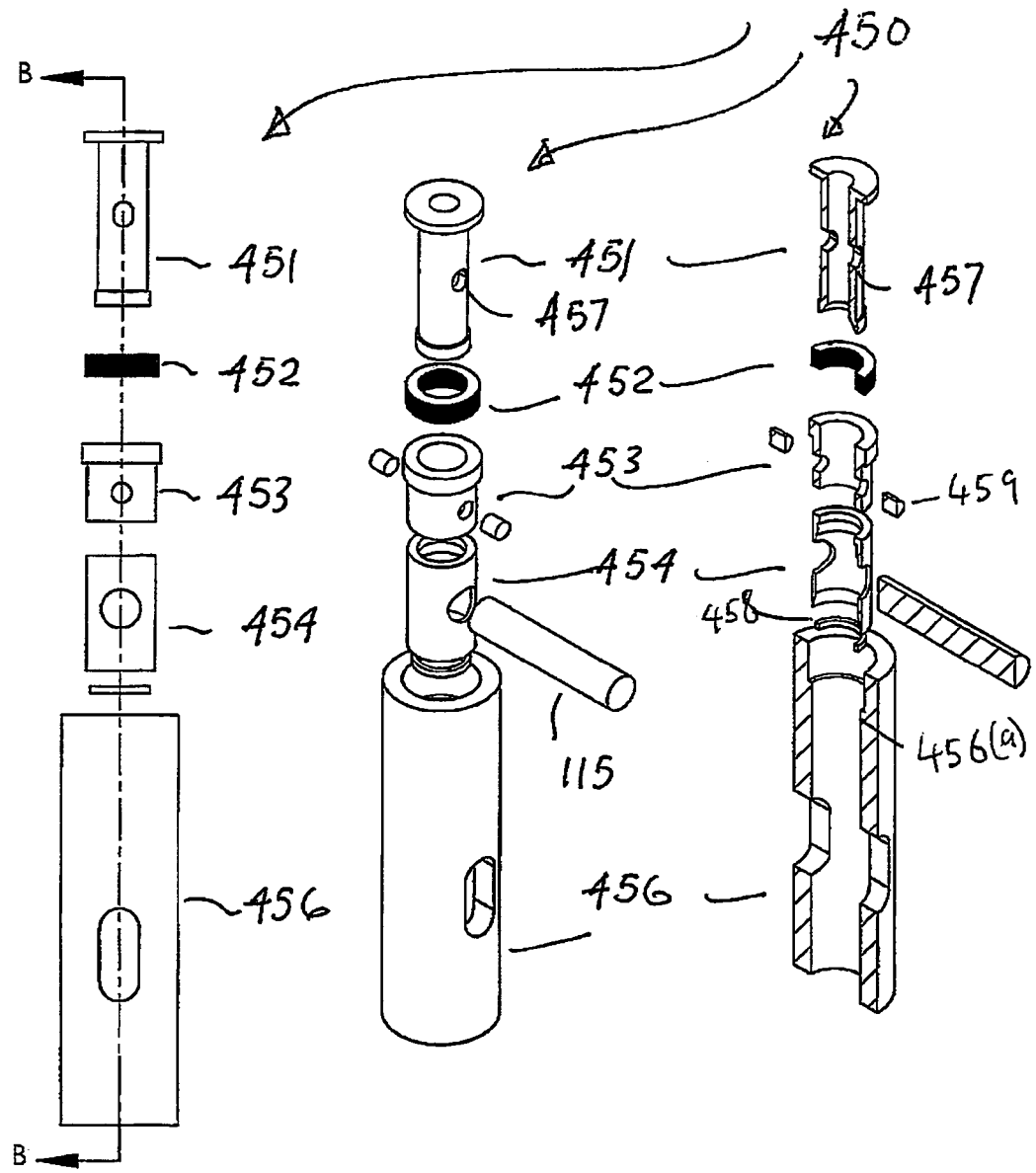

In another embodiment (FIGS. 48 and 49), a nail 450 comprises a damped micromotion mechanism such as described in a previous embodiment (FIGS. 44 and 45) and is augmented to include the capability for post-hoc adjustment of the bone gap as described in a previous embodiment (FIGS. 38 and 39). In descending order as illustrated the nail 450 comprises an end cap 451 with through holes 457, Belleville washers 452, a middle insert 453, a bottom insert 454, in a stem 456. In the current embodiment, the nail 456 an inner insert assembly 450 may be comprised of three sub-components to facilitate rotational freedom of an outer insert 453 relative to the bone screw 115. The inner insert 451 has a circular bearing lip, which supports a similar circular bearing lip on a bone screw adapter 454. A threaded locking ring 458 holds the slotted sleeve 453 and the bone screw adapter 454 together and allows them to rotate relative to each other. The assembled inner insert 450, comprising the slotted sleeve 451, bone screw adapter 454, and locking ring 4**, is then attached to the outer insert 453 via shear pins 459. The device is threaded into proximal screw threads in the nail stem 456, which is then implanted into the patient. After the surgeon inserts the bone screw 115 through the nail stem 456 and the bone screw adapter 454, the axial position of the bone screw 115 may be adjusted by rotating the outer insert in the proximal screw threads. Thus, the outer insert 453, the shear pins 459, and the slotted sleeve 451 rotate together and translate axially in the proximal screw threads 456(a) while the bone screw adapter 454 and bone screw 115 only translate axially and do not rotate. In this way, the bone separation distance may be adjusted after the bone screws have been inserted while preserving the damped micromotion functionality of the device. When the bone separation distance has been set to the surgeon's satisfaction, the end cap is threaded into the proximal threads in the nail to fix the position of the device.

Figure 50:
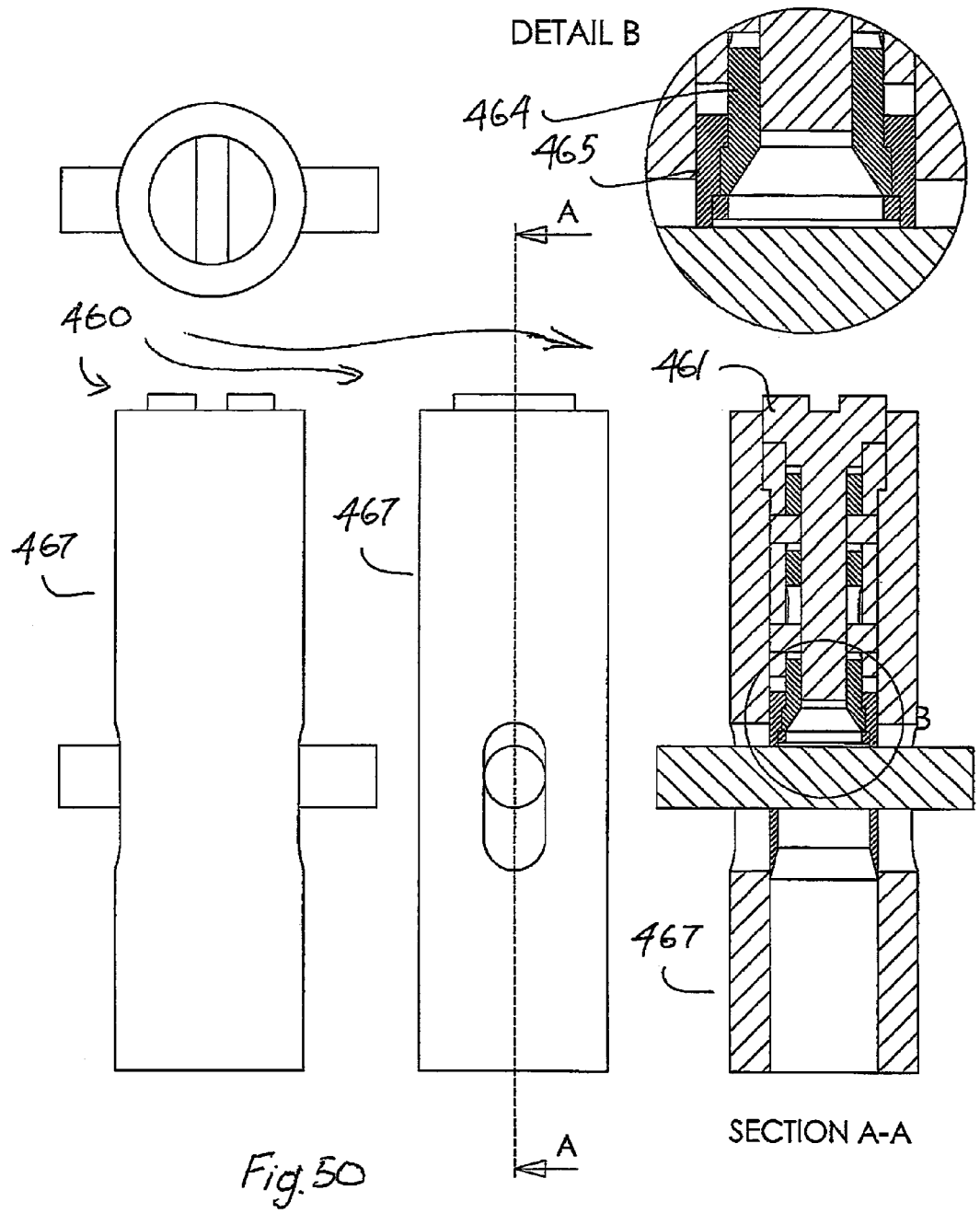
Figure 51:
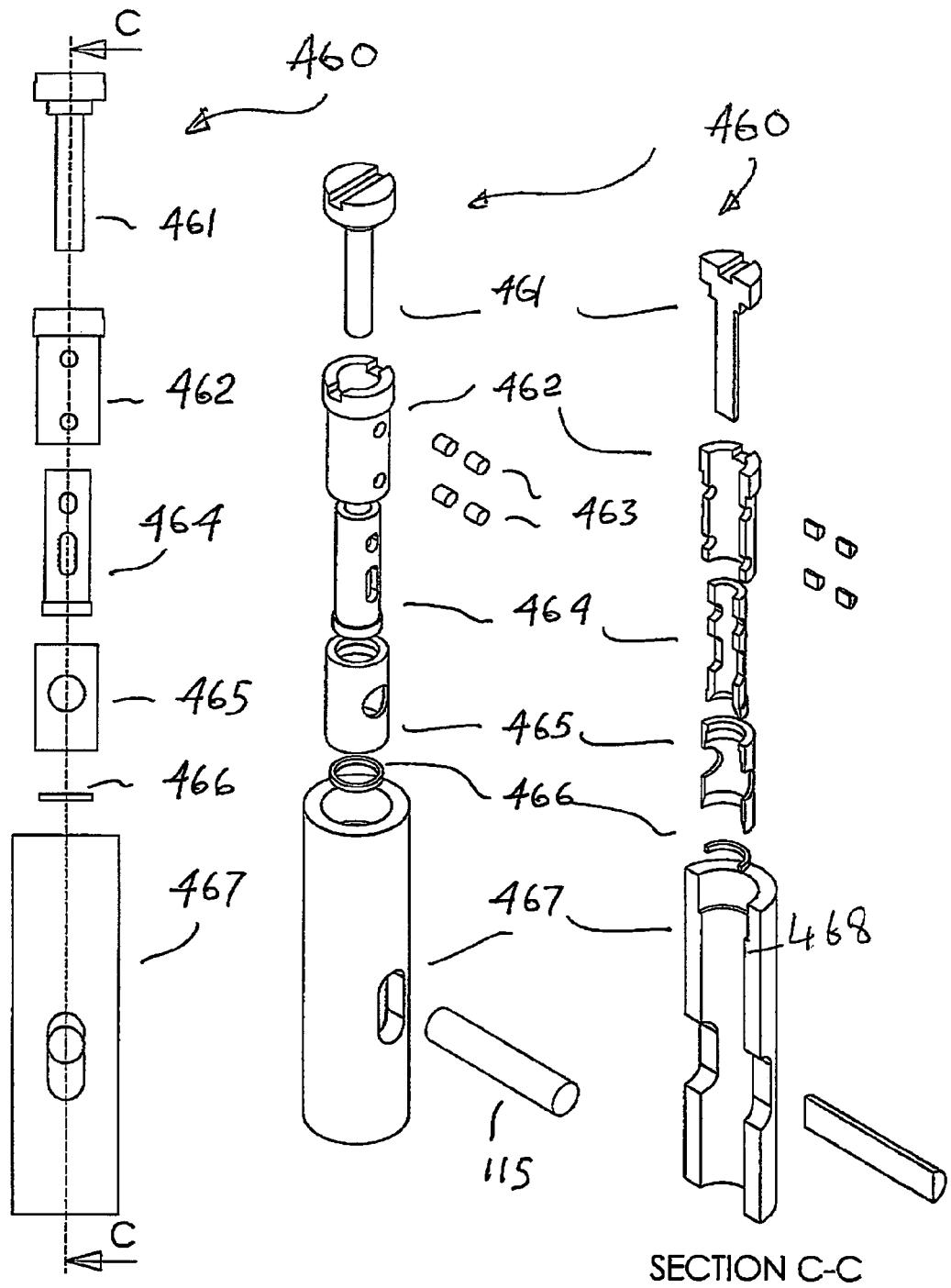

In another embodiment (FIGS. 50 and 51), a nail 460 comprises a multi-stage pin-in-slot mechanism for controlling interfragmentary micromotion and providing non-surgical autodynamisation according to the shear pin concept described in a previous embodiment (for example. FIGS. 16 and 17). The nail 460 also includes the capability for post-hoc adjustment of the bone gap. The nail 460 comprises an end cap 461, upper 462, middle 464, and lower 465 inserts, a washer 466, and a stem 467. In the current embodiment, the nail stem 467 an inner insert assembly 460 may be comprised of three sub-components to facilitate rotational freedom of an outer insert 462 relative to the bone screw 115. The inner insert 464 has a circular bearing lip, which supports a similar circular bearing lip on a bone screw adapter 465. A threaded locking ring 466 holds the slotted sleeve 464 and the bone screw adapter 465 together and allows them to rotate relative to each other. The assembled inner insert 460, comprising the slotted sleeve 464, bone screw adapter 465, and locking ring 466, is then attached to the outer insert 462 via shear pins 463. The device is threaded into proximal screw threads in the nail stem 467, which is then implanted into the patient. After the surgeon inserts the bone screw 115 through the nail stem 467 and the bone screw adapter 465, the axial position of the bone screw 115 may be adjusted by rotating the outer insert in the proximal screw threads. Thus, the outer insert 462, the shear pins 463, and the slotted sleeve 464 rotate together and translate axially in the proximal screw threads 468 while the bone screw adapter 465 and bone screw 115 only translate axially and do not rotate. In this way, the bone separation distance may be adjusted after the bone screws have been inserted while preserving the micromotion and dynamisation functionality of the device. When the bone separation distance has been set to the surgeon's satisfaction, the end cap 461 is threaded into the proximal threads in the nail to fix the position of the device.

Figure 52:
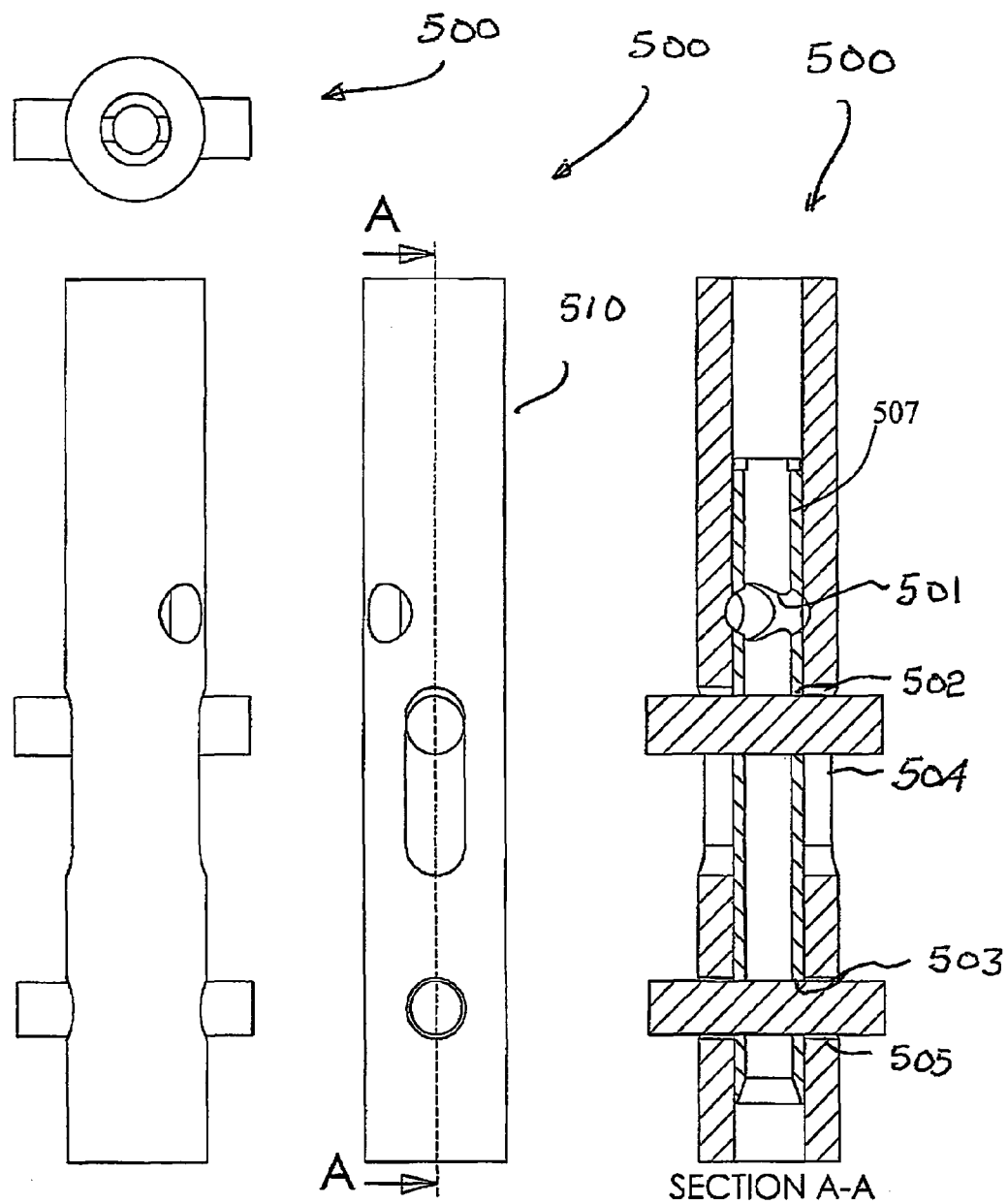
Figure 53:
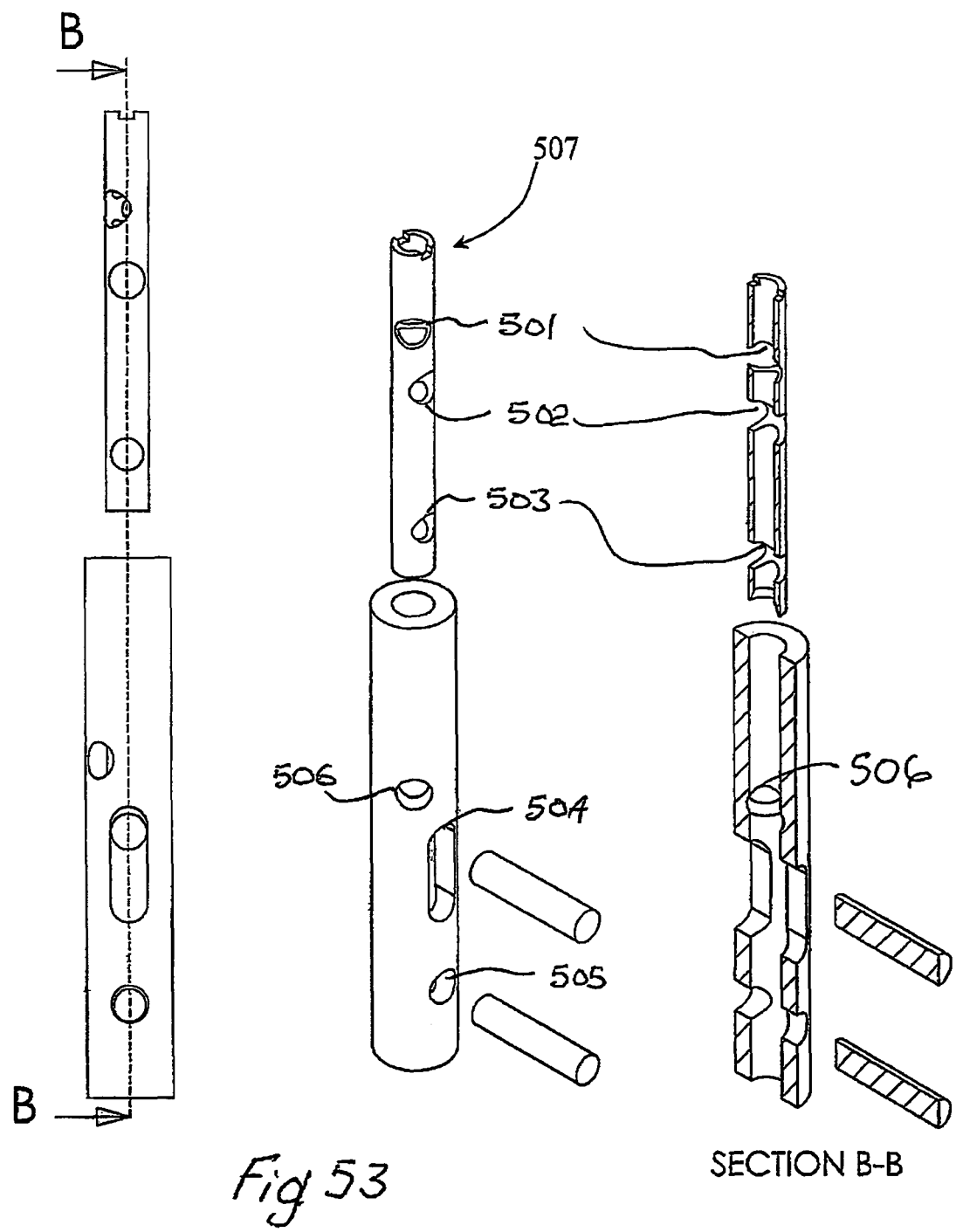

In another embodiment (FIGS. 52 and 53), a nail 500 comprises a tube 507 that allows interfragmentary micromotion by controlling the alignment of bone screws in oversized holes. The tube contains multiple through-holes 501, 502 and 503 of different diameters that are aligned with fixation holes 505, and 506 and a dynamic slot 504 in a nail stem 510. The middle through-hole 502 has a diameter equal to the width of the dynamic slot 504 in the nail 510. The upper and lower through holes 501 and 503 have a diameter slightly smaller than the diameter of the holes 506 and 505 in the nail stem 510. To lock the micromotion-enabled nail, the surgeon inserts a large bone screw 115 through the stem slot 504 and middle through-hole 502 to provide rotational fixation for the tube and to guarantee purely axial micromotion. The surgeon also inserts two smaller bone screws through either or both the upper and lower through-holes 506/501 and 505/503. The difference in the diameter between the holes in the nail and the holes in the tube determines the micromotion distance. In this example the bone screw 115 diameter is 4 mm, passing through an over-size hole 505 of 5 mm, giving a micromotion distance of 1 mm.

In an alternative embodiment, either the upper or lower through-holes in the tube can be made equal in diameter to the corresponding hole in the nail, so the surgeon has the option to insert a large bone screw and engage rigid fixation without micromotion. In the embodiments discussed above, damping of the motion between bone fragments is provided by the inherent viscoelastic properties of the tissue in and around the bone gap.

Figure 54:
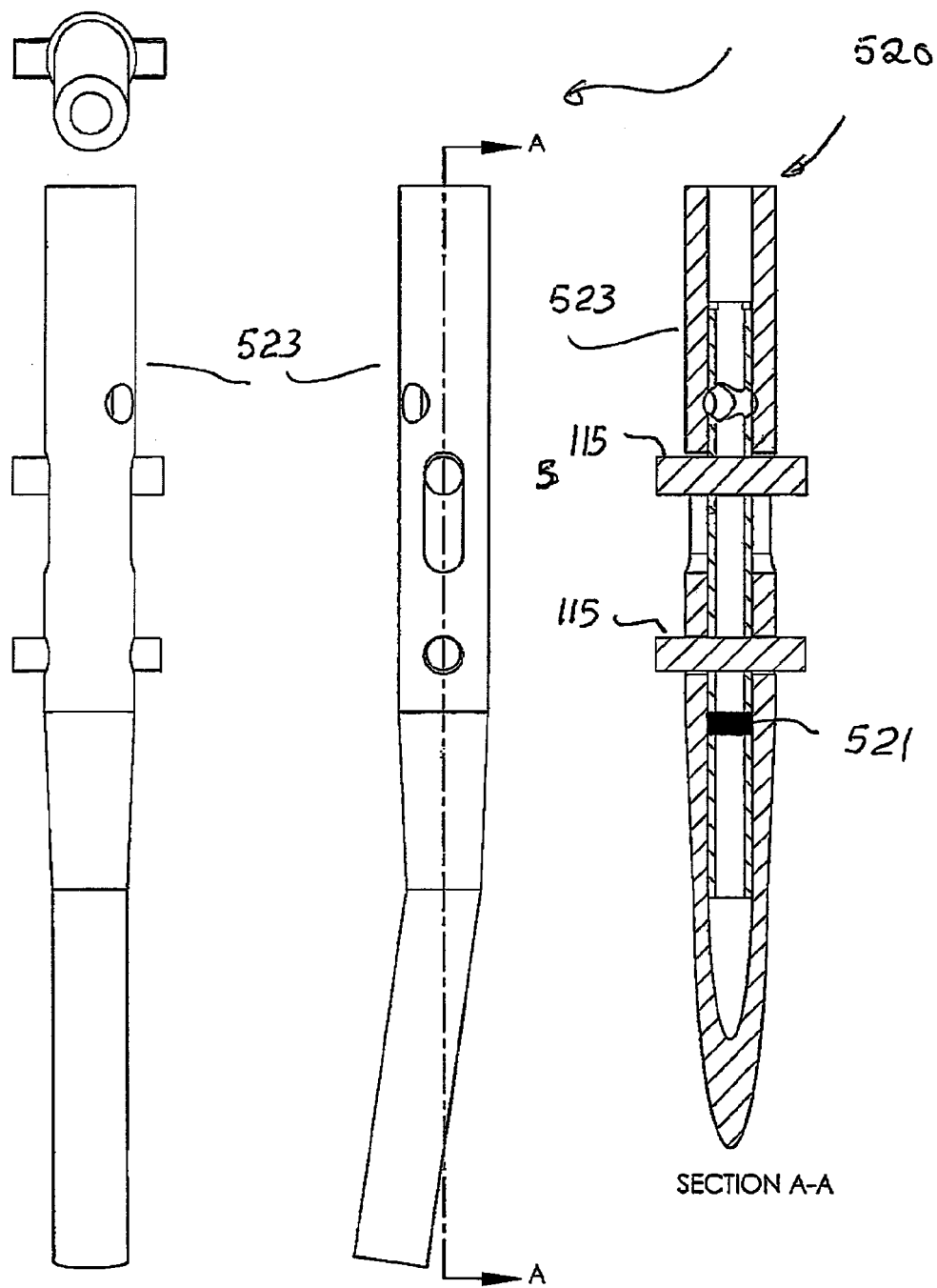
Figure 55:
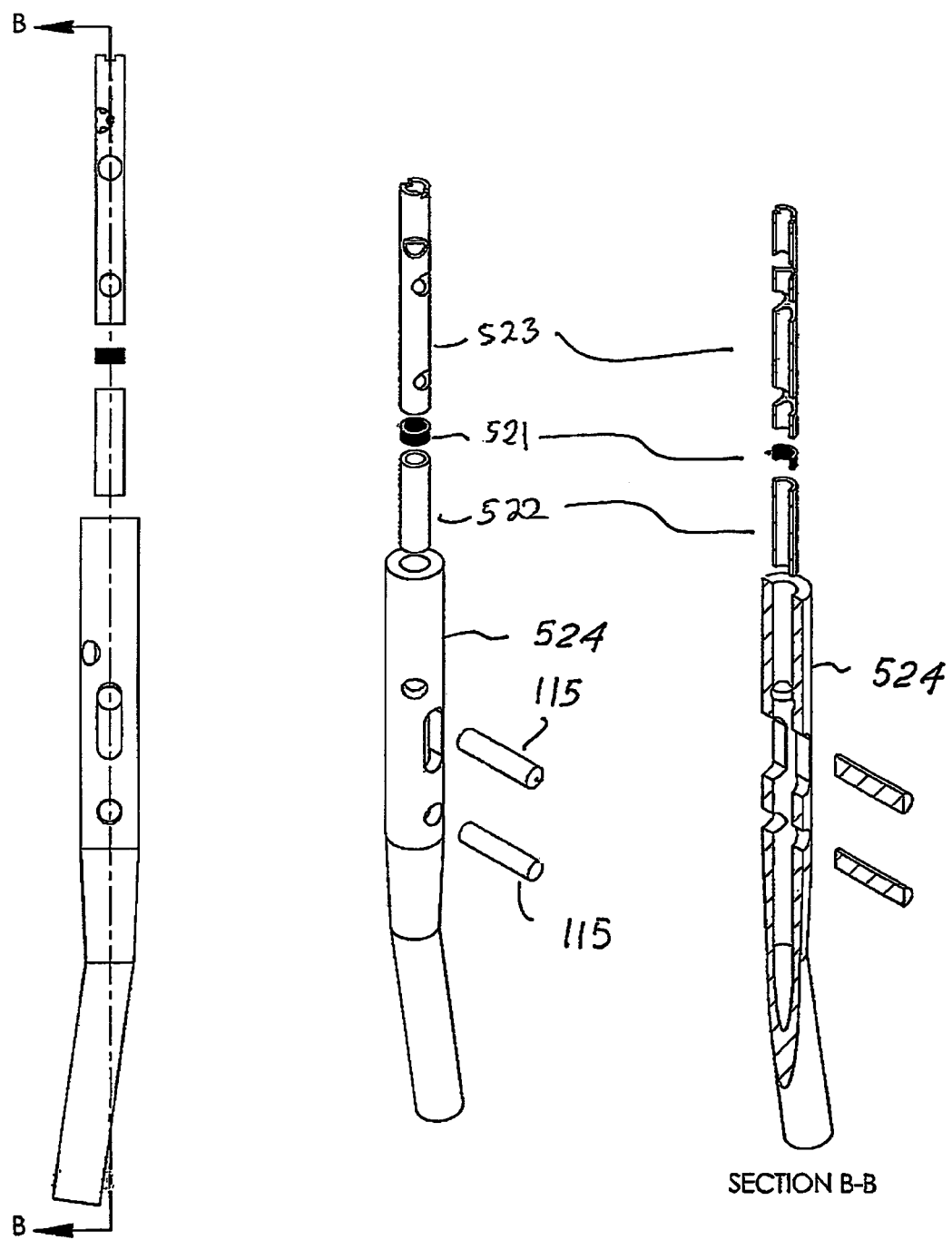

In a further embodiment (FIGS. 54 and 55), in a nail 520 damping action provided by the tissue may be augmented by the addition of a plurality of Belleville washers 521 or other energy-storage elements, which are compressed during stance phase and rebound to their initial shape during swing phase. The Belleville washers 521 rest on a plug 522 and are compressed by a tube 523, which transmits loads from the proximal bone screws 115 extending through a stem 524.

In an alternative embodiment the Belleville washers 521 may be seated on a pre machined shoulder in the nail and are compressed by the tube, which transmits loads from the bone screws. In any of the embodiments discussed above, the holes for the bone screws may be aligned in a single plane or in a series of oblique planes rotated about the longitudinal axis of the nail.

Figure 56:
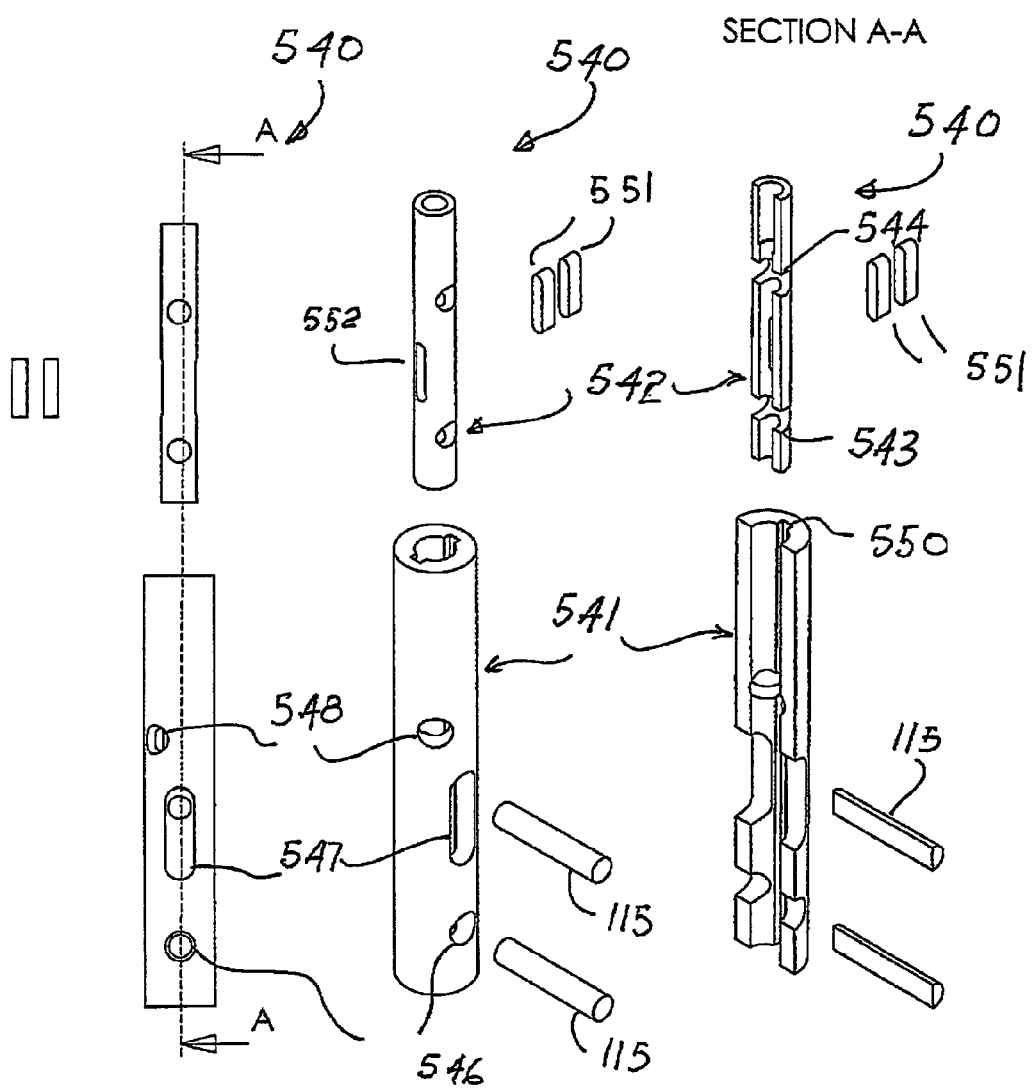
Figure 57:
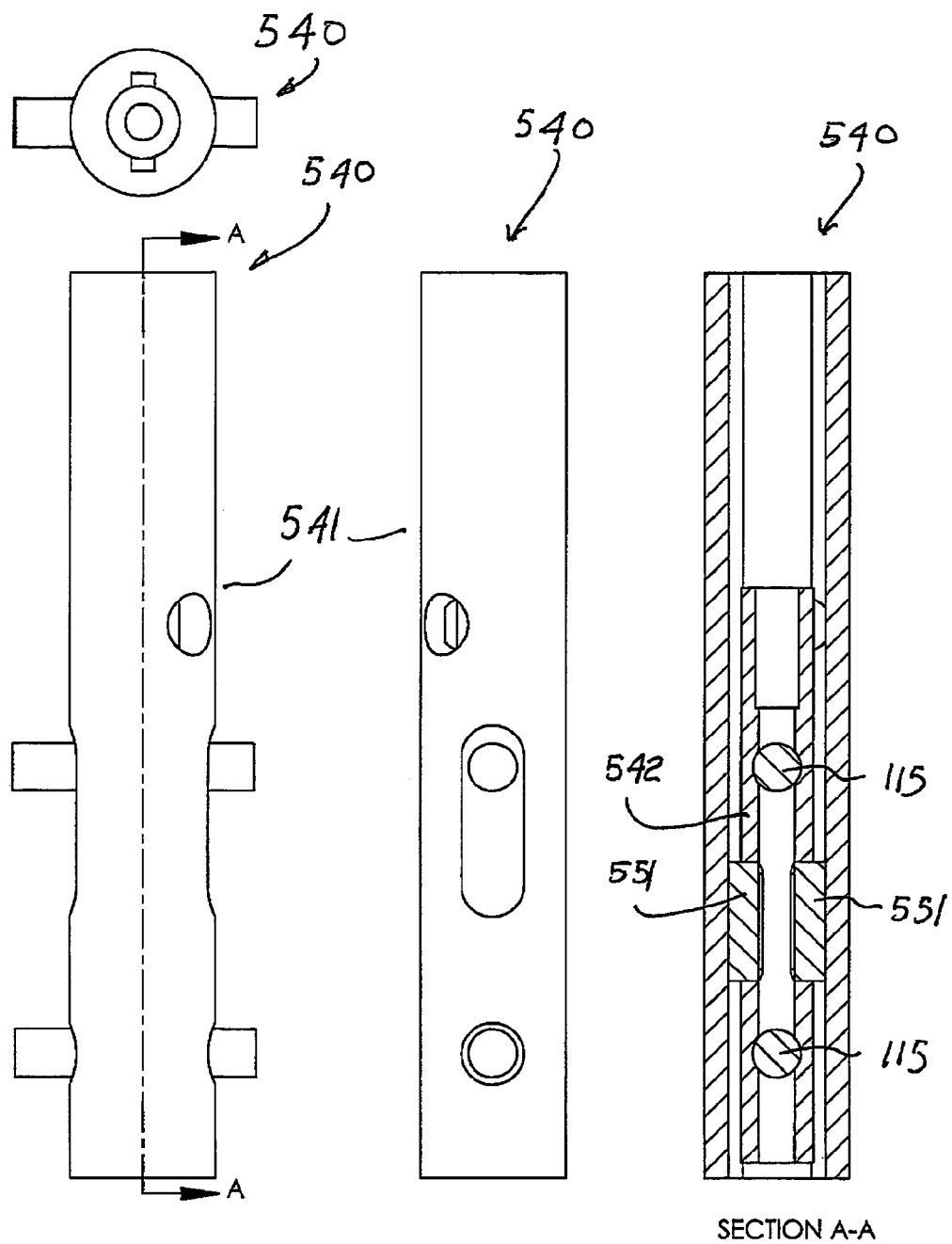
Figure 58:
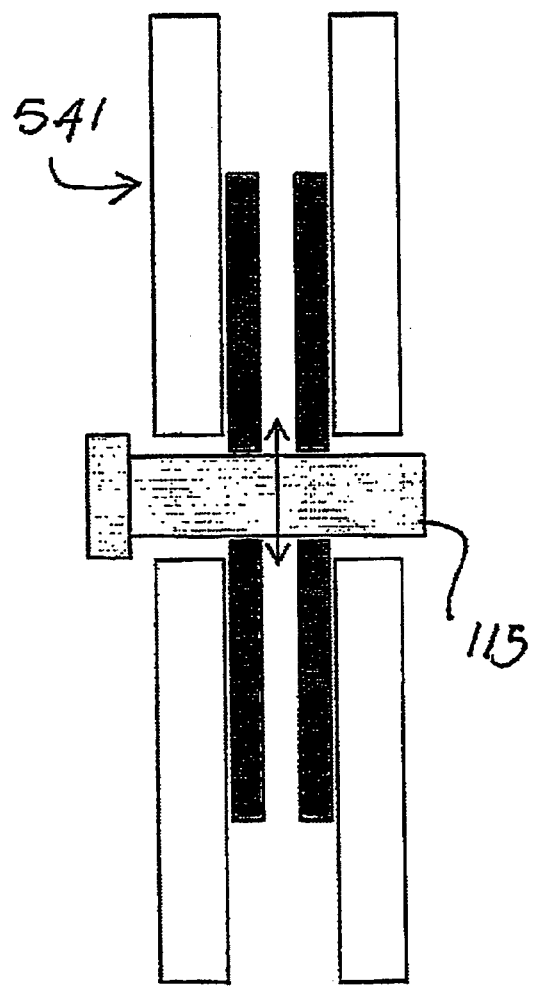
FIG. 58 is a diagram illustrating alignment of a bone screw through a nail stem in such a way as to admit controlled micromotion.

Referring to FIG. 56 a nail 540 has a stem 541 and an insert 542. The insert 542 has through holes 543 and 544, and the stem has a corresponding through-hole 546 and a slot 547. The insert 542 also has slots 552, into which keys 551 are fitted. The stem 541 has an axial groove 550 in which the keys 551 slide to ensure that the insert 542 has only axial translation relative to the stem 541 and no rotational freedom. The through-hole 546 in the insert 542 ensures that the bone screw inserted through the stem is perfectly normal to the axis, as illustrated in FIG. 58. In another embodiment the groove may be in the insert 542 and the slots in the stem 541.

It will be appreciated from the embodiments of FIGS. 52 to 56 that micromotion can be allowed by using a bone screw that has a smaller diameter than the hole in the nail that it passes through. The amount of micromotion in this configuration is determined by the difference in diameter between the bone screw and the hole in the nail. The insert ensures that the screw does not enter the hole off-axis, which would result in no micromotion. The insert guides the bone screw into correct alignment within the hole as needed to ensure micromotion. Axial loads pass directly from the bone screw to the nail, not through the insert. In this embodiment, the insert is merely a surgical guide to aid bone screw alignment and it does not take axial forces.

It will be appreciated that additional rotational stability could be advantageous to bone healing and could be achieved in several ways:
  Reducing the width of the slot in the nail stem would prevent bone screw rotation and admit axial micromotion only with no rotational freedom.
  Including a keyway that aligns the insert inside the nail stem would ensure the nail and insert have only axial translation relative to one another and no rotational freedom.
  Forming the lumen of the nail stem with an elliptical cross-section and the corresponding insert with the same cross-section would ensure that nail and insert only have axial translation relative to one another and no rotational freedom.

In the first option presented above for providing additional rotational stability, the insert prevents skewed insertion of the bone screw as shown in FIG. 58, but the insert itself is not load bearing for either axial or torsional loads. In the second and third options above, the insert is load bearing under torsional loads, but not load bearing under axial loads.

In one embodiment, one or more of the holes in the nail stem may be elongated to form a short slot with width equal to the diameter of the bone screw and length equal to the diameter of the bone screw plus the required interfragmentary micromotion distance. To lock the micromotion-enabled nail, the surgeon inserts a bone screw through the short slot to provide torsional stability with axial micromotion. A second bone screw may also be added in a longer dynamic slot.

It will be appreciated that the embodiments described herein can be manufactured using known techniques. For example, the components of the motion assembly shown in FIGS. 15 to 18 comprise two computer numerically controlled (CNC) machined tubes 106 and 107 with the addition of slots 120 and 121 by wire electrical discharge machining (EDM) and an externally machined thread on tube 107. Pins 108 are standard turned shafts. The device is assembled by sliding tube 106 into 107 and pressing pins 108 into slots 106, 107 respectively. In FIGS. 19 to 22, variations of the embodiment are presented to facilitate spring damping by means of Belleville washers, which are standard machine components not requiring unknown manufacturing techniques and having no affect on the manufacturing of the components previously described. In another embodiment shown in FIGS. 52 and 53, a CNC machined tube 507 has a number of holes 501, 502, and 503, each produced according to standard techniques.

The invention is not limited to the embodiment hereinbefore described, with reference to the accompanying drawings, which may be varied in construction and detail. For example the micromotion assembly may include a spring of a different type such as a coil spring or a leaf spring. The micromotion assembly may include non-spring dampers and restoring force systems such as elastic, macromolecular, visco-elastic, magnetic, electric, electromagnetic, pneumatic, hydraulic, oleo-pneumatic, electro- and magneto-hydrodynamic pumping systems. Also, resilience may be provided by the inherent properties of part of the nail. For example, a polymer sleeve for the bone-fastening screws may be resilient, thus providing the required spring resilience and/or damping.

Also, alternative mechanisms could be used to limit separation of the bone fragments during the swing phase. Any locking mechanism which is strong enough to withstand the necessary forces and which engages at a set position could be used. It need not necessarily be a ratchet mechanism as it may be required in some embodiments to allow bi-directional movement for re-adjustment. For example, an arrangement akin to the ball-and-spring arrangement employed in crutches may be employed.

Also, it is envisaged that there may be more than one micromotion assembly in the nail. Also, its orientation could be adjustable.

The improvements compared to a standard interlocked intramedullary nail that are facilitated by the embodiments presented in detail herein can also be achieved through different embodiments, which are given here by way of example, with reference to the accompanying drawings.

The invention claimed is:

1. An intramedullary nail comprising:
    a nail stem;
    an insert within the nail stem and having an insert bone screw aperture to receive a bone screw for engagement with a proximal bone fragment;
    the nail stem having a distal aperture to receive a bone screw for engagement with a distal bone fragment, and a proximal aperture arranged for alignment with said insert bone screw aperture;
    a motion assembly allowing limited and repeated relative axial relative movement of the insert and the nail stem;
    wherein the insert is adapted to guide insertion of a bone screw through the stem proximal aperture, and the insert is constrained by being keyed in the stem to move axially only within the stem without relative rotation of the insert and the stem;
    wherein said motion assembly is adapted to allow limited and repeated axial relative movement of the insert and the stem of less than 1.5 mm by a difference in cross-sectional size between the bone screw and the stem proximal aperture, said difference allowing movement,
    wherein the motion assembly is adapted to provide spring bias and/or damping between the nail stem and the insert, and wherein the motion assembly comprises a removable spring.

2. The intramedullary nail as claimed in claim 1, wherein the spring comprises a plurality of spring elements.

3. The intramedullary nail as claimed in claim 1, wherein the spring or spring elements comprise one or more Belleville washers.

4. An intramedullary nail comprising:
    a nail stem;
    an insert within the nail stem and having an insert bone screw aperture to receive a bone screw for engagement with a proximal bone fragment;
    the nail stem having a distal aperture to receive a bone screw for engagement with a distal bone fragment, and a proximal aperture arranged for alignment with said insert bone screw aperture;
    a motion assembly allowing limited and repeated relative axial relative movement of the insert and the nail stem;
    wherein the insert is adapted to guide insertion of a bone screw through the stem proximal aperture, and the insert is constrained by being keyed in the stem to move axially only within the stem without relative rotation of the insert and the stem;
    wherein said motion assembly is adapted to allow limited and repeated axial relative movement of the insert and the stem of less than 1.5 mm by a difference in cross-sectional size between the bone screw and the stem proximal aperture, said difference allowing movement; and
    wherein the nail comprises a surgeon adjustment interface which translates rotational movement caused by a surgeon into axial movement within the stem to close the gap between the proximal and distal bone fragments.

5. The intramedullary nail as claimed in claim 4, wherein the interface comprises an exposed screw which pushes an internal sliding and non-rotating component within the stem.

6. The intramedullary nail as claimed in claim 4, wherein the motion assembly is adapted to allow movement without bias or damping.

* * * * *